United States Patent
Denolf et al.

(10) Patent No.: US 10,975,380 B2
(45) Date of Patent: Apr. 13, 2021

(54) SEED-SPECIFIC AND ENDOSPERM-PREFERENTAL PROMOTERS AND USES THEREOF

(71) Applicant: BASF AGRICULTURAL SOLUTIONS SEED, US LLC, Research Triangle Park, NC (US)

(72) Inventors: Peter Denolf, Velzeke (BE); Katrien Van Audenhove, Ghent (BE); John Teske, Ghent (BE)

(73) Assignee: BASF AGRICULTURAL SOLUTIONS SEED, US LLC, Research Triangle Park, NC (US)

( * ) Notice: Subject to any disclaimer, the term of this patent is extended or adjusted under 35 U.S.C. 154(b) by 4 days.

(21) Appl. No.: 16/092,716

(22) PCT Filed: Apr. 6, 2017

(86) PCT No.: PCT/EP2017/058208
§ 371 (c)(1),
(2) Date: Oct. 10, 2018

(87) PCT Pub. No.: WO2017/178318
PCT Pub. Date: Oct. 19, 2017

(65) Prior Publication Data
US 2019/0085346 A1    Mar. 21, 2019

(30) Foreign Application Priority Data

Apr. 11, 2016 (EP) ..................... 16164663

(51) Int. Cl.
*C12N 15/82* (2006.01)
*C12N 15/113* (2010.01)

(52) U.S. Cl.
CPC ........ *C12N 15/8234* (2013.01); *C12N 15/113* (2013.01); *C12N 15/8242* (2013.01); *C12N 15/8279* (2013.01)

(58) Field of Classification Search
None
See application file for complete search history.

(56) References Cited

U.S. PATENT DOCUMENTS

| | | |
|---|---|---|
| 4,757,011 A | 7/1988 | Chaleff et al. |
| 4,769,061 A | 9/1988 | Comai |
| 4,940,835 A | 7/1990 | Shah et al. |
| 4,971,908 A | 11/1990 | Kishore et al. |
| 5,004,863 A | 4/1991 | Umbeck |
| 5,593,874 A | 1/1997 | Brown et al. |
| 5,641,876 A | 6/1997 | McElroy et al. |
| 5,659,122 A | 8/1997 | Austin |
| 5,767,363 A | 6/1998 | De Silva et al. |
| 5,952,489 A | 9/1999 | Okada et al. |
| 6,342,657 B1 | 1/2002 | Thomas et al. |
| 6,483,013 B1 | 11/2002 | Reynaerts et al. |
| 6,759,570 B1 | 7/2004 | Prieto-Dapena et al. |
| 7,071,378 B1 | 7/2006 | Bonello et al. |
| 7,642,346 B2 | 1/2010 | Chaudhary et al. |
| 8,552,256 B2 | 10/2013 | Takaiwa et al. |
| 2005/0144667 A1 | 6/2005 | Stanley et al. |
| 2007/0169226 A1 | 7/2007 | Habben et al. |
| 2007/0199106 A1 | 8/2007 | Stahl et al. |
| 2009/0227013 A1 | 9/2009 | Helentjaris et al. |
| 2009/0241230 A1 | 9/2009 | Duwenig et al. |
| 2011/0093984 A1 | 4/2011 | Takaiwa et al. |

FOREIGN PATENT DOCUMENTS

| | | |
|---|---|---|
| EP | 0242236 A1 | 10/1987 |
| EP | 0242246 A1 | 10/1987 |
| EP | 0507698 A1 | 10/1992 |
| EP | 0508909 A1 | 10/1992 |
| JP | 2003-159071 A | 6/2003 |
| WO | WO-90/12107 A1 | 10/1990 |
| WO | WO-98/08961 A2 | 3/1998 |
| WO | WO-99/53050 A1 | 10/1999 |
| WO | WO-00/71733 A1 | 11/2000 |
| WO | WO-01/12824 A1 | 2/2001 |
| WO | WO-03/052108 A2 | 6/2003 |
| WO | WO-03/076619 A1 | 9/2003 |
| WO | WO-2004/073390 A1 | 9/2004 |
| WO | WO-2005/042745 A1 | 5/2005 |
| WO | WO-2005/047505 A2 | 5/2005 |
| WO | WO-2005/049842 A2 | 6/2005 |
| WO | WO-2005/052170 A2 | 6/2005 |

(Continued)

OTHER PUBLICATIONS

Ellerstrom et al, Plant Mol Biol 32: 1019-1027, 1996 (Year: 1996).*
"BONQT13TR BO 1.6 2 KB tot *Brassica oleracea* genomic clone—BONQT13, genomic survey sequence.", Database EMBL [Online], XP002771226, Dec. 19, 2002, Database accession No. BZ469823, 1 page.
Ayele, et al., "Whole genome shotgun sequencing of *Brassica oleracea* and its application to gene discovery and annotation in *Arabidopsis*", Genome Research, vol. 15, Issue 4, Apr. 2005, pp. 487-495.
Barta, et al., "DoOP: Databases of Orthologous Promoters, collections of clusters of orthologous upstream sequences from chordates and plants", Nucleic Acids Research, vol. 33, Jan. 2005, pp. D86-D90.

(Continued)

*Primary Examiner* — Elizabeth F McElwain
(74) *Attorney, Agent, or Firm* — Arent Fox LLP

(57) ABSTRACT

The present invention relates to *Brassica* sequences comprising early stage seed-specific and endosperm-preferential promoter activity. Provided are recombinant genes comprising the early stage seed-specific and endosperm-preferential promoter operably linked to a heterologous nucleic acid sequence, and cells, plants and seeds comprising the recombinant gene. The promoters can be used to alter gene expression specifically in the seeds at early developmental stages and preferentially in the endosperm and to alter biotic or abiotic stress tolerance, yield, seed quality or seed properties.

21 Claims, 12 Drawing Sheets

Specification includes a Sequence Listing.

(56) References Cited

FOREIGN PATENT DOCUMENTS

| WO | WO-2005/098004 A2 | 10/2005 |
|---|---|---|
| WO | WO-2006/074400 A2 | 7/2006 |
| WO | WO-2007/110600 A2 | 10/2007 |
| WO | WO-2010/118477 A1 | 10/2010 |
| WO | WO-2010/129999 A1 | 11/2010 |
| WO | WO-2010/147825 A1 | 12/2010 |
| WO | WO-2012/159891 A1 | 11/2012 |
| WO | WO-2013/108017 A1 | 7/2013 |
| WO | WO-2015/022192 A1 | 2/2015 |
| WO | WO-2015/067943 A1 | 5/2015 |

OTHER PUBLICATIONS

Huang, et al., "Probing the endosperm gene expression landscape in *Brassica napus*", BMC Genomics, vol. 10, Issue 256, Jun. 2009, 19 pages.

Hwang, et al., "Analysis of the rice endosperm-specific globulin promoter in transformed rice cells", Plant Cell Reports, vol. 20, Issue 9, Feb. 2002, pp. 842-847.

International Search Report for PCT Patent Application No. PCT/EP2017/058208, dated Jul. 24, 2017, 5 pages.

Lamacchia, et al., "Endospermspecific activity of a storage protein gene promoter in transgenic wheat seed", Journal of Experimental Botany, vol. 52, Issue 355, Feb. 2001, pp. 243-250.

Li, et al., "Control of final seed and organ size by the DA1 gene family in *Arabidopsis thaliana*", Genes and Development, vol. 22, Issue 10, May 15, 2008, pp. 1331-1336.

Li, et al., "The putative phytocyanin genes in Chinese cabbage (*Brassica rapa* L.): genome-wide identification, classification and expression analysis", Molecular Genetics and Genomics, vol. 288, Issue 1-2, Feb. 2013, pp. 1-20.

Mashiguchi, et al., "Genome-Wide Identification, Structure and Expression Studies, and Mutant Collection of 22 Early Nodulin-Like Protein Genes in *Arabidopsis*", Bioscience, Biotechnology, and Biochemistry, vol. 73, Issue 11, Nov. 2009, pp. 2452-2459.

Needleman, et al., "A general method applicable to the search for similarities in the amino acid sequence of two proteins", Journal of Molecular Biology, vol. 48, Issue 3, Mar. 28, 1970, pp. 443-453.

Pearson, et al., "Improved tools for biological sequence comparison", Proceedings of the National Academy of Science of the United States of America, vol. 85, Issue 8, Apr. 1988, pp. 2444-2448.

Russell, et al., "Tissue-specific expression in transgenic maize of four endosperm promoters from maize and rice", Transgenic Research, vol. 6, Issue 2, Mar. 1997, pp. 157-168.

Schiebold, et al., "A novel procedure for the quantitative analysis of metabolites, storage products and transcripts of laser microdissected seed tissues of *Brassica napus*", Plant Methods, vol. 7, Issue 19, Jun. 30, 2011, 14 pages.

Song, et al., "Isolation and Characterization of an Endosperm-Specific Promoter from Wheat (*Triticum aestivum* L.)", Zeitschrift für Naturforschung C—A Journal of Biosciences, vol. 67, Issue 11-12, 2012, pp. 611-619.

Tiwari, et al., "Proliferative phase endosperm promoters from *Arabidopsis thaliana*", Plant Biotechnology Journal, vol. 4, Issue 4, Jul. 2006, pp. 393-407.

Wu, et al., "Promoters of Rice Seed Storage Protein Genes Direct Endosperm-Specific Gene Expression in Transgenic Rice", Plant and Cell Physiology, vol. 39, Issue 8, Aug. 1, 1998, pp. 885-889.

Denolf, Peter et al., "Seed-Specific and Endosperm-Preferental Promoters and Uses Thereof", U.S. Appl. No. 16/092,734, filed Oct. 10, 2018.

\* cited by examiner

```
ENODL3-4 BnA1      1 mglikrfdaylmtvmlmsig-faigfsngykfyvggrdgwvltpsedysh
ENODL3-4 BnA2      1 mglvktfdvylmivmlagiv-falgisngykfyvggkdgwvltpsedysh
ENODL3-4 BnC1      1 mglikrfdaylmtvmlvsig-faigfsngykfyvggrdgwvltpsedysh
ENODL3-4 BnC2      1 mglvksfdaylmivmltgiv-falgisngykfyvggkdgwvltpsedysh
ENODL3-4 BjB2      1 mglvksfgaylmtvmlsgiv-falgisngykfyvggkdgwvltpsedysh
ENODL3-4 BjA1      1 mgliksfdaylmivmflsig-iaigfsngykfsvggkdgwvlapsedysh
ENODL3-4 BjB1      1 mglikrfdaylmtvmlmsig-faigfsngykfyvggrdgwvltpsedysh
ENODL3-4 BjA2      1 mglvktfdaylmivmlagiv-falgisngykfyvggkdgwvltpsedysh
ENODL3-4 BoC2      1 mglvksfdaylmivmltgiv-falgisngykfyvggrdgwvltpsedysh
ENODL3-4 BoC1      1 mglikrfdaylmtvmlimsiglfaigfsngykfyvggrdgwvltpsedysh
ENODL3-4 BrA1      1 mglikrfdaylmtvmlmsig-faigfsngykfyvggrdgwvltpsedysh
ENODL3-4 BrA2      1 mglvktfdaylmivmlagiv-falgisngykfyvggkdgwvltpsedysh
Consensus            ***.*:******.*:*  *   *.*:****** * *******.******

ENODL3-4 BnA1     50 wsyrsrfqvndtlyfkypkgkdsvlevseeefntcntthpitsltdgdsl
ENODL3-4 BnA2     50 wshrnrfqvndtlyfkypkgkdsvlevseeeyntcntthpitsvsdggsl
ENODL3-4 BnC1     50 wsyrsrfqvndtlyfkypkgkdsvlevseeefntcntthpitsltdgdsl
ENODL3-4 BnC2     50 wshrnrfqvndtlyfkypkgkdsvlevseeeyntcntthpitsltdgdsl
ENODL3-4 BjB2     50 wshrnrfqvndtlyfkypkgkdsvvevseeeyntcntthpitsltdgdsl
ENODL3-4 BjA1     50 wshrnrfqvndtlyfkytegkdsvlevsgeeynkcntthpitsltdgdsl
ENODL3-4 BjB1     50 wshrnrfqvndtlyfkypkgkdsvlevsqeeyntcntthpitslsdgdsl
ENODL3-4 BjA2     50 wsyrsrfqvndtlyfkypkgkdsvlevseeefntcntthpitsltdgdsl
ENODL3-4 BoC2     50 wshrnrfqvndtlyfkypkgkdsvvevseeeyntcntthpitsvsdggsl
ENODL3-4 BoC1     50 wshrnrfqvndtlyfkypkgkdsvlevseeeyntcntthpitslsdgdsl
ENODL3-4 BrA1     51 wsyrsrfqvndtlyfkypkgkdsvlevseeefntcntthpitsltdgdsl
ENODL3-4 BrA2     50 wshrnrfqvndtlyfkypkgkdsvlevseeeyntcntthpitsvsdggsl
Consensus            ** * *************.:*********:***.******:.** **
```

Figure 4

```
ENODL3-4 BnA1      100 yvlsrsgpfffvsgnsenclkggklpvkvmsaahhshsprqpspspspsp
ENODL3-4 BnA2      100 fvlsrsgpfffvsgnsenclkggklavnvmstahhshsprqpspspspsp
ENODL3-4 BnC1      100 yvlsrsgpfffvsgnsenclkggklpvkvmstahhshsprqpspspspss
ENODL3-4 BnC2      100 fvlsrsgpfffvsgnsenclkggklavnvmstahhshsprq--pspspsp
ENODL3-4 BjB2      100 fvlsrsgpfffvsgnsencvkggklavkvmstahhshsprqsspspspa-
ENODL3-4 BjA1      100 fvlsrsgpfffvsgisanclkggklavkvmsaahhshsprqpspspspsp
ENODL3-4 BjB1      100 yvlsrsgpfffvsgnsenclkggklpvkvmsaahhshsprqpspspspsp
ENODL3-4 BjA2      100 fvlsnsgpfffvsgnsenclkggklavnvmstahhsrsprq--pspspsp
ENODL3-4 BoC2      100 fvlsrsgpfffvsgnsenclkggklpvkvmsaahhshsprqpspspspsp
ENODL3-4 BoC1      101 yvlsrsgpfffvsgnsenclkggklavnvmstahhsrsprq--pspspsp
ENODL3-4 BrA1      100 yvlsrsgpfffvsgnsenclkggklpvkvmsaahhshsprqpspspspsp
ENODL3-4 BrA2      100 fvlsnsgpfffvsgnsenclkggklavnvmstahhsrsprqpspspspsp
Consensus              :*** ******.*******: *** :****** ******.* ******

ENODL3-4 BnA1      150 tlsp--shqalsspapsprvlseseaIapapgpakahnsagIvspravs
ENODL3-4 BnA2      150 sptl--spiawsspapspgvvlsdseaIapapepakarnsacIvgpgmvs
ENODL3-4 BnC1      150 tlsp--shqalsspapsprvlseseaIapapgpakahnsagIvsprgvs
ENODL3-4 BnC2      148 tlsp----vawsspapspgvelsdseaIapapgpakahnsagIvgpgmvs
ENODL3-4 BjB2      149 -lsp----valsspapspgvalsds-------gpakarnsagIvgpemvs
ENODL3-4 BjA1      150 tlsp----vhqa--spapsprvlsdteaIapapgpakahnaagIvspravs
ENODL3-4 BjB1      150 tlsp--shqalsspapsprvlseseaIapapepakahnsagIvspravs
ENODL3-4 BjA2      150 spsptlspiawsspapspgvvlsdseaIapapepakarnsacIvgpgmvs
ENODL3-4 BoC2      148 tlsp----vawsspapspgvelsdseaIapapasepakahnsagIvspravs
ENODL3-4 BoC1      151 tlsp--shqalsspapsprvlseseaIapapgpakahnsagIvspravs
ENODL3-4 BrA1      150 tlsp--shqalsspapspgvvlsdseaIapapepakahnsagIvspravs
ENODL3-4 BrA2      150 spsptispiawsspapspgvvlsdseaIapapepakarnsacIvgpgmvs
Consensus                 *         ******  * **::   *. * **.:* ** ** 
```

Figure 4 (continued)

```
ENODL3-4 BnA1  198 lglvlvviisfvl
ENODL3-4 BnA2  198 lglvlfvfirsmv
ENODL3-4 BnC1  198 lglvlvviisfmv
ENODL3-4 BnC2  194 lglvlvvfirsmv
ENODL3-4 BjB2  187 lglvlgvvissmv
ENODL3-4 BjA1  196 lglvlvviincmv
ENODL3-4 BjB1  198 lglvlvviisfvv
ENODL3-4 BjA2  200 lglvlfvfirsmv
ENODL3-4 BoC2  194 lglvlvvfirsmv
ENODL3-4 BoC1  199 lglvlvviisfvv
ENODL3-4 BrA1  198 lglvlvviisfvv
ENODL3-4 BrA2  200 lglvlfvfirsmv
Consensus          ***** * * :
```

Figure 4 (continued)

```
Penodi3-4   BnA1   631  ------------------------aag----------aaaattga------at--------------ttcagct-------ttat
Penodi3-4   BnA2   621  attatgt-----------------aag----------cttattaacaattgat----------------ttcatt-------tttt
Penodi3-4   BnC1   621  ttatttttt---------------aag----------aaaattga------at----------------ttcagct-------ttat
Penodi3-4   BnC2   626  aaatctagt---------------aagtttattaaaaatga---------at----------------ttcagtt-------ttta
Penodi3-4   BjB2   616  aaacaagtt---------------tag----------aaaaataa------at----------------ttcagta-------ttta
Penodi3-4   BjA1   631  gtaatttta---------------aac----------agacatgg-----at----------------ttcagt-------ttaa
Penodi3-4   BjB1   616  gcaagttatttttt----------aag----------aaaattga------at----------------ttcagct-------ttat
Penodi3-4   BjA2   626  gt----------------------aag----------cttattaacaattgat----------------ttcattt-------tttt
Penodi3-4   BoC2   626  aatctagt----------------aagtttattaaaaatga---------at----------------ttcagtt-------ttta
Penodi3-4   BoC1   621  tacgcaagttatttaaaaaaa---------------aaaattaa------at----------------ttcagct-------ttat
Penodi3-4   BrA1   581  cgatcca-----------------aac----------caaaccaa-----ctatggtttacttcagctgaaaaattct-------
Penodi3-4   BrA2   626  tatgt-------------------aag----------cttattaacaattgat----------------ttcattt-------tttt Penodi3-4   BnA1   655  a---------------ttaaatgactgacaaattagaa--gatctagttttaaat---ggtt-------
Penodi3-4   BnA2   658  tgttttg---------ttagatgactgactaacaaattggaa--catctgttggaaaat---ggct-------
Penodi3-4   BnC1   655  a---------------ttaaatgactgactaacaaattagaa--gatctagttttaaat---ggtt-------
Penodi3-4   BnC2   665  g---------------ttaaatgactgactaacaaattggaa--catctggtgtaaaat---ggct-------
Penodi3-4   BjB2   649  g---------------ttaaatgactgactaataaatcggag--catcaggtgaaaaaaaggct-------
Penodi3-4   BjA1   664  a---------------ttaaatgactgactaacaaattagaa--gatctagttttaaat---ggtt-------
Penodi3-4   BjB1   655  a---------------ttaaatgactgacaaattagaa--catctgttggaaaat---ggct-------
Penodi3-4   BjA2   658  tgttttg---------ttagatgactgactaacaaattggaa--catctgttgaaaat---ggct-------
Penodi3-4   BoC2   664  g---------------ttaaatgactgactaacaaattggaa--catctggtgtaaaat---ggct-------
Penodi3-4   BoC1   663  a---------------ttaaatgactgactaacaaattagaa--gatctagtttcaaat---ggtt-------
Penodi3-4   BrA1   628  a---------------gaaccgaactaaccaaccgaaccgaactcgaaccgaac---cgataaaataaccgaagt
Penodi3-4   BrA2   661  t---------------ttgttagatgactaacaaattggaa--catctgttggaaat---ggct-------
                                        Motif 1
```

```
Penod13-4 BnA1  821 aattttgcatat--tctctagagagtcgaagttgatgcagccaaag------ct------aacggctat
Penod13-4 BnA2  813 aa-ttttgcatat--tctctagagagtcgaagataacc------catgcaggcaaaag------cttcatctaacggctat
Penod13-4 BnC1  821 aattttgcatat--tctctagagagtcgaagttgatgcagccaaag------ct------aacggctat
Penod13-4 BnC2  814 aa-ttttgcatat--tctctagagaatc------catgcaggaaaaagtttcacct------aacggctat
Penod13-4 BjB2  809 a-gtttgcacat--tctctagagaatc------catgcagccaaacg------cttcacctaacggctat
Penod13-4 BjA1  821 aattttgcatatattatctctagagattc------gatgcagccaaag------cttcaccaaacggctat
Penod13-4 BjB1  821 aattttgcatat--tctctagagagtcgaagttgatgcagccaaag------ct------aacggctat
Penod13-4 BjA2  813 aa-tttgcatat--tctcaagataacc------catgcaggcaaaag------cttcatctaacggctat
Penod13-4 BoC2  813 aa-tttgcatat--tctctagagaato------catgcaggcaaaaaagtttcacct------aacggctat
Penod13-4 BoC1  829 aattttgcatgt--tctctagagagtcgaagttgatgcagccaaag------tt------aacggctat
Penod13-4 BrA1  821 aattttgcatat--tctctagagagtcgaagttgatgcagccaaacc------ct------aacggctat
Penod13-4 BrA2  813 aa-tttgcatat--tctctagataacc------catgcaggcaaaag------cttcatctaacggctat
                                       motif 6                motif 7                motif 8

Penod13-4 BnA1  877 gacttctctactttcactatataaatacgcataca------agcactgaagagc------aacacacatttc
Penod13-4 BnA2  868 gacttatctgcttcactttcaccatataaatacacacataca------agcacccaagagc------aacacacagagttc
Penod13-4 BnC1  877 gacttctctactttcactttcaccatataaatacgcataca------agcactgaagagc------aacacacatttc
Penod13-4 BnC2  869 gacttctctactttcaccatataaatacacatacataca------agcactgaagagc------aacacacagagttc
Penod13-4 BjB2  864 tacttctctactttcaccatataaatacacatacacataca------agcactgaagagc------aacacacagagttc
Penod13-4 BjA1  879 gagttctctactttcaccatataaatacatgcaagcacccaagaggcaagagcaaacacagagttc
Penod13-4 BjB1  877 gacttctctactttcaccatataaatacgcataca------atcacccaagagt------a--acacagttc
Penod13-4 BjA2  868 gacttctctgcttcaccatataaatacacacataca------agcactgaagagc------aacacacatttc
Penod13-4 BoC2  868 gacttctctactttcaccatataaatacacacataca------agcacccaagagc------aacacacagagttc
Penod13-4 BoC1  885 gacttctctactttcactatataaatac------gcactgaagagc------aacacacatttc
Penod13-4 BrA1  877 gacttctctgcttcaccatataaatacgcataca------agcactgaagagc------aacacacatttc
Penod13-4 BrA2  868 gacttctctgcttcaccatataaatacacacataca------agcacccaagagc------aacacacagagttc
                                motif 9                           motif 10                motif 11

Figure 7 (continued)
```

```
Penod13-4  BnA1  935  aagagac------tgatttatttgaggtctagttaaag--tttggaggg--
Penod13-4  BnA2  926  aagagatcagtgagtaattgttttaaggtttagttacaagttttggagag--
Penod13-4  BnC1  935  aagagac------tgatttatttgaggtctagttaaag--tttggaggg--
Penod13-4  BnC2  927  aagagatcagtgagtaattacttgaggtttagttaaaa--cttttggga--
Penod13-4  BjB2  934  aagagag------cga-atacttgaggtttagttaaaagatttggaaag--
Penod13-4  BjA1  935  aaaagag------taatttacttgaggtctagttaaat--tttagagag--
Penod13-4  BjB1  935  aagagac------tgatttatttgaggtctagttaaag--tttggaggg--
Penod13-4  BjA2  926  aagagatcagtgagtaattgttttaaggtttagttacaagttttggagag--
Penod13-4  BoC2  926  aagagatcagtgagtaattacttgaggtttagttaaaa--cttttgggag--
Penod13-4  BoC1  935  aagagac------tgatttatttgaggtctagttcaaag--tttggagag--
Penod13-4  BrA1  935  aagagat------tgatttatttgaggtctagttaaag--tttggaggg--
Penod13-4  BrA2  926  aagagatcagtgagtaattgttttaaggtttagttacaagttttggagag--
                                                    ━━━━━━━━━━━━━━━━
                                                         motif 12
```

SEED-SPECIFIC AND ENDOSPERM-PREFERENTAL PROMOTERS AND USES THEREOF

CROSS-REFERENCE TO RELATED APPLICATIONS

This application is a 35 U.S.C. § 371 National Phase of PCT Application No. PCT/EP2017/058208 filed Apr. 6, 2017, which claims priority to European Application No. EP 16164663.3 filed Apr. 11, 2016, the disclosures of each of which are hereby incorporated by reference in their entirety.

FIELD OF THE INVENTION

The present invention relates to materials and methods for the expression of a gene of interest specifically in seeds of plants. In particular, the invention provides an expression cassette for regulating seed-specific and endosperm-preferential expression in plants.

BACKGROUND

Modification of plants to alter and/or improve phenotypic characteristics (such as productivity or quality) requires the overexpression or down-regulation of endogenous genes or the expression of heterologous genes in plant tissues. Such genetic modification relies on the availability of a means to drive and to control gene expression as required. Indeed, genetic modification relies on the availability and use of suitable promoters which are effective in plants and which regulate gene expression so as to give the desired effect(s) in the transgenic plant.

For numerous applications in plant biotechnology a tissue-specific or a tissue-preferential expression profile is advantageous, since beneficial effects of expression in one tissue may have disadvantages in others.

Seed-preferential or seed-specific promoters are useful for expressing or down-regulating genes specifically in the seeds to get the desired function or effect, such as improving disease resistance, herbicide resistance, modifying seed or grain composition or quality, such as modifying starch quality or quantity, modifying oil quality or quantity, modifying amino-acid or protein composition, improving tolerance to biotic or abiotic stress, increasing yield, or altering metabolic pathways in the seeds.

Examples of seed-preferential or seed-specific promoters include the Tonoplast Intrinsic Protein alpha promoter from *Arabidopsis thaliana* (US patent application US2009/0241230), the KNAT411 promoter from *Arabidopsis thaliana* (U.S. Pat. No. 6,342,657), an oleosin promoter, a 2S storage protein promoter or a legumin-like seed storage protein promoter from *Linum usitatissimum* (U.S. Pat. No. 7,642,346), the acyl carrier protein promoter from *Brassica napus* (US Pat. Application No. 1994/0129129), the β-amylase promoter of barley (US Pat. Application No. 1997/0793599), and the Ha ds10 G1 promoter of sunflower (U.S. Pat. No. 6,759,570).

Several endosperm-preferential promoters have been identified from cereals, such as rice (Wu et al., 1998, Plant Cell Physiol 39: 885; Russell and Fromm, 1997, Transgenic Res 6:157; Hwang et al., 2002, Plant Cell Rep 9:842; US 2011/0093984, U.S. Pat. No. 8,552,256), maize (U.S. Pat. No. 7,071,378, US 2007/0169226, US 2009/0227013, WO 2005/042745, WO 2010/147825; WO 2012/159891), wheat (Lamacchia et al., 2001, J Exp Bot 52:243; Song et al., 2012, Z Naturforsch C 67:611; WO 2010/129999, WO 2010/118477), and barley (US 2007/0199106, WO 1998/008961). Endosperm-preferential promoters have also been identified in the model plant *Arabidopsis* (WO2007/110600; Tiwari et al., 2006, Plant Biotech J. 4: 393). Knowledge on endosperm-preferential promoters from exalbuminous crop plants or from oil-accumulating crop plants is limited. Huang et al., 2009, BMC Genomics 10:256 have identified about 1200 genes expressed in the endosperm of *Brassica napus* during embryo development in *Brassica napus*. However, this study did not compare expression of the genes in the endosperm to expression in other plant tissues, and focused on very early seed-developmental stages. Further, Huang et al did not identify the sequences of the promoters of the genes accumulating in the endosperm.

There remains thus an interest in the isolation of novel early stage seed-specific promoters having endosperm-preferential activity. It is thus an objective of the present invention to provide *Brassica* promoters having early stage seed-specific activity and endosperm-preferential activity. This objective is solved by the present invention as herein further explained.

SUMMARY

In one aspect, the invention provides an isolated nucleic acid comprising early stage seed-specific and endosperm-preferential promoter activity selected from the group consisting of (a) a nucleic acid comprising a nucleotide sequence of any one of SEQ ID NOs: 2 to 13 or a functional fragment thereof; and (b) a nucleic acid comprising a nucleotide sequence having at least 95% sequence identity to any one of SEQ ID NOs: 2 to 13 or a functional fragment thereof.

Furthermore, the provided isolated nucleic acid comprises the nucleotide sequence of SEQ ID NO: 38, the nucleotide sequence gtgaaaaga, the nucleotide sequences of SEQ ID NOs: 39 to 41, the nucleotide sequence tttgcayrt, the nucleotide sequences of SEQ ID NOs: 42 to 47.

A further embodiment provides a recombinant gene comprising the nucleic acid according to the invention operably linked to a heterologous nucleic acid sequence encoding an expression product of interest, and optionally a transcription termination and polyadenylation sequence, preferably a transcription termination and polyadenylation region functional in plant cells. In a further embodiment, said expression product of interest is an RNA capable of modulating the expression of a gene or is a protein.

Yet another embodiment provides a host cell, such as an *E. coli* cell, an *Agrobacterium* cell, a yeast cell, an algae, or a plant cell, comprising the isolated nucleic acid according to the invention, or the recombinant gene according to the invention.

In a further embodiment, a plant is provided comprising the recombinant gene according to the invention. Yet a further embodiment provides seeds obtainable from the plant according to the invention. In another embodiment, the plants or plant parts according to the invention are seed crop plants or seeds.

Yet another embodiment provides a method of producing a transgenic plant comprising the steps of (a) introducing or providing the recombinant gene according to the invention to a plant cell to create transgenic cells; and (b) regenerating transgenic plants from said transgenic cell.

Further provided is a method of effecting early stage seed-specific and endosperm-preferential expression of a nucleic acid comprising introducing the recombinant gene according to the invention into the genome of a plant, or providing the plant according to the invention. Also provided is a method for altering seed properties of a plant or to produce a commercially relevant product in a plant, said method comprising introducing the recombinant gene according to the invention into the genome of a plant, or providing the plant according to the invention. In another embodiment, said plant is a seed crop plant.

Also provided is the use of the isolated nucleic acid according to the invention to regulate expression of an operably linked nucleic acid in a plant, and the use of the isolated nucleic acid according to the invention, or the recombinant gene according to the invention to alter seed properties of a plant or to produce a commercially relevant product in a plant. In a further embodiment, said plant is a seed crop plant.

Yet another embodiment provides a method of producing food, feed, or an industrial product comprising (a) obtaining the plant or a part thereof, according to the invention; and (b) preparing the food, feed or industrial product from the plant or part thereof. In another embodiment, said food or feed is oil, meal, grain, starch, flour or protein, or said industrial product is biofuel, fiber, industrial chemicals, a pharmaceutical or a nutraceutical.

BRIEF DESCRIPTION OF THE DRAWINGS

FIG. 4: Alignment of the amino acid sequence of different Brassica ENODL3-4 proteins: ENODL3-4 BnA1 (SEQ ID NO: 17), ENODL3-4 BnA2 (SEQ ID NO: 16), ENODL3-4 BnC1 (SEQ ID NO: 15), ENODL3-4 BnC2 (SEQ ID NO: 14), ENODL3-4 BjB2 (SEQ ID NO: 22), ENODL3-4 BjA1 (SEQ ID NO: 25), ENODL3-4 BjB1 (SEQ ID NO: 23), ENODL3-4 BjA2 (SEQ ID NO: 24), ENODL3-4 BoC2 (SEQ ID NO: 18), ENODL3-4 BoC1 (SEQ ID NO: 19), ENODL3-4 BrA1 (SEQ ID NO: 21), ENODL3-4 BrA2 (SEQ ID NO: 20). Amino acid residues conserved in all proteins are indicated by an asterisk, conserved amino acid substitutions are indicated by a colon. The lowest identity between any two ENODL3-4 proteins is about 80%.

FIG. 7: Alignment of the 3' end of the nucleotide sequence of the Brassica Penodl3-4 promoters from Brassica napus, Brassica juncea, Brassica oleracea and Brassica rapa: ENODL3-4 BnA1 (SEQ ID NO: 51), ENODL3-4 BnA2 (SEQ ID NO: 50), ENODL3-4 BnC1 (SEQ ID NO: 49), ENODL3-4 BnC2 (SEQ ID NO: 48), ENODL3-4 BjB2 (SEQ ID NO: 56), ENODL3-4 BjA1 (SEQ ID NO: 59), ENODL3-4 BjB1 (SEQ ID NO: 57), ENODL3-4 BjA2 (SEQ ID NO: 58), ENODL3-4 BoC2 (SEQ ID NO:52), ENODL3-4 BoC1 (SEQ ID NO: 53), ENODL3-4 BrA1 (SEQ ID NO: 55), ENODL3-4 BrA2 (SEQ ID NO: 54). Conserved motifs are underlined and numbered. Motif 1 has the sequence of SEQ ID NO: 38, motif 2 has the sequence gtgaaaaga, motif 3 has the sequence of SEQ ID NO: 39, motif 4 has the sequence of SEQ ID NO: 40, motif 5 has the sequence of SEQ ID NO: 41, motif 6 has the sequence tttgcayrt, motif 7 has the sequence of SEQ ID NO: 42, motif 8 has the sequence of SEQ ID NO: 43, motif 9 has the sequence of SEQ ID NO: 44, motif 10 has the sequence of SEQ ID NO: 45, motif 11 has the sequence of SEQ ID NO: 46, motif 12 has the sequence of SEQ ID NO: 47.

DETAILED DESCRIPTION

Figure 1:
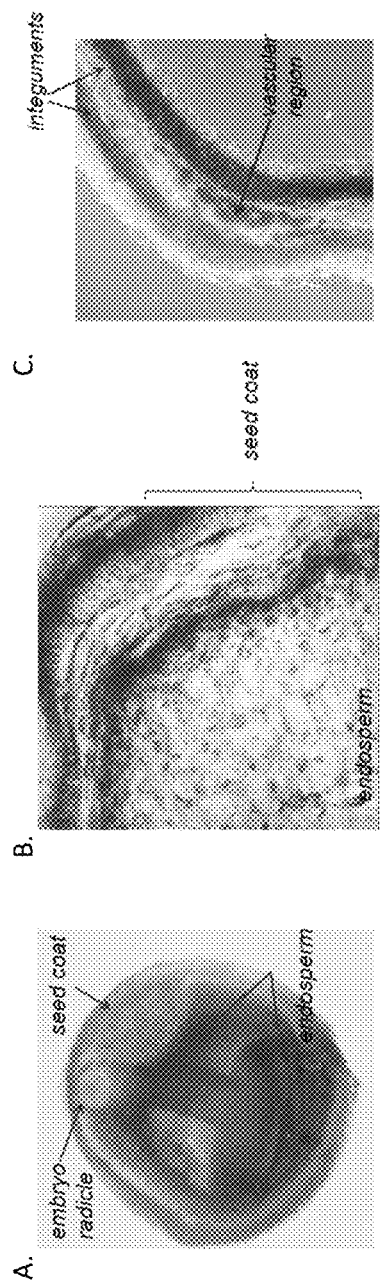
FIG. 1: Expression profile analysis in seeds carrying Penodl3-4BnC2::GUS. GUS labelling in the endosperm and seed coat at early stage (A, B) and at late stage (C).

The present invention is based on the observation that SEQ ID NOs: 2 to 13 have early stage seed-specific promoter activity and endosperm-preferential promoter activity in Brassica.

SEQ ID NOs: 2 to 13 depict the region upstream (i.e. located 5' upstream of) from the first ATG start codon of the ENODL3-4 BnC2, ENODL3-4 BnC1, ENODL3-4 BnA2, ENODL3-4 BnA1, ENODL3-4 BoC2, ENODL3-4 BoC1, ENODL3-4 BrA2, ENODL3-4 BrA1, ENODL3-4 BjB2, ENODL3-4 BjB1, ENODL3-4 BjA2, ENODL3-4 BjA1 respectively. Such a promoter region may be at least about 350 bp, at least about 400 bp, at least about 500 bp, at least about 600 bp, at least about 700 bp, at least about 800 bp, at least about 900 bp, or at least about 975 bp upstream of the first ATG start codon of the ENODL3-4 BnC2, ENODL3-4 BnC1, ENODL3-4 BnA2, ENODL3-4 BnA1, ENODL3-4 BoC2, ENODL3-4 BoC1, ENODL3-4 BrA2, ENODL3-4 BrA1, ENODL3-4 BjB2, ENODL3-4 BjB1, ENODL3-4 BjA2, ENODL3-4 BjA1 transcripts.

ENODL3-4 BnC2, ENODL3-4 BnC1, ENODL3-4 BnA2 and ENODL3-4 BnA1 are the 4 copies present in *Brassica napus* of the orthologous gene to both the *Arabidopsis thaliana* Early Nodulation-Like 3 and Early Nodulation-Like 4 genes. ENODL3-4 BoC2 and ENODL3-4 BoC1 are the 2 copies present in *Brassica oleracea* of the orthologous gene to both the *Arabidopsis thaliana* Early Nodulation-Like 3 and Early Nodulation-Like 4 genes. ENODL3-4 BrA2 and ENODL3-4 BrA1 are the 2 copies present in *Brassica rapa* of the orthologous gene to both the *Arabidopsis thaliana* Early Nodulation-Like 3 and Early Nodulation-Like 4 genes. ENODL3-4 BjB2, ENODL3-4 BjB1, ENODL3-4 BjA2 and ENODL3-4 BjA1 are the 4 copies present in *Brassica juncea* of the orthologous gene to both the *Arabidopsis thaliana* Early Nodulation-Like 3 and Early Nodulation-Like 4 genes. The early nodulin-like gene family is a large plant-specific family of genes initially identified as expressed in legume during the early stages of root nodule development. However, expression analyses in *Arabidopsis thaliana* and *Brassica rapa* unraveled the diversity of expression pattern of the different ENODL genes (Mashiguchi et al. 2009 Biosci. Biotechnol. Biochem. 73(11):2452-2459, Li et al. 2013 Mol Genet Genomics 288:1-20). In both studies, the ENODL3/ENODL4 genes were characterized as expressed specifically in flowers but absent from seeds. In contrast Huang et al. identified the *Brassica napus* orthologs of AtENODL4 as being expressed in the endosperm between 8 and 14 days after flowering, period covering the development of the embryo from the globular-shape stage until entry into the cotyledon stage (Huang et al. 2009 BMC Genomics 10:256). Furthermore, the Japanese patent application No. 2003-159071 describes an ortholog of AtENODL3/AtENODL4 from *Brassica napus* as being very early stage embryo-specifically expressed, from the fertilized egg until the heart-shaped embryo developmental stage.

In one aspect, the invention provides an isolated nucleic acid comprising early stage seed-specific and endosperm-preferential promoter activity selected from the group consisting of (a) a nucleic acid comprising a nucleotide sequence of any one of SEQ ID NOs: 2 to 13 or a functional fragment thereof; and (b) a nucleic acid comprising a nucleotide sequence having at least 95% sequence identity to anyone of SEQ ID NOs: 2 to 13, or a functional fragment thereof.

The nucleic acid comprising the early stage seed-specific and endosperm-preferential promoter activity according to the invention may also be comprised in a larger DNA molecule.

"Seed-specific promoter activity" in the context of this invention means the promoter activity is at least 10 times, or at least 20 times, or at least 50 times, or at least 100 times, or at least 200 times, or at least 500 times or even at least 1000 times higher than in other tissues. In other words, in seed-specific promoter activity, transcription of the nucleic acid operably linked to the promoter of the invention in the seeds is at least 10 times, or at least 20 times, or at least 50 times, or at least 100 times, or at least 200 times, or at least 500 times or even at least 1000 times higher than in other tissues. In other words, the seed-specific promoter drives seed-specific expression of the nucleic acid operably linked to the seed-specific promoter.

"Early stage seed" development in the context of this invention refers to seeds in which the embryo developmental stage ranges from early cotyledon-stage "walking stick" to the curled cotyledon stage. These developmental stages are reached between 14 and 25 days after flowering.

"Seed-specific promoter activity" encompasses "endosperm-preferential promoter activity".

"Endosperm-preferential promoter activity" in the context of this invention means the promoter activity is at least 2 times, or at least 5 times, or at least 10 times, or at least 20 times or even at least 100 times higher in endosperm tissues than in other seed tissues. In other words, in endosperm-preferential promoter activity, transcription of the nucleic acid operably linked to the promoter of the invention in the endosperm is at least 2 times, or at least 5 times, or at least 10 times, or at least 20 times or even at least 100 times higher than in other seed tissues. In other words, the endosperm-preferential promoter drives endosperm-preferential expression of the nucleic acid operably linked to the endosperm preferential promoter.

The phrase "operably linked" refers to the functional spatial arrangement of two or more nucleic acid regions or nucleic acid sequences. For example, a promoter region may be positioned relative to a nucleic acid sequence such that transcription of a nucleic acid sequence is directed by the promoter region. Thus, a promoter region is "operably linked" to the nucleic acid sequence. "Functionally linked" is an equivalent term.

The phrases "DNA", "DNA sequence," "nucleic acid sequence," "nucleic acid molecule" "nucleotide sequence" and "nucleic acid" refer to a physical structure comprising an orderly arrangement of nucleotides. The DNA sequence or nucleotide sequence may be contained within a larger nucleotide molecule, vector, or the like. In addition, the orderly arrangement of nucleic acids in these sequences may be depicted in the form of a sequence listing, figure, table, electronic medium, or the like.

As used herein, "promoter" means a region of DNA sequence that is essential for the initiation of transcription of DNA, resulting in the generation of an RNA molecule that is complementary to the transcribed DNA; this region may also be referred to as a "5' regulatory region." Promoters are usually located upstream of the coding sequence to be transcribed and have regions that act as binding sites for RNA polymerase II and other proteins such as transcription factors (trans-acting protein factors that regulate transcription) to initiate transcription of an operably linked gene. Promoters may themselves contain sub-elements (i.e. promoter motifs) such as cis-elements or enhancer domains that regulate the transcription of operably linked genes. The promoters of this invention may be altered to contain "enhancer DNA" to assist in elevating gene expression. As is known in the art, certain DNA elements can be used to enhance the transcription of DNA. These enhancers often are found 5' to the start of transcription in a promoter that functions in eukaryotic cells, but can often be inserted upstream (5') or downstream (3') to the coding sequence. In some instances, these 5' enhancer DNA elements are introns. Among the introns that are useful as enhancer DNA are the 5' introns from the rice actin 1 gene (see U.S. Pat. No. 5,641,876), the rice actin 2 gene, the maize alcohol dehydrogenase gene, the maize heat shock protein 70 gene (see U.S. Pat. No. 5,593,874), the maize shrunken 1 gene, the light sensitive 1 gene of *Solanum tuberosum*, the *Arabidopsis histon* 4 intron and the heat shock protein 70 gene of *Petunia hybrida* (see U.S. Pat. No. 5,659,122). Thus, as contemplated herein, a promoter or promoter region includes variations of promoters derived by inserting or deleting regulatory regions, subjecting the promoter to random or site-directed mutagenesis, etc. The activity or strength of a promoter may be measured in terms of the amounts of RNA it produces, or the amount of protein accumulation in a cell or tissue, relative to a promoter whose transcriptional activity has been previously assessed or relative to a promoter driving the expression of a housekeeping gene. A promoter as used herein may thus include sequences downstream of the transcription start, such as sequences coding the 5' untranslated region (5' UTR) of the RNA, introns located downstream of the transcription start, or even sequences encoding the protein.

A functional promoter fragment according to the invention may comprise the nucleotide sequence of any one of SEQ ID NOs: 2 to 13 from the nucleotide at position 626 to the nucleotide at position 975, or the nucleotide sequence of any one of SEQ ID NOs: 2 to 13 from the nucleotide at position 576 to the nucleotide at position 975 or the nucleotide sequence of any one of SEQ ID NOs: 2 to 13 from the nucleotide at position 476 to the nucleotide at position 975, or the nucleotide sequence of any one of SEQ ID NOs: 2 to 13 from the nucleotide at position 376 to the nucleotide at position 975, or the nucleotide sequence of any one of SEQ ID NOs: 2 to 13 from the nucleotide at position 276 to the nucleotide at position 975 or the nucleotide sequence of any one of SEQ ID NOs: 2 to 13 from the nucleotide at position 176 to the nucleotide at position 975 or the nucleotide sequence of any one of SEQ ID NOs: 2 to 13 from the nucleotide at position 76 to the nucleotide at position 975 or the nucleotide sequence of any one of SEQ ID NOs: 2 to 13 from the nucleotide at position 1 to the nucleotide at position 975.

Promoter activity for a functional promoter fragment in seeds may be determined by those skilled in the art, for example using analysis of RNA accumulation produced from the nucleic acid which is operably linked to the promoter as described herein, whereby the nucleic acid which is operably linked to the promoter can be the nucleic acid which is naturally linked to the promoter, i.e. the endogenous gene of which expression is driven by the promoter.

The early stage seed-specific expression capacity and the endosperm-preferential expression capacity of the identified or generated fragments of the promoters of the invention can be conveniently tested by determining levels of the transcript of which expression is naturally driven by the promoter of the invention, i.e. endogenous transcript levels, such as, for example, using the methods as described herein in the Examples. Further, the early stage seed-specific and endosperm-preferential expression capacity of the identified or generated fragments of the promoters of the invention can be conveniently tested by operably linking such DNA molecules to a nucleotide sequence encoding an easy scorable marker, e.g. a beta-glucuronidase gene, introducing such a chimeric gene into a plant and analyzing the expression pattern of the marker in seeds at different developmental stages as compared with the expression pattern of the marker in other parts of the plant or in seeds at other developmental stages. Other candidates for a marker (or a reporter gene) are chloramphenicol acetyl transferase (CAT) and proteins with fluorescent properties, such as green fluorescent protein (GFP) from *Aequora victoria*, or proteins with luminescent properties such as the *Renilla* luciferase or the bacterial lux operon. To define a minimal promoter region, a DNA segment representing the promoter region is removed from the 5' region of the gene of interest and operably linked to the coding sequence of a marker (reporter) gene by recombinant DNA techniques well known to the art. The reporter gene is operably linked downstream of the promoter, so that transcripts initiating at the promoter proceed through the reporter gene. Reporter genes generally encode proteins, which are easily measured, including, but not limited to, chloramphenicol acetyl transferase (CAT), beta-glucuronidase (GUS), green fluorescent protein (GFP), beta-galactosidase (beta-GAL), and luciferase. The expression cassette containing the reporter gene under the control of the promoter can be introduced into an appropriate cell type by transfection techniques well known to the art. To assay for the reporter protein, cell lysates are prepared and appropriate assays, which are well known in the art, for the reporter protein are performed. For example, if CAT were the reporter gene of choice, the lysates from cells transfected with constructs containing CAT under the control of a promoter under study are mixed with isotopically labeled chloramphenicol and acetyl-coenzyme A (acetyl-CoA). The CAT enzyme transfers the acetyl group from acetyl-CoA to the 2- or 3-position of chloramphenicol. The reaction is monitored by thin-layer chromatography, which separates acetylated chloramphenicol from unreacted material. The reaction products are then visualized by autoradiography. The level of enzyme activity corresponds to the amount of enzyme that was made, which in turn reveals the level of expression and the early stage seed-specific and endosperm preferential functionality from the promoter or promoter fragment of interest. This level of expression can also be compared to other promoters to determine the relative strength of the promoter under study. Once activity and functionality is confirmed, additional mutational and/or deletion analyses may be employed to determine the minimal region and/or sequences required to initiate transcription. Thus, sequences can be deleted at the 5' end of the promoter region and/or at the 3' end of the promoter region, and nucleotide substitutions introduced. These constructs are then again introduced in cells and their activity and/or functionality determined.

The activity or strength of a promoter may be measured in terms of the amount of mRNA or protein accumulation it specifically produces, relative to the total amount of mRNA or protein. The promoter preferably expresses an operably linked nucleic acid sequence at a level greater than about 0.01%, about 0.02%, more preferably greater than about 0.05% of the total mRNA. Alternatively, the activity or strength of a promoter may be expressed relative to a well-characterized promoter (for which transcriptional activity was previously assessed).

It will herein further be clear that equivalent early stage seed-specific and endosperm-preferential promoters can be isolated from other plants. To this end, equivalent promoters can be isolated using the coding sequences of the genes driven by the promoters of any one of SEQ ID NOs: 2 to 13 to screen a genomic library (e.g. by hybridization or in silico) of a crop of interest. When sufficient identity between the coding sequences is obtained (for example, higher than 80% identity) then promoter regions can be isolated upstream of the orthologous genes.

Suitable to the invention are nucleic acids comprising early stage seed-specific and endosperm preferential promoter activity which comprise a nucleotide sequence having at least 40%, at least 50%, or at least 60%, or at least 70%, or at least 80%, or at least 85%, or at least 90%, or at least 95%, or at least 98% sequence identity to the herein described promoters and promoter regions or functional fragments thereof and are also referred to as variants. The term "variant" with respect to the transcription regulating nucleotide sequences SEQ ID NOs: 2 to 13 of the invention is intended to mean substantially similar sequences. Naturally occurring allelic variants such as these can be identified with the use of well-known molecular biology techniques, as, for example, with polymerase chain reaction (PCR) as herein outlined before. Variant nucleotide sequences also include synthetically derived nucleotide sequences, such as those generated, for example, by using site-directed mutagenesis of any one of SEQ ID NOs: 2 to 13. Generally, nucleotide sequence variants of the invention will have at least 40%, 50%, 60%, to 70%, e.g., preferably 71%, 72%, 73%, 74%, 75%, 76%, 77%, 78%, to 79%, generally at least 80%, e.g., 81% to 84%, at least 85%, e.g., 86%, 87%, 88%, 89%, 90%, 91%, 92%, 93%, 94%, 95%, 96%, 97%, to 98% and 99% nucleotide sequence identity to the native (wild type or endogenous) nucleotide sequence or a functional fragment thereof. Derivatives of the DNA molecules disclosed herein may include, but are not limited to, deletions of sequence, single or multiple point mutations, alterations at a particular restriction enzyme site, addition of functional elements, or other means of molecular modification which may enhance, or otherwise alter promoter expression. Techniques for obtaining such derivatives are well-known in the art (see, for example, J. F. Sambrook, D. W. Russell, and N. Irwin (2000) Molecular Cloning: A Laboratory Manual, 3$^{rd}$ edition Volumes 1, 2, and 3. Cold Spring Harbor Laboratory Press). For example, one of ordinary skill in the art may delimit the functional elements within the promoters disclosed herein and delete any non-essential elements. Functional elements may be modified or combined to increase the utility or expression of the sequences of the invention for any particular application. Those of skill in the art are familiar with the standard resource materials that describe specific conditions and procedures for the construction, manipulation, and isolation of macromolecules (e.g., DNA molecules, plasmids, etc.), as well as the generation of recombinant organisms and the screening and isolation of DNA molecules. As used herein, the term "percent sequence identity" refers to the percentage of identical nucleotides between two segments of a window of optimally aligned DNA. Optimal alignment of sequences for aligning a comparison window are well-known to those skilled in the art and may be conducted by tools such as the local homology algorithm of Smith and Waterman (Waterman, M. S. Introduction to Computational Biology: Maps, sequences and genomes. Chapman & Hall. London (1995), the homology alignment algorithm of Needleman and Wunsch (J. Mol. Biol., 48:443-453 (1970), the search for similarity method of Pearson and Lipman (Proc. Natl. Acad. Sci., 85:2444 (1988), and preferably by computerized implementations of these algorithms such as GAP, BESTFIT, FASTA, and TFASTA available as part of the GCG (Registered Trade Mark), Wisconsin Package (Registered Trade Mark from Accelrys Inc., San Diego, Calif.). An "identity fraction" for aligned segments of a test sequence and a reference sequence is the number of identical components that are shared by the two aligned sequences divided by the total number of components in the reference sequence segment, i.e., the entire reference sequence or a smaller defined part of the reference sequence. Percent sequence identity is represented as the identity fraction times 100. The comparison of one or more DNA sequences may be to a full-length DNA sequence or a portion thereof, or to a longer DNA sequence.

A nucleic acid comprising a nucleotide sequence having at least 95% sequence identity to any one of SEQ ID NOs: 2 to 13 can thus be a nucleic acid comprising a nucleotide sequence having at least at least 95%, or at least 96%, or at least 97%, or at least 98%, or at least 99%, or 100% sequence identity to anyone of SEQ ID NOs: 2 to 13.

A "functional fragment" of a nucleic acid comprising early stage seed-specific and endosperm-preferential promoter denotes a nucleic acid comprising a stretch of the nucleic acid sequences of any one of SEQ ID NOs: 2 to 13, or of the nucleic acid having at least 95% sequence identity to any one of SEQ ID NOs: 2 to 13 which still exerts the desired function, i.e. which has early stage seed-specific and endosperm preferential promoter activity. Assays for determining early stage seed-specific and endosperm-preferential promoter activity are provided herein. Preferably, the functional fragment of the early stage seed-specific and endosperm-preferential promoter contains the conserved promoter motifs, such as, for example, conserved promoter motifs as described in DoOP (doop.abc.hu, databases of Orthologous Promoters, Barta E. et al (2005) *Nucleic Acids Research* Vol. 33, D86-D90). A functional fragment may be a fragment of at least about 350 bp, at least about 400 bp, at least about 500 bp, at least about 600 bp, at least about 700 bp, at least about 800 bp, at least about 900 bp from the translation start site.

A nucleic acid comprising the nucleotide sequence of any one of SEQ ID NOs: 2 to 13 which further comprises insertion, deletion, substitution of at least 1 nucleotide up to 20 nucleotides, at least 1 nucleotide up to 15 nucleotides, at least 1 nucleotide up to 10 nucleotides, at least 1 nucleotide up to 5 nucleotides, at least 1 nucleotide up to 4 nucleotides, at least 1 nucleotide up to 3 nucleotides, or even at least 1 nucleotide up to 2 nucleotides may cover at least about 350 bp, at least about 400 bp, at least about 500 bp, at least about 600 bp, at least about 700 bp, at least about 800 bp, at least about 900 bp from the translation start site.

A number of consensus elements (sequence motifs) were identified on the promoter sequence disclosed herein.

Variants of the promoter described herein include those which comprise the identified motifs—motif 1 (SEQ ID NO: 38), motif 2 (gtgaaaaga), motif 3 (SEQ ID NO: 39), motif 4 (SEQ ID NO: 40), motif 5 (SEQ ID NO: 41), motif 6 (tttgcayrt), motif 7 (SEQ ID NO: 42), motif 8 (SEQ ID NO: 43), motif 9 (SEQ ID NO: 44), motif 10 (SEQ ID NO: 45), motif 11 (SEQ ID NO: 46) and/or motif 12 (SEQ ID NO: 47)—but have otherwise been modified to delete nucleotide stretches within the sequence which are not needed for the promoter to be functional in seed-specific and endosperm-preferential manner. For example, any nucleotide stretch located between the motifs and/or between the translational start and the first motif may be at least partially deleted to result in a shorter nucleotide sequence than the about 975 bp sequence of anyone of SEQ ID NO: 2 to SEQ ID NO: 13.

"Isolated nucleic acid", used interchangeably with "isolated DNA" as used herein refers to a nucleic acid not occurring in its natural genomic context, irrespective of its length and sequence. Isolated DNA can, for example, refer to DNA which is physically separated from the genomic context, such as a fragment of genomic DNA. Isolated DNA can also be an artificially produced DNA, such as a chemically synthesized DNA, or such as DNA produced via amplification reactions, such as polymerase chain reaction (PCR) well-known in the art. Isolated DNA can further refer to DNA present in a context of DNA in which it does not occur naturally. For example, isolated DNA can refer to a piece of DNA present in a plasmid. Further, the isolated DNA can refer to a piece of DNA present in another chromosomal context than the context in which it occurs naturally, such as for example at another position in the genome than the natural position, in the genome of another species than the species in which it occurs naturally, or in an artificial chromosome.

A further embodiment provides a recombinant gene comprising the nucleic acid according to the invention operably linked to a heterologous nucleic acid sequence encoding an expression product of interest, and optionally a transcription termination and polyadenylation sequence, preferably a transcription termination and polyadenylation region functional in plant cells. In a further embodiment, said expression product of interest an RNA capable of modulating the expression of a gene or is a protein.

The term "expression product" refers to a product of transcription. Said expression product can be the transcribed RNA. It is understood that the RNA which is produced is a biologically active RNA. Said expression product can also be a peptide, a polypeptide, or a protein, when said biologically active RNA is an mRNA and said protein is produced by translation of said mRNA.

Alternatively, the heterologous nucleic acid, operably linked to the promoters of the invention, may also code for an RNA capable of modulating the expression of a gene. Said RNA capable of modulating the expression of a gene can be an RNA which reduces expression of a gene. Said RNA can reduce the expression of a gene for example through the mechanism of RNA-mediated gene silencing.

Said RNA capable of modulating the expression of a gene can be a silencing RNA down-regulating expression of a target gene. As used herein, "silencing RNA" or "silencing RNA molecule" refers to any RNA molecule, which upon introduction into a plant cell, reduces the expression of a target gene. Such silencing RNA may e.g. be so-called "antisense RNA", whereby the RNA molecule comprises a sequence of at least 20 consecutive nucleotides having 95% sequence identity to the complement of the sequence of the target nucleic acid, preferably the coding sequence of the target gene. However, antisense RNA may also be directed to regulatory sequences of target genes, including the promoter sequences and transcription termination and polyadenylation signals. Silencing RNA further includes so-called "sense RNA" whereby the RNA molecule comprises a sequence of at least 20 consecutive nucleotides having 95% sequence identity to the sequence of the target nucleic acid. Other silencing RNA may be "unpolyadenylated RNA" comprising at least 20 consecutive nucleotides having 95% sequence identity to the complement of the sequence of the target nucleic acid, such as described in WO01/12824 or U.S. Pat. No. 6,423,885 (both documents herein incorporated by reference). Yet another type of silencing RNA is an RNA molecule as described in WO03/076619 (herein incorporated by reference) comprising at least 20 consecutive nucleotides having 95% sequence identity to the sequence of the target nucleic acid or the complement thereof, and further comprising a largely-double stranded region as described in WO03/076619 (including largely double stranded regions comprising a nuclear localization signal from a viroid of the Potato spindle tuber viroid-type or comprising CUG trinucleotide repeats). Silencing RNA may also be double stranded RNA comprising a sense and antisense strand as herein defined, wherein the sense and antisense strand are capable of base-pairing with each other to form a double stranded RNA region (preferably the said at least 20 consecutive nucleotides of the sense and antisense RNA are complementary to each other). The sense and antisense region may also be present within one RNA molecule such that a hairpin RNA (hpRNA) can be formed when the sense and antisense region form a double stranded RNA region. hpRNA is well-known within the art (see e.g WO99/53050, herein incorporated by reference). The hpRNA may be classified as long hpRNA, having long, sense and antisense regions which can be largely complementary, but need not be entirely complementary (typically larger than about 200 bp, ranging between 200 and 1000 bp). hpRNA can also be rather small ranging in size from about 30 to about 42 bp, but not much longer than 94 bp (see WO04/073390, herein incorporated by reference). Silencing RNA may also be artificial micro-RNA molecules as described e.g. in WO2005/052170, WO2005/047505 or US 2005/0144667, or ta-siRNAs as described in WO2006/074400 (all documents incorporated herein by reference). Said RNA capable of modulating the expression of a gene can also be an RNA ribozyme.

Said RNA capable of modulating the expression of a gene can modulate, preferably down-regulate, the expression of other genes (i.e. target genes) comprised within the seeds or even of genes present within a pathogen or pest that feeds upon the seeds of the transgenic plant such as a virus, fungus, insect, bacteria.

The nucleic acid sequence heterologous to the promoters according to the invention may generally be any nucleic acid sequence effecting increased, altered (e.g. in a different organ) or reduced level of transcription of a gene for which such expression modulation is desired. The nucleic acid sequence can for example encode a protein of interest. Exemplary genes for which an increased or reduced level of transcription may be desired in the seeds are e.g. nucleic acids that can provide an agriculturally or industrially important feature in seeds. Suitable heterologous nucleic acid sequences of interest include nucleic acids modulating expression of genes conferring resistance to diseases, stress tolerance genes, genes involved in at different stages of fatty acid biosynthesis or degradation, in acyl editing, in storage compound storage or breakdown, genes encoding epoxidases, hydroxylases, cytochrome P450 mono-oxygenases, desaturases, tocopherol biosynthetic enzymes, carotenoid biosynthesis enzymes, amino acid biosynthetic enzymes, steroid pathway enzymes, starch branching enzymes, genes encoding proteins involved in starch synthesis, glycolysis, carbon metabolism, oxidative pentose phosphate cycle, protein synthesis, organelle organization and biogenesis, DNA metabolism, DNA replication, cell cycle, cell organization and biogenesis, cell proliferation, chromosome organization and biogenesis, microtubule-based processes, microtubule-based movement, cytoskeleton-dependent intracellular transport, cytoskeleton organization and biogenesis, chromatin assembly or disassembly, DNA-dependent DNA replication, chromosome organization and biogenesis, DNA packaging, establishment and/or maintenance of chromatin architecture, regulation of progression through the cell cycle, regulation of the cell cycle, nucleobase, nucleoside, nucleotide and nucleic acid metabolism, chromatin assembly, macromolecule biosynthesis, intracellular transport, establishment of cellular localization, cellular localization, nucleosome assembly, macromolecule metabolism, or M-phase; genes involved in secondary metabolism or genes involved in seed and/or seed coat architecture.

Genes involved in the fatty acid biosynthesis or degradation include but are not limited to genes encoding an acyl-CoA synthetase, a glycerol-phosphate acyltransferase, an O-acyltransferase, a lyso-phosphatidic acid acyltransferase, a phosphatidic acid phosphatase, a diacylglycerol acyltransferase, an oleate desaturases, a linoleate desaturases, an acyl-CoA hydroxylase, an acyl-lipid hydroxylase, a fatty acid epoxidase, a phospholipid:sterol acyltransferase, a phospholipid:diacylglycerol acyltransferase, a diacylglycerol transacylase, a lysophosphatidylcholine acyltransferase, a phosphatidylcholine:diacylglycerol cholinephosphotransferase, an acyl-CoA elongase, an acyl-lipid elongase, a phosphatidylglycerol-phosphate synthetase, a phosphatidylglycerol-phosphate phosphatase, a CDP-diacylglycerol synthetase, a phosphatidylinositol synthase, a phosphatidylserine synthase, a choline kinase, an ethanolamine kinase, a CDP-choline synthetase, a CDP-ethanolamine synthetase, a phosphatidylserine decarboxylase, a lipoxygenase, a phospholipase, a lipase, a carboxylesterase, a fatty alcohol reductase, a wax ester synthase, a bifunctional acyltranferases/wax synthase, a ketoacyl-CoA synthase, a ketoacyl-CoA reductase, a hydroxylacyl-CoA dehydrase, an enoyl-CoA reductase, an alcohol-forming fatty acyl-CoA reductase, an aldehyde-forming fatty acyl-CoA reductase, an aldehyde decarbonylase, a wax ester hydrolase, a glycerol-3-P-dehydrogenase, a CDP-choline:1,2-diacylglycerol cholinephosphotransferase, an oxidase, a ketosphinganine reductase, a ceramide synthase, an acylglycerophosphorylcholine acyltransferase, an acylglycerol-phosphate acyltransferase, a phosphoethanolamine N-methyltransferase, a ceramide sphingobase desaturase, a glucosylceramide synthase, a acyl-ceramide synthase, a triacylglycerol lipase, a monoacylglycerol lipase, an acyl-CoA oxidase, an hydroxyacyl-CoA dehydrogenase, a dienoyl-CoA reductase, a fatty acid omega-alcohol oxidase, a monoacylglycerol lipase, an acyl-CoA oxidase, a hydroxyacyl-CoA dehydrogenase, a dienoyl-CoA reductase, a fatty acid omega-alcohol oxidase, a fatty acid/acyl-CoA transporter, a acyl-CoA dehydrogenase, a diacylglycerol-phosphate kinase, a lysophosphatidic acic phosphatase, a peroxygenase; a Δ4-desaturase; a Δ5-desaturase, a Δ6-desaturase; a Δ9-desaturase, a Δ12-desaturase or a Δ15-desaturase.

Genes involved in cell proliferation include but are not limited to genes encoding Da1 (Li et al., 2008, Genes Dev 22:1331, WO2015/067943), Da2, EOD1 or EOD3 (WO2015/022192, PCT/GB2013/050072).

A "transcription termination and polyadenylation region" as used herein is a sequence that drives the cleavage of the nascent RNA, whereafter a poly(A) tail is added at the resulting RNA 3' end, functional in plant cells. Transcription termination and polyadenylation signals functional in plant cells include, but are not limited to, 3'nos, 3'35S, 3'his and 3'g7.

The term "protein" interchangeably used with the term "polypeptide" as used herein describes a group of molecules consisting of more than 30 amino acids, whereas the term "peptide" describes molecules consisting of up to 30 amino acids. Proteins and peptides may further form dimers, trimers and higher oligomers, i.e. consisting of more than one (poly)peptide molecule. Protein or peptide molecules forming such dimers, trimers etc. may be identical or non-identical. The corresponding higher order structures are, consequently, termed homo- or heterodimers, homo- or heterotrimers etc. The terms "protein" and "peptide" also refer to naturally modified proteins or peptides wherein the modification is effected e.g. by glycosylation, acetylation, phosphorylation and the like. Such modifications are well known in the art.

The term "heterologous" refers to the relationship between two or more nucleic acid or protein sequences that are derived from different sources. For example, a promoter is heterologous with respect to an operably linked DNA region, such as a coding sequence if such a combination is not normally found in nature. In addition, a particular sequence may be "heterologous" with respect to a cell or organism into which it is inserted (i.e. does not naturally occur in that particular cell or organism).

The term "recombinant gene" refers to any gene that contains: a) DNA sequences, including regulatory and coding sequences that are not found together in nature, or b) sequences encoding parts of proteins not naturally adjoined, or c) parts of promoters that are not naturally adjoined. Accordingly, a recombinant gene may comprise regulatory sequences and coding sequences that are derived from different sources, or comprise regulatory sequences, and coding sequences derived from the same source, but arranged in a manner different from that found in nature.

Any of the promoters and heterologous nucleic acid sequences described above may be provided in a recombinant vector. A recombinant vector typically comprises, in a 5' to 3' orientation: a promoter to direct the transcription of a nucleic acid sequence and a nucleic acid sequence. The recombinant vector may further comprise a 3' transcriptional terminator, a 3' polyadenylation signal, other untranslated nucleic acid sequences, transit and targeting nucleic acid sequences, selectable markers, enhancers, and operators, as desired. The wording "5' UTR" refers to the untranslated region of DNA upstream, or 5' of the coding region of a gene and "3' UTR" refers to the untranslated region of DNA downstream, or 3' of the coding region of a gene. Means for preparing recombinant vectors are well known in the art. Methods for making recombinant vectors particularly suited to plant transformation are described in U.S. Pat. Nos. 4,971,908, 4,940,835, 4,769,061 and 4,757,011. Typical vectors useful for expression of nucleic acids in higher plants are well known in the art and include vectors derived from the tumor-inducing (Ti) plasmid of *Agrobacterium tumefaciens*. One or more additional promoters may also be provided in the recombinant vector. These promoters may be operably linked, for example, without limitation, to any of the nucleic acid sequences described above. Alternatively, the promoters may be operably linked to other nucleic acid sequences, such as those encoding transit peptides, selectable marker proteins, or antisense sequences. These additional promoters may be selected on the basis of the cell type into which the vector will be inserted. Also, promoters which function in bacteria, yeast, and plants are all well taught in the art. The additional promoters may also be selected on the basis of their regulatory features. Examples of such features include enhancement of transcriptional activity, inducibility, tissue specificity, and developmental stage-specificity.

The recombinant vector may also contain one or more additional nucleic acid sequences. These additional nucleic acid sequences may generally be any sequences suitable for use in a recombinant vector. Such nucleic acid sequences include, without limitation, any of the nucleic acid sequences, and modified forms thereof, described above. The additional structural nucleic acid sequences may also be operably linked to any of the above described promoters. The one or more structural nucleic acid sequences may each be operably linked to separate promoters. Alternatively, the structural nucleic acid sequences may be operably linked to a single promoter (i.e., a single operon).

Yet another embodiment provides a host cell, such as an *E. coli* cell, an *Agrobacterium* cell, a yeast cell, or a plant cell, comprising the isolated nucleic acid according to the invention, or the recombinant gene according to the invention.

Other nucleic acid sequences may also be introduced into the host cell along with the promoter and structural nucleic acid sequence, e. g. also in connection with the vector of the invention. These other sequences may include 3' transcriptional terminators, 3' polyadenylation signals, other untranslated nucleic acid sequences, transit or targeting sequences, selectable markers, enhancers, and operators. Preferred nucleic acid sequences of the present invention, including recombinant vectors, structural nucleic acid sequences, promoters, and other regulatory elements, are described above.

In further embodiments, a plant and a plant cell are provided comprising the recombinant gene according to the invention. In yet a further embodiment, a plant is provided comprising at least two recombinant genes according to the invention, wherein the nucleic acid comprising early stage seed-specific and endosperm preferential promoter activity according to the invention and, optionally, the heterologous nucleic acid sequence operably linked thereto, are different in each recombinant gene. Yet a further embodiment provides seeds obtainable from the plant according to the invention. In another embodiment, the plants or seeds according to the invention are seed crop plants or seeds.

The plant cell or plant comprising the recombinant gene according to the invention can be a plant cell or a plant comprising a recombinant gene of which either the promoter, or the heterologous nucleic acid sequence operably linked to said promoter, are heterologous with respect to the plant cell. Such plant cells or plants may be transgenic plant in which the recombinant gene is introduced via transformation. Alternatively, the plant cell of plant may comprise the promoter according to the invention derived from the same species operably linked to a nucleic acid which is also derived from the same species, i.e. neither the promoter nor the operably linked nucleic acid is heterologous with respect to the plant cell, but the promoter is operably linked to a nucleic acid to which it is not linked in nature. A recombinant gene can be introduced in the plant or plant cell via transformation, such that both the promoter and the operably linked nucleotide are at a position in the genome in which they do not occur naturally. Alternatively, the promoter according to the invention can be integrated in a targeted manner in the genome of the plant or plant cell upstream of an endogenous nucleic acid encoding an expression product of interest, i.e. to modulate the expression pattern of an endogenous gene. The promoter that is integrated in a targeted manner upstream of an endogenous nucleic acid can be integrated in cells of a plant species from which it is originally derived, or in cells of a heterologous plant species. Alternatively, a heterologous nucleic acid can be integrated in a targeted manner in the genome of the plant or plant cell downstream of the promoter according to the invention, such that said heterologous nucleic acid is expressed seed-specifically and endosperm-preferentially. Said heterologous nucleic acid is a nucleic acid which is heterologous with respect to the promoter, i.e. the combination of the promoter with said heterologous nucleic acid is not normally found in nature. Said heterologous nucleic acid may be a nucleic acid which is heterologous to said plant species in which it is inserted, but it may also naturally occur in said plant species at a different location in the plant genome. Said promoter or said heterologous nucleic acid can be integrated in a targeted manner in the plant genome via targeted sequence insertion, using, for example, the methods as described in WO2005/049842.

Plants comprising at least two recombinant genes according to the invention wherein the nucleic acid comprising seed-specific and endosperm-preferential promoter activity is different in each recombinant gene are, for example, plants comprising a first recombinant gene comprising a nucleotide sequence having at least 95% sequence identity to SEQ ID NO: 2 or a functional fragment thereof, and a second recombinant gene comprising a nucleotide sequence having at least 95% sequence identity to any one of SEQ ID NO: 3 to SEQ ID NO: 13 or a functional fragment thereof. It will be clear that, when the first recombinant gene comprises a nucleotide sequence having at least 95% sequence identity to SEQ ID NO: x or a functional fragment thereof, wherein SEQ ID NO: x is selected from any one of SEQ ID NO: 2 to SEQ ID NO: 13, the second recombinant gene may comprise a nucleotide sequence having at least 95% sequence identity to any one of the sequences according to the invention or a functional fragment thereof, except to SEQ ID NO: x. Said plants are suitable to express different genes with the same tissue-specificity, however without the negative features associated with the repeated use of one promoter, such as gene silencing or recombination of a vector comprising the recombinant genes. The at least two recombinant genes according to the invention may be present at one locus in the genome of said plant, and may be derived from the same transforming DNA molecule.

Plants according to the invention may comprise one or more recombinant genes according to the invention, but may in addition contain a recombinant gene comprising a nucleic acid comprising promoter activity which is preferential or specific to other plant tissues, such as apical meristem, flower buds, cotyledons, flowers, pods, roots, and leaves or other seed developmental stages, operably linked to a nucleic acid sequence encoding an expression product of interest. The recombinant gene according to the invention and the recombinant gene comprising a nucleic acid comprising another promoter activity may be present at one locus and may be derived from the same transforming DNA molecule.

Yet another embodiment provides a method of producing a transgenic plant comprising the steps of (a) introducing or providing the recombinant gene according to the invention to a plant cell to create transgenic cells; and (b) regenerating transgenic plants from said transgenic cell.

"Introducing" in connection with the present application relates to the placing of genetic information in a plant cell or plant by artificial means. This can be effected by any method known in the art for introducing RNA or DNA into plant cells, protoplasts, calli, roots, tubers, seeds, stems, leaves, seedlings, embryos, pollen and microspores, other plant tissues, or whole plants. "Introducing" also comprises stably integrating into the plant's genome. Introducing the recombinant gene can be performed by transformation.

The term "transformation" herein refers to the introduction (or transfer) of nucleic acid into a recipient host such as a plant or any plant parts or tissues including plant cells, protoplasts, calli, roots, tubers, seeds, stems, leaves, seedlings, embryos and pollen. Plants containing the transformed nucleic acid sequence are referred to as "transgenic plants". Transformed, transgenic and recombinant refer to a host organism such as a plant into which a heterologous nucleic acid molecule (e.g. an expression cassette or a recombinant vector) has been introduced. The nucleic acid can be stably integrated into the genome of the plant.

As used herein, the phrase "transgenic plant" refers to a plant having an introduced nucleic acid stably introduced into a genome of the plant, for example, the nuclear or plastid genomes. In other words, plants containing transformed nucleic acid sequence are referred to as "transgenic plants". Transgenic and recombinant refer to a host organism such as a plant to which a heterologous nucleic acid molecule (e.g. the promoter, the chimeric gene or the vector as described herein) has been introduced. The nucleic acid can be stably integrated into the genome of the plant.

Transformation methods are well known in the art and include *Agrobacterium*-mediated transformation. *Agrobacterium*-mediated transformation of cotton has been described e.g. in U.S. Pat. No. 5,004,863, in U.S. Pat. No. 6,483,013 and WO2000/71733. Plants may also be transformed by particle bombardment: Particles of gold or tungsten are coated with DNA and then shot into young plant cells or plant embryos. This method also allows transformation of plant plastids. Viral transformation (transduction) may be used for transient or stable expression of a gene, depending on the nature of the virus genome. The desired genetic material is packaged into a suitable plant virus and the modified virus is allowed to infect the plant. The progeny of the infected plants is virus free and also free of the inserted gene. Suitable methods for viral transformation are described or further detailed e. g. in WO 90/12107, WO 03/052108 or WO 2005/098004. Further suitable methods well-known in the art are microinjection, electroporation of intact cells, polyethyleneglycol-mediated protoplast transformation, electroporation of protoplasts, liposome-mediated transformation, silicon-whiskers mediated transformation etc. Said transgene may be stably integrated into the genome of said plant cell, resulting in a transformed plant cell. The transformed plant cells obtained in this way may then be regenerated into mature fertile transformed plants.

Further provided is a method of effecting early stage seed-specific and endosperm preferential expression of a nucleic acid comprising introducing the recombinant gene according to the invention into the genome of a plant, or providing the plant according to the invention. Also provided is a method for altering seed properties of a plant or to produce a commercially relevant product in a plant, comprising introducing the recombinant gene according to the invention into the genome of a plant, or providing the plant according to the invention. In another embodiment, said plant is a seed crop plant.

"Seed properties" as used herein are properties of the seed. Seed properties can, for example, be seed yield, seed storage compound production, seed compound accumulation, seed nutrient accumulation; seed micronutrient accumulation; seed storage compound quality, seed compound composition, seed quality, biotic stress tolerance such as disease tolerance, abiotic stress tolerance, herbicide tolerance, seed dormancy, seed imbibition, seed germination, seed vigor. Seed storage compounds can, for example, be seed oil, seed starch, or seed protein.

Seed properties may be modulated by modulating metabolic pathways, such as starch metabolism, sugar metabolism, inositol phosphate metabolism, glycolysis, amino acid biosynthesis, carbon metabolism, nucleotide metabolism, oxidative pentose phosphate cycle, fatty acid biosynthesis, protein synthesis, or phytate metabolism, and modulating secondary metabolism pathways. Another example is the methyl recycling metabolic activity impacting chromatin remodeling, phospholipid biosynthesis and cell wall lignification. Such metabolic pathways can be modulated by, for example, overexpressing or down-regulating a gene involved in one or more of the metabolic pathways using the early stage seed-specific and endosperm preferential promoter according to the invention.

Yield as used herein can comprise yield of the plant or plant part which is harvested, such as seed, including seed oil content, seed protein content, seed weight, seed number. Increased yield can be increased yield per plant, and increased yield per surface unit of cultivated land, such as yield per hectare. Yield can be increased by modulating, for example, by increasing seed size or oil content or indirectly by increasing the tolerance to biotic and abiotic stress conditions and decreasing seed abortion.

Quality as used herein can comprise quality of the seed or grain such as beneficial carbohydrate composition or level, beneficial amino acid composition or level, beneficial fatty acid composition or level, nutritional value, seed and fiber content.

Abiotic stress tolerance as used herein can comprise resistance to environmental stress factors such as drought, extreme (high or low) temperatures.

Biotic stress tolerance as used herein can comprise pest resistance, such as resistance or fungal, bacterial, bacterial or viral pathogens or insects.

Also provided is the use of the isolated nucleic acid according to the invention to regulate expression of an operably linked nucleic acid in a plant, and the use of the isolated nucleic acid according to the invention, or the recombinant gene according to the invention to alter seed properties of a plant or to produce a commercially relevant product in a plant. In a further embodiment, said plant is a trait as used herein refers to beneficial properties of the plant, such as commercially beneficial properties of a plant.

Also provided is the use of the isolated nucleic acid according to the invention to identify other nucleic acids comprising early stage seed-specific and endosperm preferential promoter activity.

The promoters according to the invention can further be used to create hybrid promoters, i.e. promoters containing (parts of) one or more of the promoters(s) of the current invention and (parts of) other promoter which can be newly identified or known in the art. Such hybrid promoters may have optimized tissue specificity or expression level.

Yet another embodiment provides a method of producing food, feed, or an industrial product comprising (a) obtaining the plant or a part thereof, according to the invention; and (b) preparing the food, feed or industrial product from the plant or part thereof. In another embodiment, said food or feed is oil, meal, grain, starch, flour or protein, or said industrial product is biofuel, fiber, industrial chemicals, a pharmaceutical or a nutraceutical.

A "seed crop" or "seed crop plant" as used herein is a crop grown for its seeds or material derived from the seeds. Examples of seed crops are rice, maize, wheat, barley, millet, rye, oats, camelina, crambe, *Linum*, castor bean, calendula, safflower, sunflower, soybean, cotton, or *Brassica* species, such as *Brassica napus, Brassica juncea, Brassica carinata, Brassica rapa, Brassica oleracea*, and *Brassica nigra*.

"Brassicaceae" or "Brassicaceae plant" as used herein refers to plants belonging to the family of Brassicaceae plants, also called Cruciferae or mustard family. Examples of Brassicaceae are, but are not limited to, *Brassica* species, such as *Brassica napus, Brassica oleracea, Brassica rapa, Brassica carinata, Brassica nigra*, and *Brassica juncea; Raphanus* species, such as *Raphanus caudatus, Raphanus raphanistrum*, and *Raphanus sativus; Matthiola* species; *Cheiranthus* species; *Camelina* species, such as *Camelina sativa; Crambe* species, such as *Crambe abyssinica* and *Crambe hispanica; Eruca* species, such as *Eruca vesicaria; Sinapis* species such as *Sinapis alba; Diplotaxis* species;

*Lepidium* species; *Nasturtium* species; *Orychophragmus* species; *Armoracia* species, *Eutrema* species; *Lepidium* species; and *Arabidopsis* species.

Said *Brassicaceae* plant can be a *Brassica* plant. "*Brassica* plant" refers to allotetraploid or amphidiploid *Brassica napus* (AACC, 2n=38), *Brassica juncea* (AABB, 2n=36), *Brassica carinata* (BBCC, 2n=34), or to diploid *Brassica rapa* (syn. *B. campestris*) (AA, 2n=20), *Brassica oleracea* (CC, 2n=18) or *Brassica nigra* (BB, 2n=16).

Crop plants of the *Brassica* species are, for example, *Brassica napus, Brassica juncea, Brassica carinata, Brassica rapa* (syn. *B. campestris*), *Brassica oleracea* or *Brassica nigra*.

The plants according to the invention may additionally contain an endogenous or a transgene, which confers herbicide resistance, such as the bar or pat gene, which confer resistance to glufosinate ammonium (Liberty®, Basta® or Ignite®) [EP 0 242 236 and EP 0 242 246 incorporated by reference]; or any modified EPSPS gene, such as the 2mEPSPS gene from maize [EPO 508 909 and EP 0 507 698 incorporated by reference], or glyphosate acetyltransferase, or glyphosate oxidoreductase, which confer resistance to glyphosate (RoundupReady®), or bromoxynitril nitrilase to confer bromoxynitril tolerance, or any modified AHAS gene, which confers tolerance to sulfonylureas, imidazolinones, sulfonylaminocarbonyltriazolinones, triazolopyrimidines or pyrimidyl(oxy/thio)benzoates, such as oilseed rape imidazolinone-tolerant mutants PM1 and PM2, currently marketed as Clearfield® canola. Further, the plants according to the invention may additionally contain an endogenous or a transgene which confers increased oil content or improved oil composition, such as a 12:0 ACP thioesteraseincrease to obtain high laureate, which confers pollination control, such as such as barnase under control of an anther-specific promoter to obtain male sterility, or barstar under control of an anther-specific promoter to confer restoration of male sterility, or such as the Ogura cytoplasmic male sterility and nuclear restorer of fertility.

The plants or seeds of the plants according to the invention may be further treated with a chemical compound, such as a chemical compound selected from the following lists: Herbicides: Clethodim, Clopyralid, Diclofop, Ethametsulfuron, Fluazifop, Glufosinate, Glyphosate, Metazachlor, Quinmerac, Quizalofop, Tepraloxydim, Trifluralin. Fungicides/PGRs: Azoxystrobin, N-[9-(dichloromethylene)-1,2,3,4-tetrahydro-1,4-methanonaphthalen-5-yl]-3-(difluoromethyl)-1-methyl-1H-pyrazole-4-carboxamide (Benzovindiflupyr, Benzodiflupyr), Bixafen, Boscalid, Carbendazim, Carboxin, Chlormequat-chloride, Coniothryrium minitans, Cyproconazole, Cyprodinil, Difenoconazole, Dimethomorph, Dimoxystrobin, Epoxiconazole, Famoxadone, Fluazinam, Fludioxonil, Fluopicolide, Fluopyram, Fluoxastrobin, Fluquinconazole, Flusilazole, Fluthianil, Flutriafol, Fluxapyroxad, Iprodione, Isopyrazam, Mefenoxam, Mepiquat-chloride, Metalaxyl, Metconazole, Metominostrobin, Paclobutrazole, Penflufen, Penthiopyrad, Picoxystrobin, Prochloraz, Prothioconazole, Pyraclostrobin, Sedaxane, Tebuconazole, Tetraconazole, Thiophanate-methyl, Thiram, Triadimenol, Trifloxystrobin, *Bacillus firmus, Bacillus firmus* strain I-1582, *Bacillus subtilis, Bacillus subtilis* strain GB03, *Bacillus subtilis* strain QST 713, *Bacillus pumulis, Bacillus. pumulis* strain GB34. Insecticides: Acetamiprid, Aldicarb, Azadirachtin, Carbofuran, Chlorantraniliprole (Rynaxypyr), Clothianidin, Cyantraniliprole (Cyazypyr), (beta-)Cyfluthrin, gamma-Cyhalothrin, lambda-Cyhalothrin, Cypermethrin, Deltamethrin, Dimethoate, Dinetofuran, Ethiprole, Flonicamid, Flubendiamide, Fluensulfone, Fluopyram,Flupyradifurone, tau-Fluvalinate, Imicyafos, Imidacloprid, Metaflumizone, Methiocarb, Pymetrozine, Pyrifluquinazon, Spinetoram, Spinosad, Spirotetramate, Sulfoxaflor, Thiacloprid, Thiamethoxam, 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide, 1-(3-chloropyridin-2-yl)-N-[4-cyano-2-methyl-6-(methylcarbamoyl) phenyl]-3-{[5-(trifluoromethyl)-1H-tetrazol-1-yl]methyl}-1H-pyrazole-5-carboxamide, 1-{2-fluoro-4-methyl-5-[(2,2,2-trifluormethyl)sulfinyl]phenyl}-3-(trifluoromethyl)-1H-1,2,4-triazol-5-amine, (1E)-N-[(6-chloropyridin-3-yl) methyl]-N'-cyano-N-(2,2-difluoroethyl)ethanimidamide, *Bacillus firmus, Bacillus firmus* strain I-1582, *Bacillus subtilis, Bacillus subtilis* strain GB03, *Bacillus subtilis* strain QST 713, Metarhizium anisopliae F52.

Whenever reference to a "plant" or "plants" according to the invention is made, it is understood that also plant parts (cells, tissues or organs, seed pods, seeds, severed parts such as roots, leaves, flowers, pollen, etc.), progeny of the plants which retain the distinguishing characteristics of the parents, such as seed obtained by selfing or crossing, e.g. hybrid seed (obtained by crossing two inbred parental lines), hybrid plants and plant parts derived there from are encompassed herein, unless otherwise indicated.

In some embodiments, the plant cells of the invention as well as plant cells generated according to the methods of the invention, may be non-propagating cells.

The obtained plants according to the invention can be used in a conventional breeding scheme to produce more plants with the same characteristics or to introduce the same characteristic in other varieties of the same or related plant species, or in hybrid plants. The obtained plants can further be used for creating propagating material. Plants according to the invention can further be used to produce gametes, seeds (including crushed seeds and seed cakes), seed oil, embryos, either zygotic or somatic, progeny or hybrids of plants obtained by methods of the invention. Seeds obtained from the plants according to the invention are also encompassed by the invention.

"Creating propagating material", as used herein, relates to any means know in the art to produce further plants, plant parts or seeds and includes inter alia vegetative reproduction methods (e.g. air or ground layering, division, (bud) grafting, micropropagation, stolons or runners, storage organs such as bulbs, corms, tubers and rhizomes, striking or cutting, twin-scaling), sexual reproduction (crossing with another plant) and asexual reproduction (e.g. apomixis, somatic hybridization).

As used herein "comprising" is to be interpreted as specifying the presence of the stated features, integers, steps or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a nucleic acid which is functionally or structurally defined, may comprise additional DNA regions etc.

Furthermore, the disclosed invention is expected to yield similar results in other seed crop plant species. Particularly, it is expected to drive early stage seed-specific and endosperm preferential expression in soybean. It is also expected to drive early stage seed-specific and endosperm preferential expression in wheat. The disclosed promoter may lead to a early stage seed-specific and endosperm preferential expression in cotton.

The sequence listing contained in the file named "BCS16-2001_ST25.txt", which is 60 kilobytes (size as measured in Microsoft Windows®), contains 47 sequences SEQ ID NO: 1 through SEQ ID NO: 47 is filed herewith by electronic submission and is incorporated by reference herein.

In the description and examples, reference is made to the following sequences:
SEQUENCES SEQ ID NO: 1: nucleotide sequence of the T-DNA Penodl3-4 BnC2::GUS.
SEQ ID NO: 2: nucleotide sequence of the promoter Penodl3-4 BnC2.
SEQ ID NO: 3: nucleotide sequence of the promoter Penodl3-4 BnC1.
SEQ ID NO: 4: nucleotide sequence of the promoter Penodl3-4 BnA2.
SEQ ID NO: 5: nucleotide sequence of the promoter Penodl3-4 BnA1.
SEQ ID NO: 6: nucleotide sequence of the promoter Penodl3-4 BoC2.
SEQ ID NO: 7: nucleotide sequence of the promoter Penodl3-4 BoC1.
SEQ ID NO: 8: nucleotide sequence of the promoter Penodl3-4 BrA2.
SEQ ID NO: 9: nucleotide sequence of the promoter Penodl3-4 BrA1.
SEQ ID NO: 10: nucleotide sequence of the promoter Penodl3-4 BjB2.
SEQ ID NO: 11: nucleotide sequence of the promoter Penodl3-4 BjB1.
SEQ ID NO: 12: nucleotide sequence of the promoter Penodl3-4 BjA2.
SEQ ID NO: 13: nucleotide sequence of the promoter Penodl3-4 BjA1.
SEQ ID NO: 14: amino acid sequence of ENODL3-4 BnC2.
SEQ ID NO: 15: amino acid sequence of ENODL3-4 BnC1.
SEQ ID NO: 16: amino acid sequence of ENODL3-4 BnA2.
SEQ ID NO: 17: amino acid sequence of ENODL3-4 BnA1.
SEQ ID NO: 18: amino acid sequence of ENODL3-4 BoC2.
SEQ ID NO: 19: amino acid sequence of ENODL3-4 BoC1.
SEQ ID NO: 20: amino acid sequence of ENODL3-4 BrA2.
SEQ ID NO: 21: amino acid sequence of ENODL3-4 BrA1.
SEQ ID NO: 22: amino acid sequence of ENODL3-4 BjB2.
SEQ ID NO: 23: amino acid sequence of ENODL3-4 BjB1.
SEQ ID NO: 24: amino acid sequence of ENODL3-4 BjA2.
SEQ ID NO: 25: amino acid sequence of ENODL3-4 BjA1.
SEQ ID NO: 26: nucleotide sequence of the coding sequence of ENODL3-4 BnC2.
SEQ ID NO: 27: nucleotide sequence of the coding sequence of ENODL3-4 BnC1.
SEQ ID NO: 28: nucleotide sequence of the coding sequence of ENODL3-4 BnA2.
SEQ ID NO: 29: nucleotide sequence of the coding sequence of ENODL3-4 BnA1.
SEQ ID NO: 30: nucleotide sequence of the coding sequence of ENODL3-4 BoC2.
SEQ ID NO: 31: nucleotide sequence of the coding sequence of ENODL3-4 BoC1.
SEQ ID NO: 32: nucleotide sequence of the coding sequence of ENODL3-4 BrA2.
SEQ ID NO: 33: nucleotide sequence of the coding sequence of ENODL3-4 BrA1.
SEQ ID NO: 34: nucleotide sequence of the coding sequence of ENODL3-4 BjB2.
SEQ ID NO: 35: nucleotide sequence of the coding sequence of ENODL3-4 BjB1.
SEQ ID NO: 36: nucleotide sequence of the coding sequence of ENODL3-4 BjA2.
SEQ ID NO: 37: nucleotide sequence of the coding sequence of ENODL3-4 BjA1.
SEQ ID NO: 38: consensus motif 1.
SEQ ID NO: 39: consensus motif 3.
SEQ ID NO: 40: consensus motif 4.
SEQ ID NO: 41: consensus motif 5.
SEQ ID NO: 42: consensus motif 7.
SEQ ID NO: 43: consensus motif 8.
SEQ ID NO: 44: consensus motif 9.
SEQ ID NO: 45: consensus motif 10.
SEQ ID NO: 46: consensus motif 11.
SEQ ID NO: 47: consensus motif 12.
SEQ ID NO: 48: 3 prime end nucleotide sequence of the promoter Penodl3-4 BnC2.
SEQ ID NO: 49: 3 prime end nucleotide sequence of the promoter Penodl3-4 BnC1.
SEQ ID NO: 50: 3 prime end nucleotide sequence of the promoter Penodl3-4 BnA2.
SEQ ID NO: 51: 3 prime end nucleotide sequence of the promoter Penodl3-4 BnA1.
SEQ ID NO: 52: 3 prime end nucleotide sequence of the promoter Penodl3-4 BoC2.
SEQ ID NO: 53: 3 prime end nucleotide sequence of the promoter Penodl3-4 BoC1.
SEQ ID NO: 54: 3 prime end nucleotide sequence of the promoter Penodl3-4 BrA2.
SEQ ID NO: 55: 3 prime end nucleotide sequence of the promoter Penodl3-4 BrA1.
SEQ ID NO: 56: 3 prime end nucleotide sequence of the promoter Penodl3-4 BjB2.
SEQ ID NO: 57: 3 prime end nucleotide sequence of the promoter Penodl3-4 BjB1.
SEQ ID NO: 58: 3 prime end nucleotide sequence of the promoter Penodl3-4 BjA2.
SEQ ID NO: 59: 3 prime end nucleotide sequence of the promoter Penodl3-4 BjA1.

EXAMPLES

Unless stated otherwise in the Examples, all recombinant DNA techniques are carried out according to standard protocols as described in Sambrook and Russell (2001) Molecular Cloning: A Laboratory Manual, Third Edition, Cold Spring Harbor Laboratory Press, NY, in Volumes 1 and 2 of Ausubel et al. (1994) Current Protocols in Molecular Biology, Current Protocols, USA and in Volumes I and II of Brown (1998) Molecular Biology LabFax, Second Edition, Academic Press (UK). Standard materials and methods for plant molecular work are described in Plant Molecular Biology Labfax (1993) by R.D.D. Croy, jointly published by BIOS Scientific Publications Ltd (UK) and Blackwell Scientific Publications, UK. Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

Example 1—Generation of Expression Constructs with the Penodl3-4 BnC2 Promoter of *Brassica napus* Operably Linked to the GUS Reporter Gene (Penodl3-4BnC2::GUS)

The promoter sequence of the *Brassica napus* enodl3-4 C2 promoter (SEQ ID NO: 2 or 5' to 3' position 139 to 1113 of SEQ ID NO:1) isolated from an in house developed *Brassica napus* line, the GUS gene (β-glucuronidase) with intron (5' to 3' position 1116 to 3116 of SEQ ID NO: 1) and a fragment of the 3' untranslated region (UTR) of the gene 7 of *Agrobacterium tumefaciens* octopine (5' to 3' position 3172 to 3376 of SEQ ID NO: 1) were assembled in a vector which contains the bar selectable marker cassette (position 3457 to 5967 of SEQ ID NO: 1) to result in the T-DNA Penodl3-4BnC2::GUS (SEQ ID NO: 1).

Example 2—Generation of Transgenic Plants Comprising the Penodl3-4BnC2::GUS

In a next step the recombinant vectors comprising the expression cassette of example 1, i. e. Penodl3-4BnC2, were used to stably transform *Brassica napus*.

Example 3—in Planta Expression Pattern of Penodl3-4BnC2::GUS in *Brassica napus*

The in planta expression pattern of Penodl3-4BnC2::GUS in the different seed tissues and non-seed tissues of *Brassica napus* seeds was monitored according to the method of Jasik et al. 2011.

No GUS activity was detected in the assessed non-seed tissues, namely young leaves, young stems, flower buds, flowers and pods, thereby confirming the seed-specificity of the selected promoters.

FIG. 1 shows the GUS labelling of the reporter gene in the embryo, endosperm and seed coat at early and late seed developmental stages. The strong staining of the endosperm, at least twice stronger than in the other seed tissues, clearly confirms the endosperm-preferential expression driven by the promoter Penodl3-4BnC2 (panel A). Close up views on the seed coat at early stage demonstrate that though less pronounced, the transgene expression is also detected in the seed coat, with the outer integument being more labelled as compared to the inner integument (panel B). Close up views on the seed coat at late stage show that the GUS labelling occurs in the outer integument but not in the inner integument (panel C).

Figure 2:
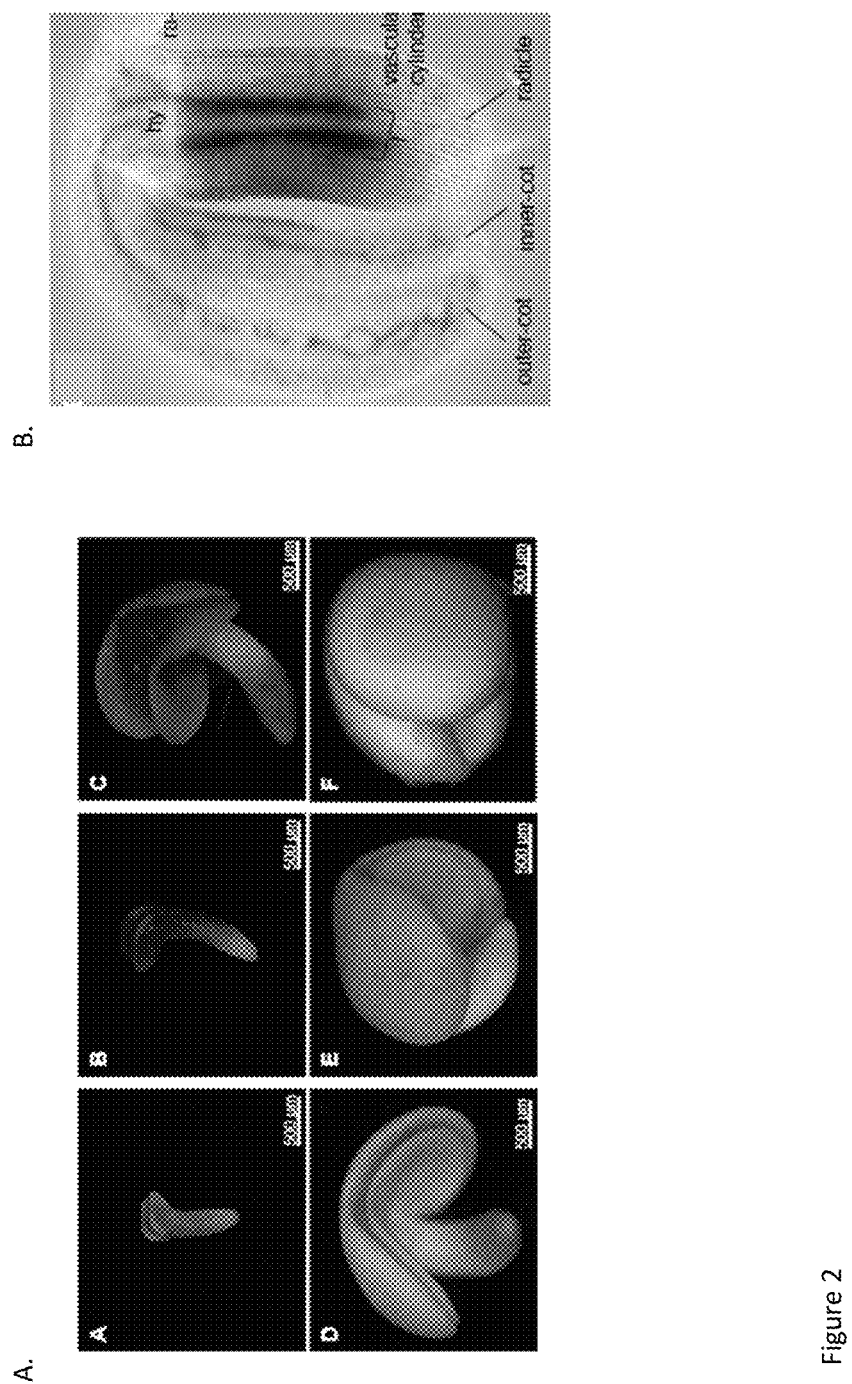
FIG. 2: GUS staining in the embryos carrying Penodl3-4BnC2::GUS. A: GUS labelling in whole embryos at different developmental stages: sub-panel A: 10 to 12 DAF, sub-panel B: 15 to 18 DAF, sub-panel C: 20 to 23 DAF; sub-panel D: 23 to 27 DAF; sub-panel E: 27 to 32 DAF; sub-panel F: 35 to 40 DAF. B: GUS labelling in sectioned embryos at late stage.

FIG. 2 shows pictures of the stained embryos at different developmental stages. The construct tested lead to moderate GUS activity detected in the embryo at early stages of embryo development (panel A, sub-panels A to C). Staining intensity then decreases within regions of the embryo which are involved in intense cell expansion. Although no tissue specificity is visible at the earliest stage, expression becomes progressively restricted to the vasculature in mature embryos (panel B).

Figure 3:
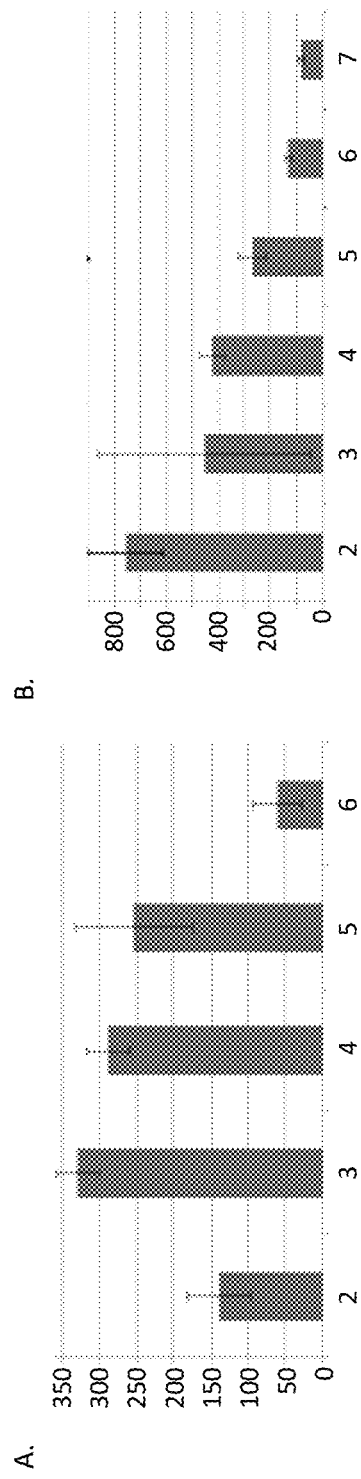
FIG. 3: Semi quantitative assessment of GUS labelling ($\mu$U*mg$^{-1}$ fresh weight*h) in transgenic lines carrying a Penodl3-4BnC2::GUS T-DNA. Seed coats (A) and embryos (B) stained at the following stages: 2: 13 to 15 DAF, 3: 16 to 18 DAF, 3: 19 to 23 DAF, 4: 25 to 29 DAF, 6: 31 to 35 DAF, 7: 37 to 40 DAF.

FIG. 3 provides the semi quantitative assessment of the GUS labelling in the seed coat and the embryo of transgenic lines carrying the Penodl3-4BnC2::GUS T-DNA. The GUS staining in the seed coat is the strongest during early- and mid-developmental stages (panel A) while in the embryo the labelling is the strongest at early stages and then decreases as the embryo progresses towards maturation (panel B).

Example 4—Identification of the Different *Brassica napus* Copies of ENODL3-4 and of the Orthologues of ENODL3-4 in *Brassica rapa*, *Brassica oleracea* and *Brassica juncea*

The sequences of the different *Brassica napus* copies of ENODL3-4 as well as their orthologues in *Brassica rapa*, *Brassica oleracea* and *Brassica juncea* were obtained by blasting the coding sequence of the ENODL3-4 BnC2 against an in-house database of *Brassica napus*, *Brassica rapa*, *Brassica oleracea* and *Brassica juncea* sequences.

The nucleotide sequences obtained in this way are given in SEQ ID NO: 26 to SEQ ID NO: 37. These nucleotide sequences were translated into amino acid sequences, given in SEQ ID NO: 14 to SEQ ID NO: 25.

FIG. 4 shows the alignment of the retrieved amino acid sequences. Any two of these sequences share at least 80% identity.

Example 5—RNA Isolation from Different Tissues of *Brassica napus* and *Brassica juncea*

The following tissues were isolated from *Brassica napus*:
a. Apical meristem 33 days after sowing (DAS) (including smallest leaves) (AM33)
b. Big flower buds (>5 mm) 42 DAS (BFB42)
c. Cotyledons (with hypocotyl) 10 DAS (CTYL10)
d. Open flowers 52 DAS (OF52)
e. Pods 14-20 DAS (Pod2)
f. Pods 21-25 DAS (Pod3)
g. Roots 14 DAS (Ro2w)
h. Small flower buds 5 mm 42 DAS (SFB42)
i. Seeds 14-20 days after flowering (DAF) (Seed2)
j. Seeds 21-25 DAF (Seed3)
k. Seeds 26-30 DAF (Seed4)
l. Seeds 31-35 DAF (Seed5)
m. Seeds 42 DAF (Seed6)
n. Seeds 49 DAF (Seed7)
o. Stem 14 DAS (St2w)
p. Stem 33 DAS (St5w)
q. Young leaf 33 DAS 3 cm leaf next to apical meristem) (YL33)

The following tissues were isolated from *Brassica juncea*:
a. Apical meristem 22 days after sowing (DAS) (including smallest leaves) (AM22)
b. Big flower buds (>5 mm) 35 DAS (BFB35)
c. Cotyledons (with hypocotyl) 8 DAS (CTYL8)
d. Open flowers 35 DAS (OF35)
e. Pods 14-20 DAS (Pod2)
f. Pods 21-25 DAS (Pod3)
g. Pods 26-30 DAS (Pod4)
h. Pods 31-35 DAS (Pod5)
i. Roots 14 DAS (Ro2w)
j. Small flower buds 5 mm 35 DAS (SFB35)
k. Seeds 14-20 days after flowering (DAF) (Seed2)
l. Seeds 21-25 DAF (Seed3)
m. Seeds 26-30 DAF (Seed4)
n. Seeds 31-35 DAF (Seed5)
o. Seeds 42 DAF (Seed6)
p. Seeds 49 DAF (Seed7)
q. Stem 14 DAS (St2w)
r. Stem 22 DAS (St3w)

s. Young leaf 22 DAS 3 cm leaf next to apical meristem) (YL22)

t. Old leaf 22 DAS (OL22)

The following seed sub-tissues were isolated from *Brassica napus*:

a. Endosperm, 18 days after flowering (DAF)
b. Endosperm, 24 DAF
c. Embryonic hypocotyl, 18 DAF
d. Embryonic hypocotyl, 24 DAF
e. Embryonic hypocotyl, 28 DAF
f. Embryonic hypocotyl, 32 DAF
g. Embryonic hypocotyl, 46 DAF
h. Embryonic inner cotyledon, 18 DAF
i. Embryonic inner cotyledon, 24 DAF
j. Embryonic inner cotyledon, 28 DAF
k. Embryonic inner cotyledon, 32 DAF
l. Embryonic inner cotyledon, 46 DAF
m. Embryonic outer cotyledon, 18 DAF
n. Embryonic outer cotyledon (inner part), 24 DAF
o. Embryonic outer cotyledon (inner part), 28 DAF
p. Embryonic outer cotyledon (inner part), 32 DAF
q. Embryonic outer cotyledon (inner part), 46 DAF
r. Embryonic outer cotyledon (outer part), 24 DAF
s. Embryonic outer cotyledon (outer part), 28 DAF
t. Embryonic outer cotyledon (outer part), 32 DAF
u. Embryonic outer cotyledon (outer part), 46 DAF For the isolation of the seed sub-tissues, freshly harvested seeds were frozen at −80° C. and cut into 20 μm sections. Sections were placed on PET-membranes, lyophilized at −20° C., and then used for laser-assisted microdissection (PALM Laser-Microbeam instrument; Bernried/Germany) (for details see Schiebold et al., 2011, Plant Methods 7:19). Up to 5 distinct embryonic tissues plus endosperm were targeted. Tissue dissection was applied to seeds at 18, 24, 28, 32 and 46 DAF, covering the developmental period from onset of storage activity until late maturation. RNA was extracted (purification of total RNA by RNeasy Micro kit; Qiagen) and amplified (C&E version ExpressArt mRNA amplification Nano kit; Amp-tec) as detailed in Schiebold et al. 2011 (supra).

Total RNA from the non-seed sub-tissues was isolated according to standard methods.

Figure 5:
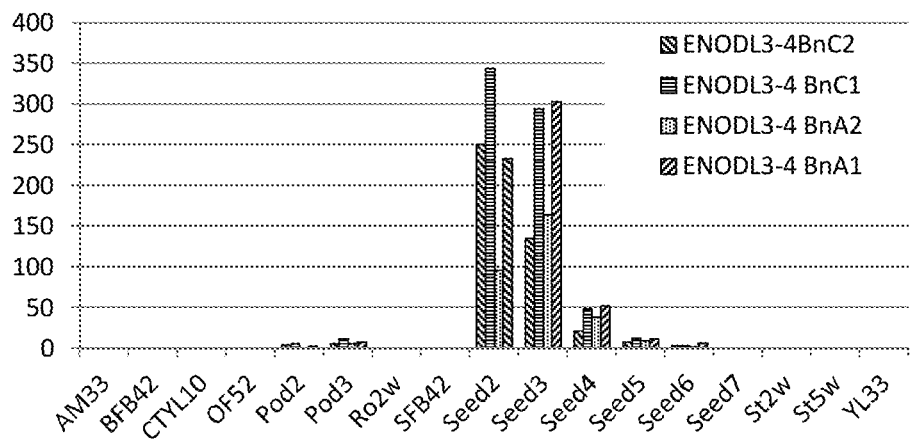
FIG. 5: Relative expression levels of different ENODL3-4 transcripts in different plant tissues. A: ENODL3-4 BnC2, ENODL3-4 BnC1, ENODL3-4 BnA2 and ENODL3-4 BnA1; B: ENODL3-4 BoC1, ENODL3-4 BoC2, ENODL3-4 BrA1 and ENODL3-4 BrA2; C: ENODL3-4BjB2, ENODL3-4 BjA1, ENODL3-4 BjB1 and ENODL3-4 BjA2. Different tissues for A and B: AM33: Apical meristem 33 days after sowing (DAS); BFB42: Big flower buds 42 DAS; CTYL10: Cotyledons 10 DAS; OF52: Open flowers 52 DAS; Pod2: Pods 14-20 DAS; Pod3: Pods 21-25 DAS; Ro2w: Roots 14 DAS; SFB42: Small flower buds 42 DAS; Seed2: Seeds 14-20 days after flowering (DAF); Seed3: Seeds 21-25 DAF; Seed4: Seeds 26-30 DAF; Seed5: Seeds 31-35 DAF; Seed6: Seeds 42 DAF; Seed7: Seeds 49 DAF; St2w: Stem 14 DAS; St5w: Stem 33 DAS; YL33: Young leaf 33 DAS. Different tissues for C: AM22: Apical meristem 22 days after sowing (DAS); BFB35: Big flower buds 35 DAS; CTYL8: Cotyledons 8 DAS; OF35: Open flowers 35 DAS; Pod2: Pods 14-20 DAS; Pod3: Pods 21-25 DAS; Pod4: Pods 26-30 DAS; Pod5: Pods 31-35 DAS; Ro2w: Roots 14 DAS; SFB35: Small flower buds 35 DAS; Seed2: Seeds 14-20 days after flowering (DAF); Seed3: Seeds 21-25 DAF; Seed4: Seeds 26-30 DAF; Seed5: Seeds 31-35 DAF; Seed6: Seeds 42 DAF; Seed7: Seeds 49 DAF; St2w: Stem 14 DAS; St3w: Stem 22 DAS; YL22: Young leaf 22 DAS; OL22: Old leaf 22 DAS.
Figure 5:
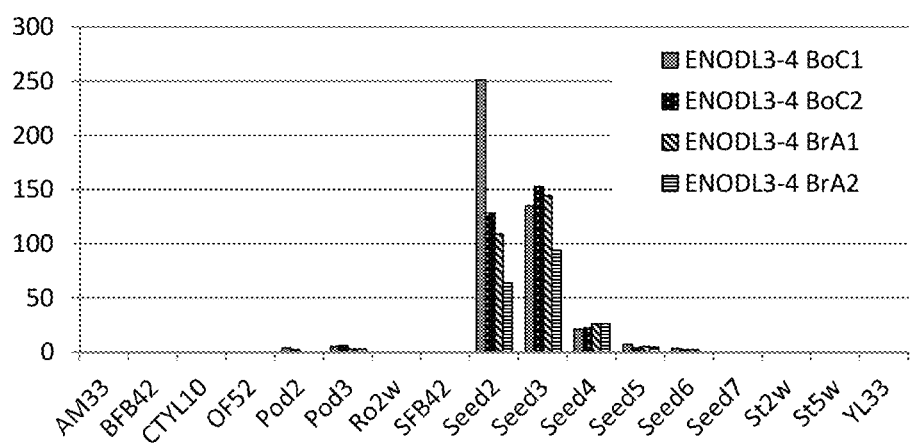
Figure 5:
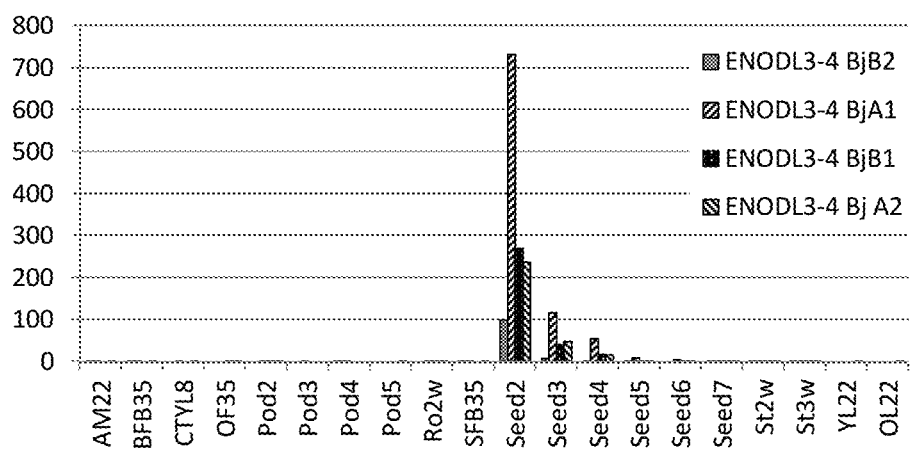

In our growth conditions, the correspondence between embryo developmental stages and the selected time points is as follows:

a. Between 10 and 13 DAF: torpedo stage
b. Seed2 or between 14 and 20 DAF: "walking stick" cotyledon stage
c. Seed3 or between 21 and 25 DAF: curled cotyledon stage
d. Seed4 and Seed5 or between 26 and 35 DAF: green cotyledon stage
e. Seed6 and Seed7 or after 36 DAF: mature embryo Example 6—in Silico Expression Analyses of the Different Copies of ENODL3-4 of *Brassica napus* and their Orthologues FIG. 5 shows the relative expression levels of the endogenous transcripts of the different *Brassica napus* (A), *Brassica rapa* and *Brassica oleracea* (B) and *Brassica juncea* (C) copies of ENODL3-4 in different tissues, as isolated in Example 5.

The ENODL3-4 BnC2 transcript is abundantly detected in the Seed2 and Seed3 tissues, and only barely detectable in the Seed4, Seed5, Seed6, Pod2 and Pod3 tissues. This result confirms, as determined in planta, that Penodl3-4 BnC2 has early stage seed-specific promoter activity.

The ENODL3-4 BnC1 transcript is abundantly detected in the Seed2 and Seed3 tissues, mildly detected in the Seed4 tissues and only barely detectable in the Seed5, Seed6, Pod2 and Pod3 tissues. This result indicates that Penodl3-4 BnC1 has early stage seed-specific promoter activity.

The ENODL3-4 BnA2 transcript is abundantly detected in the Seed2 and Seed3 tissues, mildly detected in the Seed4 tissues and only barely detectable in the Seed5 and Pod3 tissues. This result indicates that Penodl3-4 BnA2 has early stage seed-specific promoter activity.

The ENODL3-4 BnA1 transcript is abundantly detected in the Seed2 and Seed3 tissues, mildly detected in the Seed4 tissues and only barely detectable in the Seed5, Seed6, Pod2 and Pod3 tissues. This result indicates that Penodl3-4 BnA1 has early stage seed-specific promoter activity.

The ENODL3-4 BoC1 transcript is abundantly detected in the Seed2 and Seed3 tissues, and only barely detectable in the Seed4, Seed5, Seed6, Pod2 and Pod3 tissues. This result indicates that Penodl3-4 BoC1 has early stage seed-specific promoter activity.

The ENODL3-4 BoC2 transcript is abundantly detected in the Seed2 and Seed3 tissues, and only barely detectable in the Seed4, Seed5, Pod2 and Pod3 tissues. This result indicates that Penodl3-4 BoC2 has early stage seed-specific promoter activity.

The ENODL3-4 BrA1 transcript is abundantly detected in the Seed2 and Seed3 tissues, and only barely detectable in the Seed4, Seed5, Seed6 and Pod3 tissues. This result indicates that Penodl3-4 BrA1 has early stage seed-specific promoter activity.

The ENODL3-4 BrA2 transcript is abundantly detected in the Seed2 and Seed3 tissues, and only barely detectable in the Seed4, Seed5, Pod3 tissues. This result indicates that Penodl3-4 BrA2 has early stage seed-specific promoter activity.

The ENODL3-4 BjB1 transcript is abundantly detected in the Seed2 tissues, mildly detected in the Seed3 tissues and only barely detectable in the Seed4 tissues. This result indicates that Penodl3-4 BjB1 has early stage seed-specific promoter activity.

The ENODL3-4 BjB2 transcript is abundantly detected in the Seed2 tissues, and only barely detectable in the Seed3 tissues. This result indicates that Penodl3-4 BjB2 has early stage seed-specific promoter activity.

The ENODL3-4 BjA1 transcript is abundantly detected in the Seed2 and Seed3 tissues, mildly detected in the Seed4 tissues and only barely detectable in the Seed5 and Seed6 tissues. This result indicates that Penodl3-4 BjA1 has early stage seed-specific promoter activity.

The ENODL3-4 BjA2 transcript is abundantly detected in the Seed2 tissues, mildly detected in the Seed3 tissues and only barely detectable in the Seed4 tissues. This result indicates that Penodl3-4 BjA2 has early stage seed-specific promoter activity.

Figure 6:
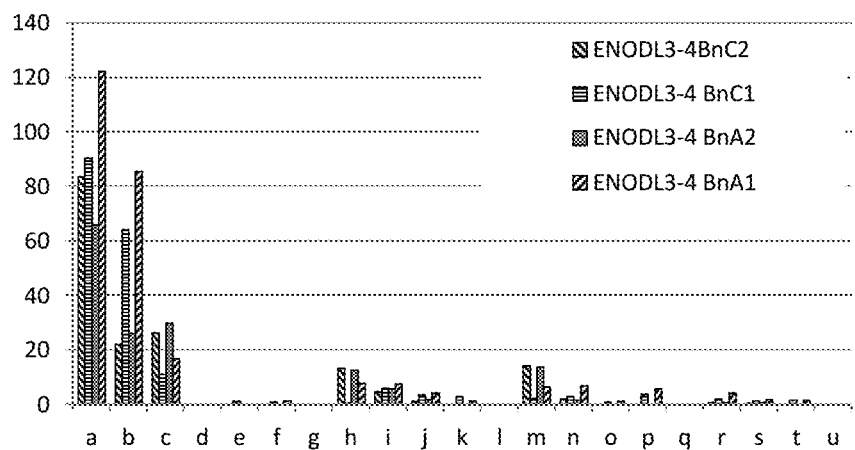
FIG. 6: Relative expression levels of different ENODL3-4 transcripts in different seed sub-tissues. A: ENODL3-4 BnC2, ENODL3-4 BnC1, ENODL3-4 BnA2 and ENODL3-4 BnA1; B: ENODL3-4 BoC1, ENODL3-4 BoC2, ENODL3-4 BrA1 and ENODL3-4 BrA2. Different seed sub-tissues: a: Endosperm, 18 days after flowering (DAF); b: Endosperm, 24 DAF; c: embryonic hypocotyl, 18 DAF; d: embryonic hypocotyl, 24 DAF; e: embryonic hypocotyl, 28 DAF; f: embryonic hypocotyl, 32 DAF; g: embryonic hypocotyl, 46 DAF; h: embryonic inner cotyledon, 18 DAF; i: embryonic inner cotyledon, 24 DAF; j: embryonic inner cotyledon, 28 DAF; k: embryonic inner cotyledon, 32 DAF; l: embryonic inner cotyledon, 46 DAF; m: embryonic outer cotyledon, 18 DAF; n: embryonic outer cotyledon (inner part), 24 DAF; o: embryonic outer cotyledon (inner part), 28 DAF; p: embryonic outer cotyledon (inner part), 32 DAF; q: embryonic outer cotyledon (inner part), 46 DAF; r: embryonic outer cotyledon (outer part), 24 DAF; s: embryonic outer cotyledon (outer part), 28 DAF; t: embryonic outer cotyledon (outer part), 32 DAF; u: embryonic outer cotyledon (outer part), 46 DAF.
Figure 6:
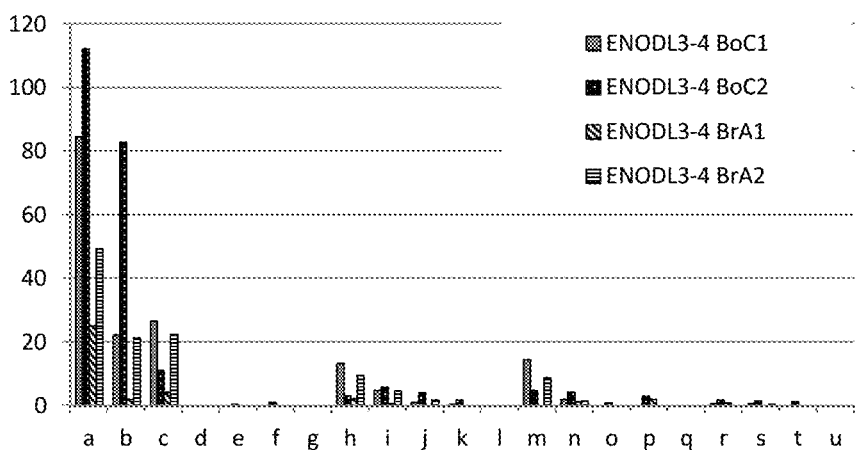

FIG. 6 shows the relative expression levels of the endogenous transcripts of the different *Brassica napus* (A), *Brassica rapa* and *Brassica oleracea* (B) copies of ENODL3-4 in different seed sub-tissues, as isolated in Example 5.

The ENODL3-4 BnC2 transcript is abundantly detected in the endosperm tissues at 18 DAF, and mildly detected in the endosperm tissues at 24 DAF. In the embryo, the ENODL3-4 BnC2 transcript is mildly detected in the hypocotyl, the inner cotyledon and the outer cotyledon at 18 DAF, while barely detectable in older tissues. This result confirms, as determined in planta, that Penodl3-4 BnC2 has endosperm-preferential promoter activity.

The ENODL3-4 BnC1 transcript is abundantly detected in the endosperm tissues at 18 and 24 DAF. In the embryo, the ENODL3-4 BnC1 transcript is barely detected in the hypocotyl, the inner cotyledon and the outer cotyledon at early stages. This result indicates that Penodl3-4 BnC1 has endosperm-preferential promoter activity.

The ENODL3-4 BnA2 transcript is abundantly detected in the endosperm tissues at 18 DAF, and mildly detected in the endosperm tissues at 24 DAF. In the embryo, the ENODL3-4 BnA2 transcript is mildly detected in the hypocotyl, the inner cotyledon and the outer cotyledon at 18 DAF, while barely detectable in older tissues. This result indicates that Penodl3-4 BnA2 has endosperm-preferential promoter activity.

The ENODL3-4 BnA1 transcript is abundantly detected in the endosperm tissues at 18 and 24 DAF. In the embryo, the ENODL3-4 BnA1 transcript is mildly detected in the hypocotyl at 18 DAF and barely detected in the inner cotyledon and the outer cotyledon at early stages. This result indicates that Penodl3-4 BnA1 has endosperm-preferential promoter activity.

The ENODL3-4 BoC1 transcript is abundantly detected in the endosperm tissues at 18 DAF and mildly detected in the endosperm tissues at 24 DAF. In the embryo, the ENODL3-4 BoC1 transcript is mildly detected in the hypocotyl, the inner cotyledon and the outer cotyledon at 18 DAF, while barely detectable in older tissues. This result indicates that Penodl3-4 BoC1 has endosperm-preferential promoter activity.

The ENODL3-4 BoC2 transcript is abundantly detected in the endosperm tissues at 18 and 24 DAF. In the embryo, the ENODL3-4 BoC2 transcript is barely detected in the hypocotyl, the inner cotyledon and the outer cotyledon at early stages. This result indicates that Penodl3-4 BoC2 has endosperm-preferential promoter activity.

The ENODL3-4 BrA1 transcript is mildly detected in the endosperm tissues at 18 DAF, while barely detectable in the endosperm tissues at 24 DAF. In the embryo, the ENODL3-4 BrA1 transcript is barely detected in the hypocotyl tissues at 18 DAF. This result indicates that Penodl3-4 BrA1 has endosperm-preferential promoter activity.

The ENODL3-4 BrA2 transcript is abundantly detected in the endosperm tissues at 18 DAF and mildly detected in the endosperm tissues at 24 DAF. In the embryo, the ENODL3-4 BrA2 transcript is mildly detected in the hypocotyl tissues at 18 DAF, while barely detectable in the inner cotyledon and the outer cotyledon at early stages. This result indicates that Penodl3-4 BrA2 has endosperm-preferential promoter activity.

Example 7—Sequence Analysis of the Promoters of the ENODL3-4 Genes from Brassica rapa, Brassica juncea, Brassica oleracea and Brassica napus For each ENODL3-4 gene identified the 975 bp of genomic DNA sequence upstream of the translation start was retrieved from an in-house database of Brassica napus, Brassica rapa, Brassica oleracea and Brassica juncea sequences. The nucleotide sequences obtained in this way are given in SEQ ID NO: 3 to SEQ ID NO: 13.

Figure 7:
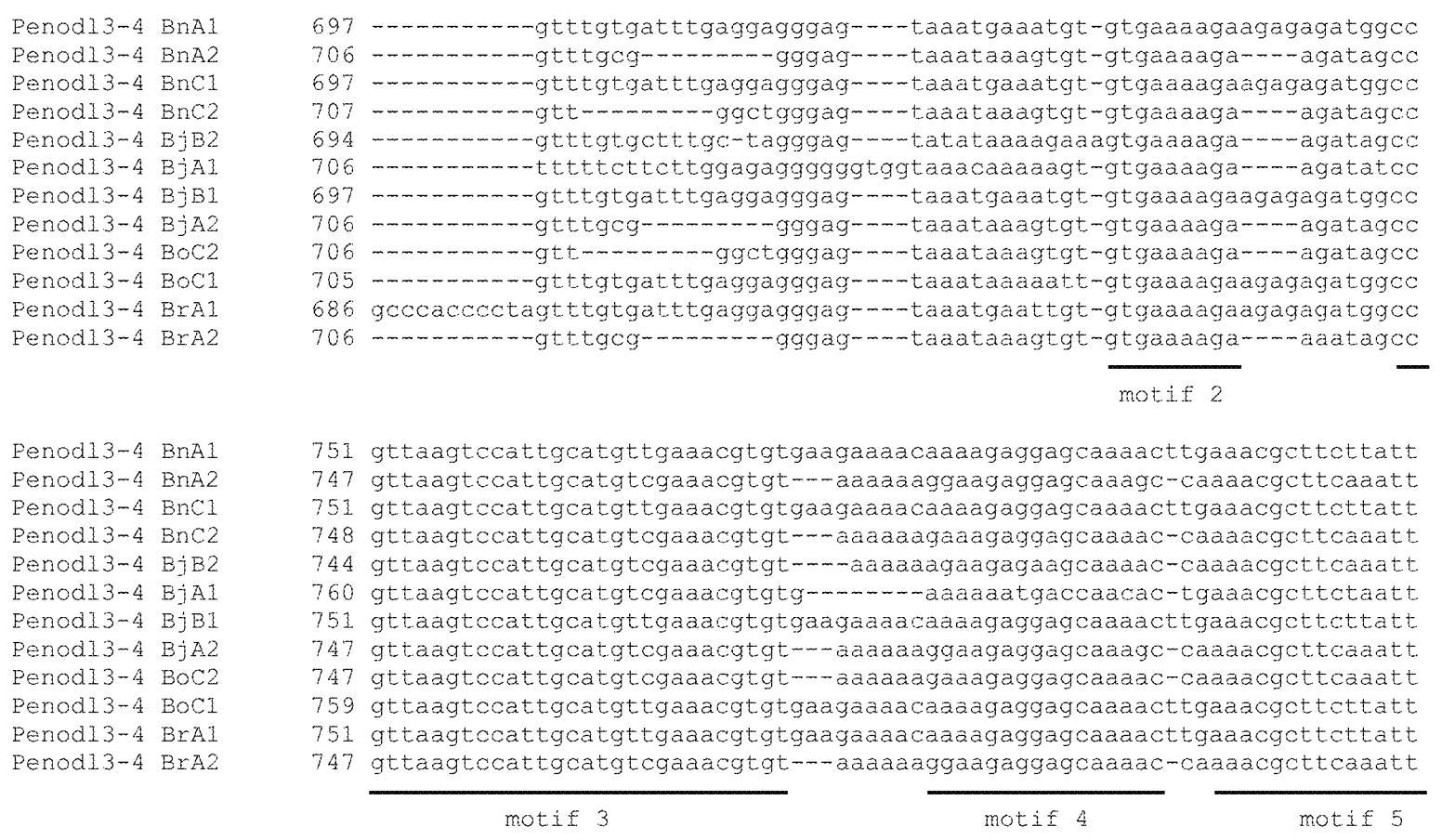

FIG. 7 shows the alignment of the 3' end sequence of the promoter sequences (SEQ ID NO: 2 to SEQ ID NO: 13). These promoters share a surprisingly high level of conservation in this region. Twelve consensus sequences (motifs) were identified. The promoters comprise the following motifs in their 3' 350 bp sequence:
a. motif 1 is given in SEQ ID NO: 38;
b. motif 2 has the sequence gtgaaaaga;
c. motif 3 is given in SEQ ID NO: 39;
d. motif 4 is given in SEQ ID NO: 40;
e. motif 5 is given in SEQ ID NO: 41;
f. motif 6 has the sequence tttgcayrt;
g. motif 7 is given in SEQ ID NO: 42;
h. motif 8 is given in SEQ ID NO: 43;
i. motif 9 is given in SEQ ID NO: 44;
j. motif 10 is given in SEQ ID NO: 45;
k. motif 11 is given in SEQ ID NO: 46;
l. motif 12 is given in SEQ ID NO: 47.

The high degree of conservation of these motifs in all analyzed promoter sequences described herein indicate that these motifs are required for the observed seed-specific and endosperm-preferential expression pattern.

Consequently, as Penodl3-4 BjB1 sequence comprises the motifs 1 to 12, it can be concluded that it has endosperm-preferential promoter activity. As Penodl3-4 BjB2 sequence comprises the motifs 1 to 12, it can be concluded that it has endosperm-preferential promoter activity. As Penodl3-4 BjA2 sequence comprises the motifs 1 to 12, it can be concluded that it has endosperm-preferential promoter activity. As Penodl3-4 BjA1 sequence comprises the motifs 1 to 12, it can be concluded that it has endosperm-preferential promoter activity.

More generally, these results indicate that a Brassica promoter comprising the motifs 1 to 12 would have early stage seed-specific and endosperm-preferential promoter activity.

The invention claimed is:

1. A recombinant gene comprising a nucleic acid having early stage seed-specific and endosperm-preferential promoter activity comprising:
   a. a nucleic acid comprising the nucleotide sequence of any one of SEQ ID NO: 2 to SEQ ID NO: 13;
   b. a nucleic acid comprising a nucleotide sequence having at least 98% sequence identity to any one of SEQ ID NO: 2 to SEQ ID NO: 13; or
   c. a nucleic acid comprising:
      i. the nucleotide sequence of SEQ ID NO: 38;
      ii. the nucleotide sequence gtgaaaaga;
      iii. the nucleotide sequence of SEQ ID NO: 39;
      iv. the nucleotide sequence of SEQ ID NO: 40;
      v. the nucleotide sequence of SEQ ID NO: 41;
      vi. the nucleotide sequence tttgcayrt;
      vii. the nucleotide sequence of SEQ ID NO: 42;
      viii. the nucleotide sequence of SEQ ID NO: 43;
      ix. the nucleotide sequence of SEQ ID NO: 44;
      x. the nucleotide sequence of SEQ ID NO: 45;
      xi. the nucleotide sequence of SEQ ID NO: 46; and
      xii. the nucleotide sequence of SEQ ID NO: 47
operably linked to a heterologous nucleic acid sequence encoding an expression product of interest.

2. The recombinant gene according to claim 1, wherein the expression product of interest is an RNA molecule capable of modulating the expression of a gene or is a protein.

3. A host cell comprising the recombinant gene according to claim 1.

4. The host cell of claim 3, which is an *E. coli* cell, an *Agrobacterium* cell, an algal cell, a yeast cell, or a plant cell.

5. A plant comprising the recombinant gene of claim 1.

6. A plant comprising at least two recombinant genes according to claim 1, wherein said nucleic acid having early stage seed-specific and endosperm-preferential promoter activity.

7. Seeds obtainable from the plant according to claim 5.

8. A method of producing a transgenic plant comprising:
   a. introducing or providing the recombinant gene according to claim 1 to a plant cell to create transgenic cells; and
   b. regenerating transgenic plants from said transgenic cell.

9. A method of effecting early stage seed-specific and endosperm preferential expression of a nucleic acid comprising introducing the recombinant gene according to claim 1 into the genome of a plant.

10. A method for altering seed properties of a plant, comprising introducing the recombinant gene according to claim 1 into the genome of a plant, thereby altering seed properties of the plant compared to the plant without the recombinant gene.

11. The method according to claim 8, wherein said plant is a seed crop plant.

12. A method of producing food, feed, or an industrial product comprising preparing food, feed or industrial product from the plant or part thereof.

13. The method of claim 12, wherein
   a) the food or feed is oil, meal, grain, starch, flour or protein; or
   b) the industrial product is biofuel, fiber, industrial chemicals, a pharmaceutical or a nutraceutical.

14. The recombinant gene according to claim 1, wherein said nucleic acid comprises a. the nucleotide sequence of SEQ ID NO: 38;
b. the nucleotide sequence gtgaaaaga;
c. the nucleotide sequence of SEQ ID NO: 39;
d. the nucleotide sequence of SEQ ID NO: 40;
e. the nucleotide sequence of SEQ ID NO: 41;
f. the nucleotide sequence tttgcayrt;
g. the nucleotide sequence of SEQ ID NO: 42;
h. the nucleotide sequence of SEQ ID NO: 43;
i. the nucleotide sequence of SEQ ID NO: 44;
j. the nucleotide sequence of SEQ ID NO: 45;
k. the nucleotide sequence of SEQ ID NO: 46; and
l. the nucleotide sequence of SEQ ID NO: 47 between the nucleotide positions corresponding to the nucleotide position 626 and the nucleotide position 975 of SEQ ID NO: 2.

15. The recombinant gene according to claim 1, operably linked to a transcription termination and polyadenylation region functional in plants.

16. A method of effecting early stage seed-specific and endosperm preferential expression of a nucleic acid comprising growing the plant according to claim 5.

17. A method for altering seed properties of a plant, comprising growing the plant according to claim 5, wherein seed properties of the plant are altered compared to growing the plant without the recombinant gene.

18. The recombinant gene according to claim 1, further comprising a transcription termination and polyadenylation sequence.

19. The recombinant gene according to claim 1, wherein the nucleic acid comprises the nucleotide sequence of any one of SEQ ID NO: 2 to SEQ ID NO: 13.

20. The recombinant gene according to claim 1, wherein the nucleic acid comprises the nucleotide sequence having at least 98% sequence identity to any one of SEQ ID NO: 2 to SEQ ID NO: 13.

21. The plant according to claim 6, wherein the heterologous nucleic acid sequence is different in each recombinant gene.

* * * * *

SEQUENCE LISTING

```
<160> NUMBER OF SEQ ID NOS: 59

<210> SEQ ID NO 1
<211> LENGTH: 6174
<212> TYPE: DNA
<213> ORGANISM: Artificial Sequence
<220> FEATURE:
<223> OTHER INFORMATION: nucleotide sequence of the T-DNA Penodl3-4::GUS

<400> SEQUENCE: 1
aattacaacg gtatatatcc tgccagtact ttgtggcgct ctatcatagc tataaaccta      60
ttcagcacaa tatcgattaa gggcccctc gagggcgatc gctacgtacc tgcaggcccg     120
```

```
ggttaattaa gcggccgcca ggtttggatt ggtttgggta ttagaatcca aaaaaacacg      180
aagtatccaa aacacaaaaa aagacttgaa acacaaaaat acccgaaatc caaacaaata      240
cctgaaaata ttcatatact caaaagatcc aaaaatttac ccgtaaacct aatccggaga      300
acccaaaaca cccaaaattt taccaaccca aaatatattt ttctaaaatt gaaattttat      360
ccataacctc aaactataac cgaaaaacct taaccataaa cttaaaaata tttgtaatgc      420
cgaaaacata tatgaaatat ccaaacatac ctaatataca caaatcattc caggtacttg      480
ggtacccaat cgagtctcgg atatgaccta aactggagca aagattcgcg gtccaaaaag      540
atattgaata ggtactttgc ccatgattca gacccgaact gcacctgtat tttcgggttg      600
gtttcggatt tagttttca ggtccgacaa actgtagaat cgtatgaaaa aattagatag       660
aaatatatag ataaaatctg aaataataat gtataacaat ctcaaaaaat taattcatat      720
aaaacttttt tataataaaa aaaccgcgct tttaagagag tcaaaatcta gtaagtttat      780
taaaaatgaa tttcagtttt tagttaaatg actaacaaat tggaacatct ggtgtaaaat      840
ggctgttggc tgggagtaaa taaagtgtgt gaaaagaaga tagccgttaa gtccattgca      900
tgtcgaaacg tgtaaaaaag aaagaggagc aaaaccaaaa cgcttcaaat taatttgcat      960
attctctaga gaatccatgc aggaaaaagt ttcacctaac ggctatgact tctctacttt     1020
caccataaat acacatacaa gcaccgaaga gcaacacaga cttcaagaga tcagtgagta     1080
attactttga ggtttagtta aaacttttgg ggaccatggt ccgtcctgta gaaaccccaa     1140
cccgtgaaat caaaaaactc gacggcctgt gggcattcag tctggatcgc gaaaactgtg     1200
gaattgatca gcgttggtgg gaaagcgcgt tacaagaaag ccgggcaatt gctgtgccag     1260
gcagttttaa cgatcagttc gccgatgcag atattcgtaa ttatgcgggc aacgtctggt     1320
atcagcgcga agtctttata ccgaaaggtt gggcaggcca gcgtatcgtg ctgcgtttcg     1380
atgcggtcac tcattacggc aaagtgtggg tcaataatca ggaagtgatg gagcatcagg     1440
gcggctatac gccatttgaa gccgatgtca cgccgtatgt tattgccggg aaaagtgtac     1500
gtaagtttct gcttctacct ttgatatata tataataatt atcattaatt agtagtaata     1560
taatatttca aatattttt tcaaaataaa agaatgtagt atatagcaat tgcttttctg      1620
tagtttataa gtgtgtatat tttaatttat aacttttcta atatatgacc aaaatttgtt     1680
gatgtgcagg tatcaccgtt tgtgtgaaca acgaactgaa ctggcagact atcccgccgg     1740
gaatggtgat taccgacgaa aacggcaaga aaaagcagtc ttacttccat gatttcttta     1800
actatgccgg aatccatcgc agcgtaatgc tctacaccac gccgaacacc tgggtggacg     1860
atatcaccgt ggtgacgcat gtcgcgcaag actgtaacca cgcgtctgtt gactggcagg     1920
tggtggccaa tggtgatgtc agcgttgaac tgcgtgatgc ggatcaacag gtggttgcaa     1980
ctggacaagg cactagcggg actttgcaag tggtgaatcc gcacctctgg caaccgggtg     2040
aaggttatct ctatgaactg tgcgtcacag ccaaaagcca gacagagtgt gatatctacc     2100
cgcttcgcgt cggcatccgg tcagtggcag tgaagggcga acagttcctg attaaccaca     2160
aaccgttcta ctttactggc tttggtcgtc atgaagatgc ggacttgcgt ggcaaaggat     2220
tcgataacgt gctgatggtg cacgaccacg cattaatgga ctggattggg gccaactcct     2280
accgtacctc gcattaccct tacgctgaag agatgctcga ctgggcagat gaacatggca     2340
tcgtggtgat tgatgaaact gctgctgtcg gctttaacct ctctttaggc attggtttcg     2400
aagcgggcaa caagccgaaa gaactgtaca gcgaagaggc agtcaacggg gaaactcagc     2460
aagcgcactt acaggcgatt aaagagctga tagcgcgtga caaaaaccac ccaagcgtgg     2520
```

```
tgatgtggag tattgccaac gaaccggata cccgtccgca aggtgcacgg gaatatttcg    2580
cgccactggc ggaagcaacg cgtaaactcg acccgacgcg tccgatcacc tgcgtcaatg    2640
taatgttctg cgacgctcac accgatacca tcagcgatct ctttgatgtg ctgtgcctga    2700
accgttatta cggatggtat gtccaaagcg gcgatttgga aacggcagag aaggtactgg    2760
aaaaagaact tctggcctgg caggagaaac tgcatcagcc gattatcatc accgaatacg    2820
gcgtggatac gttagccggg ctgcactcaa tgtacaccga catgtggagt gaagagtatc    2880
agtgtgcatg gctggatatg tatcaccgcg tctttgatcg cgtcagcgcc gtcgtcggtg    2940
aacaggtatg gaatttcgcc gattttgcga cctcgcaagg catattgcgc gttggcggta    3000
acaagaaagg gatcttcact cgcgaccgca aaccgaagtc ggcggctttt ctgctgcaaa    3060
aacgctggac tggcatgaac ttcggtgaaa accgcagca gggaggcaaa caatgaatca    3120
acaactctcc tggcgcacca tcgtcggcta cagcctcggc gcgtggcgcg cctaagctag    3180
ctatatcatc aatttatgta ttacacataa tatcgcactc agtctttcat ctacggcaat    3240
gtaccagctg atataatcag ttattgaaat atttctgaat ttaaacttgc atcaataaat    3300
ttatgttttt gcttggacta taatacctga cttgttattt tcaataaaa tatttaaact    3360 atatttcttt caagatgaat tcgatatcat taccctgtta tccctaaagc ttattaatat    3420
aacttcgtat agcatacatt atacgaagtt atgtttcaaa tttattatgt gtttttttc    3480 cgtggtcgag attgtgtatt attctttagt tattacaaga cttttagcta aaatttgaaa    3540
gaatttactt taagaaaatc ttaacatctg agataatttc agcaatagat tatatttttc    3600
attactctag cagtattttt gcagatcaat cgcaacatat atggttgtta gaaaaaatgc    3660
actatatata tatatattat ttttttcaatt aaaagtgcat gatatataat atatatatat    3720
atatatatat gtgtgtgtgt atatggtcaa agaaattctt atacaaatat acacgaacac    3780
atatatttga caaaatcaaa gtattacact aaacaatgag ttggtgcatg gccaaaacaa    3840
atatgtagat taaaaattcc agcctccaaa aaaaaatcca agtgttgtaa agcattatat    3900
atatatagta gatcccaaat ttttgtacaa ttccacactg atcgaatttt taaagttgaa    3960
tatctgacgt aggattttt taatgtctta cctgaccatt tactaataac attcatacgt    4020
tttcatttga aatatcctct ataattatat tgaatttggc acataataag aaacctaatt    4080 ggtgattat tttactagta aatttctggt gatgggcttt ctactagaaa gctctcggaa    4140
aatcttggac caaatccata ttccatgact tcgattgtta accctattag ttttcacaaa    4200
catactatca atatcattgc aacggaaaag gtacaagtaa acattcaat ccgatagga    4260 agtgatgtag gaggttggga agacaggccc agaaagagat ttatctgact tgttttgtgt    4320
atagttttca atgttcataa aggaagatgg agacttgaga agttttttt ggactttgtt    4380 tagctttgtt gggcgttttt ttttttgat caataacttt gttgggctta tgatttgtaa    4440
tattttcgtg gactctttag tttatttaga cgtgctaact ttgttgggct tatgacttgt    4500
tgtaacatat tgtaacagat gacttgatgt gcgactaatc tttacacatt aaacatagtt    4560 ctgtttttg aaagttctta ttttcatttt tatttgaatg ttatatattt ttctatattt    4620
ataattctag taaaaggcaa attttgcttt taaatgaaaa aatatatat tccacagttt    4680 cacctaatct tatgcattta gcagtacaaa ttcaaaaatt tcccattttt attcatgaat    4740
cataccatta tatattaact aaatccaagg taaaaaaag gtatgaaagc tctatagtaa    4800
gtaaaatata aattccccat aaggaaaggg ccaagtccac caggcaagta aaatgagcaa    4860
```

-continued

| | |
|---|---|
| gcaccactcc accatcacac aatttcactc atagataacg ataagattca tggaattatc | 4920 |
| ttccacgtgg cattattcca gcggttcaag ccgataaggg tctcaacacc tctccttagg | 4980 |
| cctttgtggc cgttaccaag taaaattaac ctcacacata tccacactca aaatccaacg | 5040 |
| gtgtagatcc tagtccactt gaatctcatg tatcctagac cctccgatca ctccaaagct | 5100 |
| tgttctcatt gttgttatca ttatatatag atgaccaaag cactagacca aacctcagtc | 5160 |
| acacaaagag taagaagaa caatggaccc agaacgacgc ccggccgaca tccgccgtgc | 5220 |
| caccgaggcg gacatgccgg cggtctgcac catcgtcaac cactacatcg agacaagcac | 5280 |
| ggtcaacttc cgtaccgagc cgcaggaacc gcaggagtgg acggacgacc tcgtccgtct | 5340 |
| gcgggagcgc tatccctggc tcgtcgccga ggtggacggc gaggtcgccg gcatcgccta | 5400 |
| cgcgggcccc tggaaggcac gcaacgccta cgactggacg gccgagtcga ccgtgtacgt | 5460 |
| ctcccccgc caccagcgga cgggactggg ctccacgctc tacacccacc tgctgaagtc | 5520 |
| cctggaggca cagggcttca agagcgtggt cgctgtcatc gggctgccca acgacccgag | 5580 |
| cgtgcgcatg cacgaggcgc tcggatatgc ccccgcgc atgctgcggg cggccggctt | 5640 |
| caagcacggg aactggcatg acgtgggttt ctggcagctg gacttcagcc tgccggtacc | 5700 |
| gccccgtccg gtcctgcccg tcaccgagat ctgatctcac ccgtctagga tccccgatg | 5760 |
| agctaagcta gctatatcat caatttatgt attacacata atatcgcact cagtctttca | 5820 |
| tctacggcaa tgtaccagct gatataatca gttattgaaa tatttctgaa tttaaacttg | 5880 |
| catcaataaa tttatgtttt tgcttggact ataatacctg acttgttatt ttatcaataa | 5940 |
| atatttaaac tatatttctt tcaagataaa cataacttcg tatagcatac attatacgaa | 6000 |
| gttatcaaaa cgtcgtgaga cagtttggtt aactataacg gtcctaaggt agcgatcgag | 6060 |
| gcattacggc attacggcac tcgcgagggt ccgaatctat gtcgggtgcg agaaagagg | 6120 |
| taatgaaatg gcaattcgag catggagcca tttacaattg aatatatcct gccg | 6174 |

```
<210> SEQ ID NO 2
<211> LENGTH: 975
<212> TYPE: DNA
<213> ORGANISM: Brassica napus

<400> SEQUENCE: 2
```

| | |
|---|---|
| caggtttgga ttggtttggg tattagaatc caaaaaaaca cgaagtatcc aaaacacaaa | 60 |
| aaaagacttg aaacacaaaa atacccgaaa tccaaacaaa tacctgaaaa tattcatata | 120 |
| ctcaaaagat ccaaaaattt acccgtaaac ctaatccgga gaacccaaaa cacccaaaat | 180 |
| tttaccaacc caaaatatat ttttctaaaa ttgaaatttt atccataacc tcaaactata | 240 |
| accgaaaaac cttaaccata aacttaaaaa tatttgtaat gccgaaaaca tatatgaaat | 300 |
| atccaaacat acctaatata cacaaatcat tccaggtact tgggtaccca atcgagtctc | 360 |
| ggatatgacc taaactggag caaagattcg cggtccaaaa agatattgaa taggtacttt | 420 |
| gcccatgatt cagacccgaa ctgcacctgt atttcgggt tggtttcgga tttagttttt | 480 |
| caggtccgac aaactgtaga atcgtatgaa aaaattagat agaaatatat agataaaatc | 540 |
| tgaaataata atgtataaca atctcaaaaa attaattcat ataaaacttt tttataataa | 600 |
| aaaaaccgcg ctttttaagag agtcaaaatc tagtaagttt attaaaaatg aatttcagtt | 660 |
| tttagttaaa tgactaacaa attggaacat ctggtgtaaa atggctgttg gctgggagta | 720 |
| aataagtgt gtgaaaagaa gatagccgtt aagtccattg catgtcgaaa cgtgtaaaaa | 780 |
| agaaagagga gcaaaaccaa aacgcttcaa attaatttgc atattctcta gagaatccat | 840 |

```
gcaggaaaaa gtttcaccta acggctatga cttctctact ttcaccataa atacacatac    900
aagcaccgaa gagcaacaca gacttcaaga gatcagtgag taattacttt gaggtttagt    960
taaaacttttt gggga                                                    975
```

<210> SEQ ID NO 3
<211> LENGTH: 975
<212> TYPE: DNA
<213> ORGANISM: Brassica napus

<400> SEQUENCE: 3

```
tggttccaca aaggccaagc aattatcaca gagcttcaat atagtcaatg gtgggcattt     60
cactaaagtg tgatcagctc aatagtgata agaagataaa tctaaaacac aaacctggtc    120
gctccattat cgagtttcga actctgatcc caaaacccct agaggttcca gcttttccat    180
ctcacaactt ctagtgaaac tagggtttgg gttttctgca gactgtagag aagcagtag     240
aagattgctg gctgtatcag aagctaaata gacgtggctg aagaatattt tgaagcttca    300
caattagctc ctctctaagc taggcatact gaagaaagca tccatccact tatagaaata    360
gttgggcttt aaacgtagag gatgaaatat gttctgttac aagaaaatag taaatagttt    420
attctaatat tgtccaacta gttgggctgc aaatatagag gataaaatcc ttaaagcctt    480
tcttttaaca tacttgatca tttaaaagca cattagtttt ttaattattt tgaactcctt    540
ctagttggtt ttttttaggct tttagctcat tgtatactt ttttttttctt atataaaatg    600
aagacaatac gttacgcaag ttattttttt aagaaaattg aatttcagct ttatattaaa    660
tgactgacaa attagaagat ctagttttaa atggttgttt gtgatttgag gagggagtaa    720
atgaaatgtg tgaaaagaag agagatggcc gttaagtcca ttgcatgttg aaacgtgtga    780
agaaaacaaa agaggagcaa aacttgaaac gcttcttatt aattttgcat attctctaga    840
gagtcgaagt tgatgcagcc aaaagctaac ggctatgact tctctacttt cactataaat    900
acgcatacaa gcactgaaga gcaacacaca tttcaagaga ctgatttatt tgaggtctag    960
ttaaagtttg gaggg                                                    975
```

<210> SEQ ID NO 4
<211> LENGTH: 975
<212> TYPE: DNA
<213> ORGANISM: Brassica napus

<400> SEQUENCE: 4

```
tatccacttg tagaaaatga aagttattca agttttgtct aactagttgt atcgagagaa     60
aatatgtaac gccttgatct tgttgaaaaa aagcccattt cactttattg tatttaactc    120
cttttttagct aaaacaatat gactactttt tcttttatgaa ataaaaacaa tacatttttg    180
acttaatttta ttaatttatt ataaatcatt agaattcaca actctattat atttttggaca    240
cttttgtttta taagaatttt acatctaacc gttctatttc cttttcttata aatccgcatt    300
gcaagttcta tttacaattg cacaatgtca aatttttttat tattattagg tatgtctagg    360
tttggatggt acatgttaga tcgtaactat gattggttca cttttctgata ttaaatgtgt    420
ttttttcgag ccgactagat caaccgatag aattgatcaa aaaaaattat taaatttttt    480
tatattagtc tgcattaaac aacattgtgt cggcctcaaa tttcagacat ctgattatct    540
gaaaataaaa atactaataa tctcttagct aaatcatttc actatgtgat cttccacaaa    600
ataaaataat acgttatgta attatgtaag cttattaaca attgatttca tttttttgt     660
```

```
tttgttagat gactaacaaa ttggaacatc tgttggaaaa tggctgtttg cggggagtaa      720
ataaagtgtg tgaaaagaag atagccgtta agtccattgc atgtcgaaac gtgtaaaaaa      780
ggaagaggag caaagccaaa acgcttcaaa ttaatttgca tattctcaag ataacccatg      840
caggcaaaag cttcatctaa cggctatgac ttatctgctt tcaccataaa tacacataca      900
agcacccaag agcaacacag agttcaagag atcagtgagt aattgtttta aggtttagtt      960
acaagttttg gagag                                                      975
```

```
<210> SEQ ID NO 5
<211> LENGTH: 975
<212> TYPE: DNA
<213> ORGANISM: Brassica napus

<400> SEQUENCE: 5
tggttccaca aaggccaagc aattatcaca gagcttcaat atagtcaatg gtgggcattt       60
cactaaagtg tgatcagctc aatagtgata agaagataaa tctaaaacac aaacctggtc      120
gctccattat cgagtttcga actctgatcc caaaacccct agaggttcca gcttttccat      180
ctcacaactt ctagtgaaac tagggtttgg gttttctgca gactgtagag gaagcagtag      240
aagattgctg gctgtatcag aagctaaata gacgtggctg aagaatattt tgaagcttca      300
caattagctc ctctctaagc taggcatact gaagaaagca tccatccact tatagaaata      360
gttgggcttt aaacgtagag gatgaaatat gttctgttac aagaaaatag taaatagttt      420
attctaatat tgtccaacta gttgggctgc aaatatagag gataaaatcc ttaaagcctt      480
tcttttaaca tacttgatca tttaaaagca cattagtttt ttaattattt tgaactcctt      540
ctagttggtt tttttaggct tttagctcat ttgtatactt tttttttctt atataaaatg      600
aagacaatac gttacgcaag ttatttttt aagaaaattg aatttcagct ttatattaaa      660
tgactgacaa attagaagat ctagtttaa atggttgttt gtgatttgag gagggagtaa      720
atgaaatgtg tgaaaagaag agagatggcc gttaagtcca ttgcatgttg aaacgtgtga      780
agaaaacaaa agaggagcaa aacttgaaac gcttcttatt aattttgcat attctctaga      840
gagtcgaagt tgatgcagcc aaaagctaac ggctatgact tctctacttt cactataaat      900
acgcatacaa gcactgaaga gcaacacaca tttcaagaga ctgatttatt tgaggtctag      960
ttaaagtttg gaggg                                                      975
```

```
<210> SEQ ID NO 6
<211> LENGTH: 975
<212> TYPE: DNA
<213> ORGANISM: Brassica oleracea

<400> SEQUENCE: 6
aggtttggat tggtttgggt attagaatcc aaaaaaacac gaagtatcca aaacacaaaa       60
aaagacttga acacaaaaa tacccgaaat ccaaacaaat acctgaaaat attcatatac      120
tcaaaagatc caaaaattta cccgtaaacc taatccggag aacccaaaac acccaaaatt      180
ttaccaaccc aaaatatatt tttctaaaat tgaattttta tccataacct caaactataa      240
ccgaaaaacc ttaaccataa acttaaaaat atttgtaatg ccgaaaacat atatgaaata      300
tccaaacata cctaatatac acaaatcatt ccaggtactt gggtacccaa tcgagtctcg      360
gatatgacct aaactggagc aaagattcgc ggtccaaaaa gatattgaat aggtactttg      420
cccatgattc agacccgaac tgcacctgta ttttcgggtt ggtttcggat ttagtttttc      480
agatccgaca aactgtagaa tcgtatgaaa aaattagata gaaatatata gataaaatct      540
```

| gaaataataa tgtataacaa tctcaaaaaa ttaattcata taaaacttttt ttataataaa | 600 |
| aaaaccgcgc ttttaagaga gtcaaaatct agtaagttta ttaaaaatga atttcagttt | 660 |
| ttagttaaat gactaacaaa ttggaacatc tggtgtaaaa tggctgttgg ctgggagtaa | 720 |
| ataaagtgtg tgaaagaag atagccgtta agtccattgc atgtcgaaac gtgtaaaaaa | 780 |
| gaaagaggag caaaaccaaa acgcttcaaa ttaatttgca tattctctag agaatccatg | 840 |
| caggaaaaag tttcacctaa cggctatgac ttctctactt tcaccataaa tacacataca | 900 |
| agcaccgaag agcaacacag acttcaagag atcagtgagt aattactttg aggtttagtt | 960 |
| aaaactttg gggag | 975 |

<210> SEQ ID NO 7
<211> LENGTH: 975
<212> TYPE: DNA
<213> ORGANISM: Brassica oleracea

<400> SEQUENCE: 7

| atggtgggca attcactaaa gtgtgatcag ctcaatagtg ataagaagat aaatctaaaa | 60 |
| cacaaacctg gtcgctccat tatcgagttt cgaactctga tcccaaaacc cctagaggtt | 120 |
| ccagcttttc catctcacaa cttctagtga aactagggtt tgggttttct gcagactgta | 180 |
| gaggaagcag tagaagattg ttggctgtat cagaagctaa atagacgtgg ctgaagaata | 240 |
| ttttgaagct tcacaattag ctcctctcta agctaggcat actgaagaaa gcatccattc | 300 |
| acttatagaa atagttgggc tttaaaagta gaggatgaaa tgtgttatgt tacgttgaca | 360 |
| aaaaaagaa agaaatgtg ttatgttaca tgaaaatagt agaaagttta ttctaatatt | 420 |
| gcccaactag ttgggctgta aatatagagg ataaaatctt taaagccttt cttttaacat | 480 |
| acttgatcat ttacaaaagc acattagttt tttaattatt ttgaactcgt agttggtttt | 540 |
| ttaggctttt agctcatttg tatactttct gtccagagtt aagactctct ttttctttat | 600 |
| ataaaatgaa gacaatacgt tacgcaagtt atttaaaaaa aaaaattaaa tttcagcttt | 660 |
| atattaaatg actgacaaat tagaagatct agtttcaaat ggttgtttgt gatttgagga | 720 |
| gggagtaaat aaaaattgtg aaaagaagag agatggccgt taagtccatt gcatgttgaa | 780 |
| acgtgtgaag aaaacaaaag aggagcaaaa cttgaaacgc ttcttattaa ttttgcatgt | 840 |
| tctctagaga gtcgaagttg atgcagccaa aagttaacgg ctatgacttc tctactttca | 900 |
| ctataaatac gcactgaaga gcaacacaca tttcaagaga ctgatttatt tgaggtctag | 960 |
| tcaaagtttg gagag | 975 |

<210> SEQ ID NO 8
<211> LENGTH: 975
<212> TYPE: DNA
<213> ORGANISM: Brassica rapa

<400> SEQUENCE: 8

| gaaagttatt caagttttgt ctaactagtt gtatcgagag aaaatatgta acgccttgat | 60 |
| cttgttgaaa aaagcccatt tcactttatt gtatttaact cctttttagc tacaacaata | 120 |
| tgactacttt ttctttatga aataaaaaca atacattttt aacttaattt attaatttat | 180 |
| tataaatcat tagaattcac aactctatta tattttggac actttgtttt ataagaattt | 240 |
| tacatctaac cgttctattt cctttcttat aaatccgcat tgcaagttct atttacaatt | 300 |
| gcacaatgtc aaatttttca ttattattag gtacgtctag gtttggactt ctgtccaaat | 360 |

| | |
|---|---:|
| ggtatatgtt agatcgtaac taatgatcgg ttcactttct gatatttctg atattaagta | 420 |
| tgttttttcc aagccggcta gatcagccga taggatttat taaaaaaaat tattaaattt | 480 |
| tttatattag tctgcattaa acgacattgt gatcggcctc aaatttcaga catctgatta | 540 |
| tctgaaaata aaaatactaa taatctctta gctaaatcat ttcactatgt gatcttccac | 600 |
| aaaataaaat aatacgttat gtaattatgt aagcttatta acaattgatt tcattttttt | 660 |
| tttgttagat gactaacaaa ttggaacatc tgttggaaaa tggctgtttg cggggagtaa | 720 |
| ataaagtgtg tgaaaagaaa atagccgtta agtccattgc atgtcgaaac gtgtaaaaaa | 780 |
| ggaagaggag caaaaccaaa acgcttcaaa ttaatttgca tattctctag ataacccatg | 840 |
| caggcaaaag cttcatctaa cggctatgac ttctctgctt tcaccataaa tacacataca | 900 |
| agcacccaag agcaacacag agttcaagag atcagtgagt aattgtttta aggtttagtt | 960 |
| acaagttttg gagag | 975 |

<210> SEQ ID NO 9
<211> LENGTH: 975
<212> TYPE: DNA
<213> ORGANISM: Brassica rapa

<400> SEQUENCE: 9

| | |
|---|---:|
| gatcgaaccg aaccgactga accgaaaccg atttgaacca aaccaaagtc catttcaaat | 60 |
| cattcggttg aagattttcc caacccgaat ggttcagttc agttcagttt aaaccgaacc | 120 |
| aaaccgataa accgaagtgt tttatagtt atttaaatta aaaatattag tgatatcaag | 180 |
| atattaaaat cctaagactt agcccaagta atttcctttt gcacgaagga atcctaata | 240 |
| taatttgatt tccatgacac ttcgtctaac ttttgtaata tttgtcatta agcccacata | 300 |
| atttccatgt taattgttat aaagttataa actatatttg taactttaa aaagattttt | 360 |
| atttggttta atattgaatt taatttacat acttaatttt tttattatga ccaacgcgat | 420 |
| tatttcatga caaccataca tttatgtatt aaaacatgat ttcttgtaca ataaataaac | 480 |
| taagagaaat ccgattaaac cgaatcgaac cgaaatacta actaaatcga atacaaaccg | 540 |
| aaccgaatat aaaccgaacc gaacataact gaaccgaaat cgatccaaac caaaccaact | 600 |
| atggtttact tcagctggaa aaattctaga accgaactaa ccaaaccgaa ccgaactcga | 660 |
| accgaaccga taaataaacc gaagtgccca ccccctagttt gtgatttgag gaggggagtaa | 720 |
| atgaattgtg tgaaaagaag agagatggcc gttaagtcca ttgcatgttg aaacgtgtga | 780 |
| agaaaacaaa agaggagcaa aacttgaaac gcttcttatt aattttgcat attctctaga | 840 |
| gagtcgaagt tgatgcagcc aaaagctaac ggctatgact tctctacttt cactataaat | 900 |
| acgcatacaa gcactgaaga gcaacacaca tttcaagaga ttgatttatt tgaggtctag | 960 |
| ttaaagtttg gaggg | 975 |

<210> SEQ ID NO 10
<211> LENGTH: 975
<212> TYPE: DNA
<213> ORGANISM: Brassica juncea

<400> SEQUENCE: 10

| | |
|---|---:|
| ttctggattt taatttggtt aaatgtcaat gtaaaatagt ttataattta atttaaagat | 60 |
| aataaaccaa ttgatcatgg tttatatatg ggtttttaga tttaaactt taaaattatg | 120 |
| agaagtaaat ctaaaactat tgtttcggag atatagagaa caagattata atttgagaga | 180 |
| catctaatat gctatacggt agttacataa gaagatagtt tgtcgatcca atttttaatt | 240 |

```
tattttattg aactcctttt agctagcttg tagtacattt ttctgtggag gattagtact      300
taaggtttct ctgtgtgtgt aaaaatatga taataagttt tttaatatct gattcagtat      360
cgatcctact agaaattatg aaagctatca tatacaaccg gtaattttac tttaagttat      420
ttaggtgagt gttacaaaaa aaagttattt aggtgaatat acatagattt atatggacta      480
tattaaaatg ttattgaaat atctataaat ctgcataatt ataaataaaa taatattttg      540
tattgaatca aatatacagt taaaaacatt aatgaacttt taataaaata attgcactaa      600
agagcttcca cataaaaaca gtttagaaa  aataaatttc agtatttagt taaatgacta      660
ataaatcgga gcatcaggtg aaaaaaaaag gctgtttgtg ctttgctagg gagtatataa      720
aagaaagtga aagaagata  gccgttaagt ccattgcatg tcgaaacgtg taaaaaagaa      780
gagaagcaaa accaaaacgc ttcaaattag tttgcacatt ctctagagaa tccatgcagc      840
caaacgcttc acctaacggc tattacttct ctacttccac cataaataca catacatgca      900
agcacccaag aggcaagagc aaacacagag ttcaagagag cgaatacttg aggtttagtt      960
aaaagatttg gaaag                                                      975

<210> SEQ ID NO 11
<211> LENGTH: 975
<212> TYPE: DNA
<213> ORGANISM: Brassica juncea

<400> SEQUENCE: 11
tggttccaca aaggccaagc aattatcaca gagcttcaat atagtcaatg gtgggcattt       60
cactaaagtg tgatcagctc aatagtgata agaagataaa tctaaaacac aaacctggtc      120
gctccattat cgagtttcga actctgatcc caaaaccccct agaggttcca gcttttccat     180
ctcacaactt ctagtgaaac taggtttgg  gttttctgca gactgtagag gaagcagtag      240
aagattgctg gctgtatcag aagctaaata gacgtggctg aagaatattt tgaagcttca      300
caattagctc ctctctaagc taggcatact gaagaaagca tccatccact tatagaaata      360
gttgggcttt aaacgtagag gatgaaatat gttctgttac aagaaaatag taaatagttt      420
attctaatat tgtccaacta gttgggctgc aaatatagag gataaaatcc ttaaagcctt      480
tcttttaaca tacttgatca tttaaaagca cattagtttt ttaattattt tgaactcctt      540
ctagttggtt ttttaggct  tttagctcat ttgtatactt ttttttcttt atataaaatg      600
aagacaatac gttacgcaag ttatttttt  aagaaaattg aatttcagct ttatattaaa      660
tgactgacaa attagaagat ctagttttaa atggttgttt gtgatttgag gagggagtaa      720
atgaaatgtg tgaaaagaag agagatggcc gttaagtcca ttgcatgttg aaacgtgtga      780
agaaaacaaa agaggagcaa aacttgaaac gcttcttatt aattttgcat attctctaga      840
gagtcgaagt tgatgcagcc aaaagctaac ggctatgact tctctacttt cactataaat      900
acgcatacaa gcactgaaga gcaacacaca tttcaagaga ctgatttatt tgaggtctag      960
ttaaagtttg gaggg                                                      975

<210> SEQ ID NO 12
<211> LENGTH: 975
<212> TYPE: DNA
<213> ORGANISM: Brassica juncea

<400> SEQUENCE: 12
tatccacttg tagaaaatga aagttattca agttttgtct aactagttgt atcgagagaa       60
```

```
aatatgtaac gccttgatct tgttgaaaaa aagcccattt cactttattg tatttaactc    120 cttttttagct aaaacaatat gactactttt tctttatgaa ataaaaacaa tacattttg    180 acttaattta ttaatttatt ataaatcatt agaattcaca actctattat attttggaca    240
ctttgtttta taagaatttt acatctaacc gttctatttc ctttcttata aatccgcatt    300
gcaagttcta tttacaattg cacaatgtca aatttttat tattattagg tatgtctagg     360
tttggatggt acatgttaga tcgtaactat gattggttca ctttctgata ttaaatgtgt    420
ttttttcgag ccgactagat caaccgatag aattgatcaa aaaaaattat taaattttt    480 tatattagtc tgcattaaac aacattgtgt cggcctcaaa tttcagacat ctgattatct    540
gaaaataaaa atactaataa tctcttagct aaatcatttc actatgtgat cttccacaaa    600
ataaaataat acgttatgta attatgtaag cttattaaca attgatttca ttttttttgt    660
tttgttagat gactaacaaa ttggaacatc tgttggaaaa tggctgtttg cggggagtaa    720
ataaagtgtg tgaaaagaag atagccgtta agtccattgc atgtcgaaac gtgtaaaaaa    780
ggaagaggag caaagccaaa acgcttcaaa ttaatttgca tattctcaag ataacccatg    840
caggcaaaag cttcatctaa cggctatgac ttctctgctt tcaccataaa tacacataca    900
agcacccaag agcaacacag agttcaagag atcagtgagt aattgtttta aggtttagtt    960
acaagttttg gagag                                                    975
```

<210> SEQ ID NO 13
<211> LENGTH: 975
<212> TYPE: DNA
<213> ORGANISM: Brassica juncea

<400> SEQUENCE: 13

```
atttgttaat gcttcacaac caactctctc tctaacttac ctcttgttga acaagtccaa     60
actttgtctc tgttttttccc tgtttttttct ttaaattagt taaccgttct ttcctgataa    120
accaaggttc aatgttggat tgagatagtg gtttagttta acttcttgtt atgttttttt    180 ttttttttgat aaaaatgact ttttcttgtt ggaatatcgc attctccggt ctttcttacg    240
ccttcccata aacattttag ttaacaaaaa attaatagaa aatttagtgt aatgttttaa    300
gttaataaca tgactagaaa tggaatttca tttcaccatt gagggaggaa atgttttcc    360 ttacaagaaa ataattaaag tttgttataa tagtgtccaa ctagttgggc tgtacatata    420
gaagagaaca tgtgtaaagc ctttcttata agttataaca tacctgatcc atttgaaaaa    480
gcccgttaat tttttattgt attgaactcc tactctcttt cttacaaaat ggaactccta    540
cttggtttta gcttttgtat atttctgtcc agaatttaat actttgtatt tcttttaata    600
taaaatataa aaattaagac agtacgttac gtaattttaa acagacatgg atttcaggtt    660
taaattaaat gactaacaaa ttagaagatc tagttttaaa tggttttttt cttcttggag    720
aggggggtgg taaacaaaaa gtgtgaaaag aagatatccg ttaagtccat tgcatgtcga    780
aacgtgtgaa aaaatgacca acactgaaac gcttctaatt aattttgcat atattatcta    840
gagattcgat gcagccaaaa gcttcaccca acggctatga gttctctact ttccataaa    900 atacacatca aatcacccaa gagtaacaca gttcaaaaga gtaatttact tgaggtctag    960 ttaaattta gagag                                                    975
```

<210> SEQ ID NO 14
<211> LENGTH: 206
<212> TYPE: PRT
<213> ORGANISM: Brassica napus

<400> SEQUENCE: 14

```
Met Gly Leu Val Lys Ser Phe Asp Ala Tyr Leu Met Ile Val Met Leu
1               5                   10                  15

Thr Gly Leu Val Phe Ala Leu Gly Leu Ser Asn Gly Tyr Lys Phe Tyr
            20                  25                  30

Val Gly Gly Lys Asp Gly Trp Val Leu Thr Pro Ser Glu Asp Tyr Ser
        35                  40                  45

His Trp Ser His Arg Asn Arg Phe Gln Val Asn Asp Thr Leu Tyr Phe
    50                  55                  60

Lys Tyr Pro Lys Gly Lys Asp Ser Val Val Glu Val Ser Glu Glu Glu
65                  70                  75                  80

Tyr Asn Thr Cys Asn Thr Thr His Pro Ile Thr Ser Leu Ser Asp Gly
                85                  90                  95

Asp Ser Leu Phe Val Leu Ser Arg Ser Gly Pro Phe Phe Phe Val Ser
            100                 105                 110

Gly Asn Ser Glu Asn Cys Leu Lys Gly Gln Lys Leu Ala Val Asn Val
        115                 120                 125

Met Ser Thr Ala His His Ser Arg Ser Pro Arg Gln Pro Ser Pro Ser
    130                 135                 140

Pro Ser Pro Thr Leu Ser Pro Val Ala Trp Ser Ser Pro Ala Pro Ser
145                 150                 155                 160

Pro Gly Val Glu Leu Ser Asp Ser Glu Ala Leu Ala Pro Ala Ser Glu
            165                 170                 175

Pro Ala Lys Ala Arg Asn Ser Ala Ser Leu Val Gly Pro Gly Met Val
        180                 185                 190

Ser Leu Gly Leu Val Leu Val Val Phe Ile Arg Ser Met Val
    195                 200                 205
```

<210> SEQ ID NO 15
<211> LENGTH: 210
<212> TYPE: PRT
<213> ORGANISM: Brassica napus

<400> SEQUENCE: 15

```
Met Gly Leu Ile Lys Arg Phe Asp Ala Tyr Leu Met Thr Val Met Leu
1               5                   10                  15

Val Ser Leu Gly Phe Ala Ile Gly Phe Ser Asn Gly Tyr Lys Phe Tyr
            20                  25                  30

Val Gly Gly Arg Asp Gly Trp Val Leu Thr Pro Ser Glu Asp Tyr Ser
        35                  40                  45

His Trp Ser Tyr Arg Ser Arg Phe Gln Val Asn Asp Thr Leu Tyr Phe
    50                  55                  60

Lys Tyr Pro Lys Gly Lys Asp Ser Val Leu Glu Val Ser Glu Glu Glu
65                  70                  75                  80

Phe Asn Thr Cys Asn Thr Thr His Pro Ile Thr Ser Leu Thr Asp Gly
                85                  90                  95

Asp Ser Leu Tyr Val Leu Ser Arg Ser Gly Pro Phe Phe Phe Val Ser
            100                 105                 110

Gly Asn Ser Glu Asn Cys Leu Lys Gly Gln Lys Leu Pro Val Lys Val
        115                 120                 125

Met Ser Thr Ala His His Ser His Ser Pro Arg Gln Pro Ser Pro Ser
    130                 135                 140

Pro Ser Pro Ser Ser Thr Leu Ser Pro Ser His Gln Ala Leu Ser Ser
145                 150                 155                 160
```

Pro Ala Pro Ser Pro Arg Val Val Leu Ser Glu Ser Glu Ala Leu Ala
            165                 170                 175

Pro Ala Pro Gly Pro Ala Lys Ala His Asn Ser Ala Gly Leu Val Ser
        180                 185                 190

Pro Arg Gly Val Ser Leu Gly Leu Val Leu Val Val Ile Ile Ser Phe
    195                 200                 205

Met Val
    210

<210> SEQ ID NO 16
<211> LENGTH: 210
<212> TYPE: PRT
<213> ORGANISM: Brassica napus

<400> SEQUENCE: 16

Met Gly Leu Val Lys Thr Phe Asp Val Tyr Leu Met Ile Val Met Leu
1               5                   10                  15

Ala Gly Leu Val Phe Ala Leu Gly Leu Ser Asn Gly Tyr Lys Phe Tyr
            20                  25                  30

Val Gly Gly Lys Asp Gly Trp Val Leu Thr Pro Ser Glu Asp Tyr Ser
        35                  40                  45

His Trp Ser His Arg Asn Arg Phe Gln Val Asn Asp Thr Leu Tyr Phe
    50                  55                  60

Lys Tyr Pro Lys Gly Lys Asp Ser Val Leu Glu Val Ser Glu Glu Glu
65                  70                  75                  80

Tyr Asn Thr Cys Asn Thr Thr His Pro Ile Thr Ser Val Ser Asp Gly
                85                  90                  95

Gly Ser Leu Phe Val Leu Ser Arg Ser Gly Pro Phe Phe Phe Val Ser
            100                 105                 110

Gly Asn Ser Glu Asn Cys Leu Lys Gly Gln Lys Leu Ala Val Asn Val
        115                 120                 125

Met Ser Thr Ala His His Ser Arg Ser Pro Arg Gln Pro Ser Pro Ser
    130                 135                 140

Pro Ser Pro Ser Pro Ser Pro Thr Leu Ser Pro Ile Ala Trp Ser Ser
145                 150                 155                 160

Pro Ala Pro Ser Pro Gly Val Val Leu Ser Asp Ser Glu Ala Leu Ala
            165                 170                 175

Pro Ala Pro Glu Pro Ala Lys Ala Arg Asn Ser Ala Cys Leu Val Gly
        180                 185                 190

Pro Gly Met Val Ser Leu Gly Leu Val Leu Phe Val Phe Ile Arg Ser
    195                 200                 205

Met Val
    210

<210> SEQ ID NO 17
<211> LENGTH: 210
<212> TYPE: PRT
<213> ORGANISM: Brassica napus

<400> SEQUENCE: 17

Met Gly Leu Ile Lys Arg Phe Asp Ala Tyr Leu Met Thr Val Met Leu
1               5                   10                  15

Met Ser Leu Gly Phe Ala Ile Gly Phe Ser Asn Gly Tyr Lys Phe Tyr
            20                  25                  30

Val Gly Gly Arg Asp Gly Trp Val Leu Thr Pro Ser Glu Asp Tyr Ser
        35                  40                  45

His Trp Ser Tyr Arg Ser Arg Phe Gln Val Asn Asp Thr Leu Tyr Phe
            50                  55                  60

Lys Tyr Pro Lys Gly Lys Asp Ser Val Leu Glu Val Ser Glu Glu Glu
 65                  70                  75                  80

Phe Asn Thr Cys Asn Thr Thr His Pro Ile Thr Ser Leu Thr Asp Gly
                 85                  90                  95

Asp Ser Leu Tyr Val Leu Ser Arg Ser Gly Pro Phe Phe Phe Val Ser
                100                 105                 110

Gly Asn Ser Glu Asn Cys Leu Lys Gly Gln Lys Leu Pro Val Lys Val
                115                 120                 125

Met Ser Ala Ala His His Ser His Ser Pro Arg Gln Pro Ser Pro Ser
            130                 135                 140

Pro Ser Pro Ser Pro Thr Leu Ser Pro Ser His Gln Ala Leu Ser Ser
145                 150                 155                 160

Pro Ala Pro Ser Pro Arg Val Val Leu Ser Glu Ser Glu Ala Leu Ala
                165                 170                 175

Pro Ala Pro Gly Pro Ala Lys Ala His Asn Ser Ala Gly Leu Val Ser
                180                 185                 190

Pro Arg Ala Val Ser Leu Gly Leu Val Leu Val Ile Ile Ser Phe
                195                 200                 205

Val Leu
    210

<210> SEQ ID NO 18
<211> LENGTH: 211
<212> TYPE: PRT
<213> ORGANISM: Brassica oleracea

<400> SEQUENCE: 18

Met Gly Leu Ile Lys Arg Phe Asp Ala Tyr Leu Met Thr Val Met Leu
 1               5                  10                  15

Met Ser Leu Gly Leu Phe Ala Ile Gly Phe Ser Asn Gly Tyr Lys Phe
                 20                  25                  30

Tyr Val Gly Gly Arg Asp Gly Trp Val Leu Thr Pro Ser Glu Asp Tyr
             35                  40                  45

Ser His Trp Ser Tyr Arg Ser Arg Phe Gln Val Asn Asp Thr Leu Tyr
         50                  55                  60

Phe Lys Tyr Pro Lys Gly Lys Asp Ser Val Leu Glu Val Ser Glu Glu
 65                  70                  75                  80

Glu Phe Asn Thr Cys Asn Thr Thr His Pro Ile Thr Ser Leu Thr Asp
                 85                  90                  95

Gly Asp Ser Leu Tyr Val Leu Ser Arg Ser Gly Pro Phe Phe Phe Val
                100                 105                 110

Ser Gly Asn Ser Glu Asn Cys Leu Lys Gly Gln Lys Leu Pro Val Lys
                115                 120                 125

Val Met Ser Ala Ala His His Ser His Ser Pro Arg Gln Pro Ser Pro
            130                 135                 140

Ser Pro Ser Pro Ser Pro Thr Leu Ser Pro Ser His Gln Ala Leu Ser
145                 150                 155                 160

Ser Pro Ala Pro Ser Pro Arg Val Val Leu Ser Glu Ser Glu Ala Leu
                165                 170                 175

Ala Pro Ala Pro Gly Pro Ala Lys Ala His Asn Ser Ala Gly Leu Val
                180                 185                 190

Ser Pro Arg Ala Val Ser Leu Gly Leu Val Leu Val Val Ile Ile Ser

Phe Val Val
    210

<210> SEQ ID NO 19
<211> LENGTH: 206
<212> TYPE: PRT
<213> ORGANISM: Brassica oleracea

<400> SEQUENCE: 19

Met Gly Leu Val Lys Ser Phe Asp Ala Tyr Leu Met Ile Val Met Leu
1               5                   10                  15

Thr Gly Leu Val Phe Ala Leu Gly Leu Ser Asn Gly Tyr Lys Phe Tyr
            20                  25                  30

Val Gly Gly Lys Asp Gly Trp Val Leu Thr Pro Ser Glu Asp Tyr Ser
        35                  40                  45

His Trp Ser His Arg Asn Arg Phe Gln Val Asn Asp Thr Leu Tyr Phe
    50                  55                  60

Lys Tyr Pro Lys Gly Lys Asp Ser Val Val Glu Val Ser Glu Glu Glu
65                  70                  75                  80

Tyr Asn Thr Cys Asn Thr Thr His Pro Ile Thr Ser Leu Ser Asp Gly
                85                  90                  95

Asp Ser Leu Phe Val Leu Ser Arg Ser Gly Pro Phe Phe Val Ser
            100                 105                 110

Gly Asn Ser Glu Asn Cys Leu Lys Gly Gln Lys Leu Ala Val Asn Val
        115                 120                 125

Met Ser Thr Ala His His Ser Arg Ser Pro Arg Gln Pro Ser Pro Ser
    130                 135                 140

Pro Ser Pro Thr Leu Ser Pro Val Ala Trp Ser Ser Pro Ala Pro Ser
145                 150                 155                 160

Pro Gly Val Glu Leu Ser Asp Ser Glu Ala Leu Ala Pro Ala Ser Glu
                165                 170                 175

Pro Ala Lys Ala Arg Asn Ser Ala Ser Leu Val Gly Pro Gly Met Val
            180                 185                 190

Ser Leu Gly Leu Val Leu Val Val Phe Ile Arg Ser Met Val
        195                 200                 205

<210> SEQ ID NO 20
<211> LENGTH: 212
<212> TYPE: PRT
<213> ORGANISM: Brassica rapa

<400> SEQUENCE: 20

Met Gly Leu Val Lys Thr Phe Asp Ala Tyr Leu Met Ile Val Met Leu
1               5                   10                  15

Ala Gly Leu Val Phe Ala Leu Gly Leu Ser Asn Gly Tyr Lys Phe Tyr
            20                  25                  30

Val Gly Gly Lys Asp Gly Trp Val Leu Thr Pro Ser Glu Asp Tyr Ser
        35                  40                  45

His Trp Ser His Arg Asn Arg Phe Gln Val Asn Asp Thr Leu Tyr Phe
    50                  55                  60

Lys Tyr Pro Lys Gly Lys Asp Ser Val Leu Glu Val Ser Glu Glu Glu
65                  70                  75                  80

Tyr Asn Thr Cys Asn Thr Thr His Pro Ile Thr Ser Val Ser Asp Gly
                85                  90                  95

Gly Ser Leu Phe Val Leu Ser Asn Ser Gly Pro Phe Phe Val Ser

```
                   100                 105                 110
Gly Asn Ser Glu Asn Cys Leu Lys Gly Gln Lys Leu Ala Val Asn Val
                115                 120                 125

Met Ser Thr Ala His His Ser Arg Ser Pro Arg Gln Pro Ser Pro Ser
    130                 135                 140

Pro Ser Pro Ser Pro Ser Pro Ser Pro Thr Leu Ser Pro Ile Ala Trp
145                 150                 155                 160

Ser Ser Pro Ala Pro Ser Pro Gly Val Val Leu Ser Asp Ser Glu Ala
                165                 170                 175

Leu Ala Pro Ala Pro Glu Pro Ala Lys Ala Arg Asn Ser Ala Cys Leu
            180                 185                 190

Val Gly Pro Gly Met Val Ser Leu Gly Leu Val Leu Phe Val Phe Ile
            195                 200                 205

Arg Ser Met Val
    210

<210> SEQ ID NO 21
<211> LENGTH: 210
<212> TYPE: PRT
<213> ORGANISM: Brassica rapa

<400> SEQUENCE: 21

Met Gly Leu Ile Lys Arg Phe Asp Ala Tyr Leu Met Thr Val Met Leu
1               5                  10                  15

Met Ser Leu Gly Phe Ala Ile Gly Phe Ser Asn Gly Tyr Lys Phe Tyr
                20                  25                  30

Val Gly Gly Arg Asp Gly Trp Val Leu Thr Pro Ser Glu Asp Tyr Ser
            35                  40                  45

His Trp Ser Tyr Arg Ser Arg Phe Gln Val Asn Asp Thr Leu Tyr Phe
        50                  55                  60

Lys Tyr Pro Lys Gly Lys Asp Ser Val Leu Glu Val Ser Glu Glu Glu
65                  70                  75                  80

Phe Asn Thr Cys Asn Thr Thr His Pro Ile Thr Ser Leu Thr Asp Gly
                85                  90                  95

Asp Ser Leu Tyr Val Leu Ser Arg Ser Gly Pro Phe Phe Phe Val Ser
                100                 105                 110

Gly Asn Ser Glu Asn Cys Leu Lys Gly Gln Lys Leu Pro Val Lys Val
                115                 120                 125

Met Ser Ala Ala His His Ser His Ser Pro Arg Gln Pro Ser Pro Ser
    130                 135                 140

Pro Ser Pro Ser Pro Thr Leu Ser Pro Ser His Gln Ala Leu Ser Ser
145                 150                 155                 160

Pro Ala Pro Ser Pro Arg Val Val Leu Ser Glu Ser Glu Ala Leu Ala
                165                 170                 175

Pro Ala Pro Glu Pro Ala Lys Ala His Asn Ser Ala Gly Leu Val Ser
            180                 185                 190

Pro Arg Ala Val Ser Leu Gly Leu Val Leu Val Ile Ile Ser Phe
            195                 200                 205

Val Val
    210

<210> SEQ ID NO 22
<211> LENGTH: 199
<212> TYPE: PRT
<213> ORGANISM: Brassica juncea
```

```
<400> SEQUENCE: 22

Met Gly Leu Val Lys Ser Phe Gly Ala Tyr Leu Met Thr Val Met Leu
1               5                   10                  15

Ser Gly Leu Val Phe Ala Leu Gly Leu Ser Asn Gly Tyr Lys Phe Tyr
            20                  25                  30

Val Gly Gly Lys Asp Gly Trp Val Leu Thr Pro Ser Glu Asp Tyr Ser
        35                  40                  45

His Trp Ser His Arg Asn Arg Phe Gln Val Asn Asp Thr Leu Tyr Phe
    50                  55                  60

Lys Tyr Thr Glu Gly Lys Asp Ser Val Leu Glu Val Ser Gly Glu Glu
65                  70                  75                  80

Tyr Asn Lys Cys Asn Thr Thr His Pro Ile Thr Ser Leu Ser Asp Gly
                85                  90                  95

Asp Ser Leu Phe Val Leu Ser Arg Ser Gly Pro Phe Phe Phe Val Ser
            100                 105                 110

Gly Asn Ser Glu Asn Cys Val Lys Gly Gln Lys Leu Ala Val Lys Val
            115                 120                 125

Met Ser Thr Ala His His Ser His Ser Pro Arg Gln Ser Ser Pro Ser
130                 135                 140

Pro Ser Pro Ala Leu Ser Pro Val Ala Leu Ser Ser Pro Ala Pro Ser
145                 150                 155                 160

Pro Gly Val Ala Leu Ser Asp Ser Gly Pro Ala Lys Ala Arg Asn Ser
            165                 170                 175

Ala Gly Leu Val Gly Pro Glu Met Val Ser Leu Gly Leu Val Leu Gly
            180                 185                 190

Val Val Ile Ser Ser Met Val
            195

<210> SEQ ID NO 23
<211> LENGTH: 210
<212> TYPE: PRT
<213> ORGANISM: Brassica juncea

<400> SEQUENCE: 23

Met Gly Leu Ile Lys Arg Phe Asp Ala Tyr Leu Met Thr Val Met Leu
1               5                   10                  15

Met Ser Leu Gly Phe Ala Ile Gly Phe Ser Asn Gly Tyr Lys Phe Tyr
            20                  25                  30

Val Gly Gly Arg Asp Gly Trp Val Leu Thr Pro Ser Glu Asp Tyr Ser
        35                  40                  45

His Trp Ser Tyr Arg Ser Arg Phe Gln Val Asn Asp Thr Leu Tyr Phe
    50                  55                  60

Lys Tyr Pro Lys Gly Lys Asp Ser Val Leu Glu Val Ser Glu Glu Glu
65                  70                  75                  80

Phe Asn Thr Cys Asn Thr Thr His Pro Ile Thr Ser Leu Thr Asp Gly
                85                  90                  95

Asp Ser Leu Tyr Val Leu Ser Arg Ser Gly Pro Phe Phe Phe Val Ser
            100                 105                 110

Gly Asn Ser Glu Asn Cys Leu Lys Gly Gln Lys Leu Pro Val Lys Val
            115                 120                 125

Met Ser Ala Ala His His Ser His Ser Pro Arg Gln Pro Ser Pro Ser
130                 135                 140

Pro Ser Pro Ser Pro Thr Leu Ser Pro Ser His Gln Ala Leu Ser Ser
145                 150                 155                 160
```

```
Pro Ala Pro Ser Pro Arg Val Val Leu Ser Glu Ser Glu Ala Leu Ala
            165                 170                 175

Pro Ala Pro Glu Pro Ala Lys Ala His Asn Ser Ala Gly Leu Val Ser
        180                 185                 190

Pro Arg Ala Val Ser Leu Gly Leu Val Leu Val Ile Ile Ser Phe
    195                 200                 205

Val Val
210

<210> SEQ ID NO 24
<211> LENGTH: 212
<212> TYPE: PRT
<213> ORGANISM: Brassica juncea

<400> SEQUENCE: 24

Met Gly Leu Val Lys Thr Phe Asp Ala Tyr Leu Met Ile Val Met Leu
1               5                   10                  15

Ala Gly Leu Val Phe Ala Leu Gly Leu Ser Asn Gly Tyr Lys Phe Tyr
            20                  25                  30

Val Gly Gly Lys Asp Gly Trp Val Leu Thr Pro Ser Glu Asp Tyr Ser
        35                  40                  45

His Trp Ser His Arg Asn Arg Phe Gln Val Asn Asp Thr Leu Tyr Phe
    50                  55                  60

Lys Tyr Pro Lys Gly Lys Asp Ser Val Leu Glu Val Ser Glu Glu Glu
65                  70                  75                  80

Tyr Asn Thr Cys Asn Thr Thr His Pro Ile Thr Ser Val Ser Asp Gly
                85                  90                  95

Gly Ser Leu Phe Val Leu Ser Asn Ser Gly Pro Phe Phe Phe Val Ser
            100                 105                 110

Gly Asn Ser Glu Asn Cys Leu Lys Gly Gln Lys Leu Ala Val Asn Val
        115                 120                 125

Met Ser Thr Ala His His Ser Arg Ser Pro Arg Gln Pro Ser Pro Ser
    130                 135                 140

Pro Ser Pro Ser Pro Ser Pro Thr Leu Ser Pro Ile Ala Trp
145                 150                 155                 160

Ser Ser Pro Ala Pro Ser Pro Gly Val Val Leu Ser Asp Ser Glu Ala
                165                 170                 175

Leu Ala Pro Ala Pro Glu Pro Ala Lys Ala Arg Asn Ser Ala Cys Leu
            180                 185                 190

Val Gly Pro Gly Met Val Ser Leu Gly Leu Val Leu Phe Val Phe Ile
        195                 200                 205

Arg Ser Met Val
    210

<210> SEQ ID NO 25
<211> LENGTH: 208
<212> TYPE: PRT
<213> ORGANISM: Brassica juncea

<400> SEQUENCE: 25

Met Gly Leu Ile Lys Ser Phe Asp Ala Tyr Leu Met Ile Val Met Phe
1               5                   10                  15

Leu Ser Leu Gly Leu Ala Ile Gly Phe Ser Asn Gly Tyr Lys Phe Ser
            20                  25                  30

Val Gly Gly Lys Asp Gly Trp Val Leu Ala Pro Ser Glu Asp Tyr Ser
        35                  40                  45
```

His Trp Ser His Arg Asn Arg Phe Gln Val Asn Asp Thr Leu Tyr Phe
    50                  55                  60
Lys Tyr Pro Lys Gly Lys Asp Ser Val Leu Glu Val Ser Gln Glu Glu
 65                  70                  75                  80
Tyr Asn Thr Cys Asn Thr Thr His Pro Ile Thr Ser Leu Ser Asp Gly
                 85                  90                  95
Asp Ser Leu Phe Val Leu Ser Arg Ser Gly Pro Phe Phe Phe Val Ser
                100                 105                 110
Gly Ile Ser Ala Asn Cys Leu Lys Gly Gln Lys Leu Ala Val Lys Val
                115                 120                 125
Met Ser Ala Ala His His Ser His Ser Pro Arg Gln Pro Ser Pro Ser
130                 135                 140
Pro Ser Pro Ser Pro Thr Leu Ser Pro Val His Gln Ala Ser Pro Ala
145                 150                 155                 160
Pro Ser Pro Arg Val Val Leu Ser Asp Thr Glu Ala Leu Ala Pro Ala
                165                 170                 175
Pro Gly Pro Ala Lys Ala His Asn Ala Ala Gly Leu Val Ser Pro Arg
                180                 185                 190
Ala Val Ser Leu Gly Leu Val Leu Val Ile Ile Asn Cys Met Val
                195                 200                 205

<210> SEQ ID NO 26
<211> LENGTH: 621
<212> TYPE: DNA
<213> ORGANISM: Brassica napus

<400> SEQUENCE: 26
atgggtttgg tcaaaagctt tgatgcttac ttgatgattg tgatgttaac tggtttagtg      60
tttgcattag gattatcaaa tggttacaag ttctatgtag gtgggaaaga tggttgggtt     120
cttactcctt ccgaggatta ttctcattgg tctcaccgaa accggtttca agtcaacgac     180
actctttatt ttaagtaccc caagggaaaa gactcagtag tggaggtgag tgaagaagag     240
tacaacacat gcaacacgac tcaccccata acttccctct cagacggaga ctctctcttt     300
gtgcttagcc gctcgggtcc gttcttttc gtaagcggca actcggaaaa ctgtctcaaa     360
ggccagaagc tagccgtcaa cgtcatgtcg accgctcatc acagccgcag tcctcgtcag     420
ccatctccct caccatcacc gacactgtct ccgtcgcttg gtcatctccc agcgccttct     480
ccgggagtgg aactttctga ctcagaagct cttgctccgg cttcagaacc gccaaagct      540 cgcaattcgg ccagtttggt tggtcctggg atggtttctt gggattagt tctcgttgtt      600 ttcataaggt ccatggtcta g                                              621

<210> SEQ ID NO 27
<211> LENGTH: 633
<212> TYPE: DNA
<213> ORGANISM: Brassica napus

<400> SEQUENCE: 27
atgggtttga tcaaaaggtt tgatgcttat ttgatgactg tgatgttagt gagtttgggg      60
tttgcaattg gttttcaaa tgggtacaag ttctatgttg gtgggagaga tggttgggtc     120
cttactccat ccgaggacta ttctcattgg tcttatcgaa gccggtttca ggtcaatgac     180
actctttatt ttaagtaccc taaggggaaa gattcagtgt ggaggtgag tgaagaagaa     240 ttcaacacat gcaacactac tcacccaata acctccctca cggacggaga ctctctctat     300
gttcttagcc gctcaggtcc gttctttttt gtcagcggca actcagaaaa ttgtctcaaa     360

```
ggtcagaagc tacccgtcaa ggtcatgtcc accgcccacc acagccacag tcctcgtcag    420
ccatctccat cgccctcacc gtcatcgact ctgtctccaa gccatcaggc tttgtcatct    480
cctgcgcctt ctccgagagt ggttctttct gaatctgaag ctcttgctcc ggctccagga    540
ccagcgaaag ctcacaattc ggccggtttg gtgagtccta ggggggtctc tctaggattg    600
gttctcgtgg ttattataag tttcatggtt tag                                 633
```

<210> SEQ ID NO 28
<211> LENGTH: 633
<212> TYPE: DNA
<213> ORGANISM: Brassica napus

<400> SEQUENCE: 28

```
atgggtttgg tcaaaacctt tgatgtttac ttgatgattg tgatgttagc tggtttagtg     60
tttgcattag gattatcaaa tggttacaag ttctatgtag gtgggaaaga tggttgggtt    120
cttactcctt ccgaggatta ttctcattgg tctcaccgaa accggtttca agtcaacgac    180
actctttatt ttaagtaccc caagggaaaa gattcagtgt tggaggtgag tgaagaagag    240
tacaacacat gcaacacgac gcaccccata acttccgtct cagacggagg ctctctcttt    300
gtgcttagcc gctcaggtcc gttctttttc gtcagcggta actcggaaaa ctgtctcaaa    360
ggccagaagc tagccgtcaa cgtcatgtcg accgctcatc acagccgcag tcctcgtcag    420
ccatctccct caccatcacc atcaccatca ccgacactgt ctcccatcgc ttggtcatct    480
ccagcgcctt ctccgggagt ggttctttct gactcagaag ctcttgctcc agctccagaa    540
cccgccaaag ctcgcaattc ggcctgtttg gttggtcctg ggatggtttc tttgggatta    600
gttctctttg ttttcataag gtccatggtc tag                                 633
```

<210> SEQ ID NO 29
<211> LENGTH: 633
<212> TYPE: DNA
<213> ORGANISM: Brassica napus

<400> SEQUENCE: 29

```
atgggtttga tcaaaaggtt tgatgcctat ttgatgactg tgatgttaat gagtttgggg     60
tttgcaattg gttttcaaa tgggtacaag ttctatgtcg gtgggagaga tggttgggtc    120
cttactccat ccgaggacta ttctcattgg tcttatcgaa gccggtttca ggtcaatgac    180
actctttatt ttaagtaccc taaggggaaa gattcagtgt tggaggtgag tgaagaagaa    240
ttcaacacat gcaacactac tcacccaata acctccctca cggacggaga ctctctctat    300
gttcttagcc gctcaggtcc gttctttttt gtcagcggca actcagaaaa ttgtctcaaa    360
ggtcagaagc tacccgtgaa ggtcatgtcc gccgcccacc acagccacag tcctcgtcag    420
ccatctccat cgccctcacc gtcaccgact ctgtctccaa gccatcaggc tttgtcatct    480
ccagcgcctt ctccgagagt ggttctttct gaatctgaag ctcttgctcc ggctccagga    540
ccagcgaaag ctcacaattc ggccggtttg gtgagtccta gggcggtctc tctaggattg    600
gttctcgtgg ttattataag tttcgtgctt tag                                 633
```

<210> SEQ ID NO 30
<211> LENGTH: 621
<212> TYPE: DNA
<213> ORGANISM: Brassica oleracea

<400> SEQUENCE: 30

```
atgggtttgg tcaaaagctt tgatgcttac ttgatgattg tgatgttaac tggtttagtg      60
tttgcattag gattatcaaa tggttacaag ttctatgtag gtgggaaaga tggttgggtt     120
cttactcctt ccgaggatta ttctcattgg tctcaccgaa accggtttca agtcaacgac     180
actctttatt ttaagtaccc caagggaaaa gactcagtag tggaggtgag tgaagaagag     240
tacaacacat gcaacacgac tcaccccata acttccctct cagacggaga ctctctcttt     300
gtgcttagcc gctcgggtcc gttcttttc gtaagcggca actcggaaaa ctgtctcaaa      360
ggccagaagc tagccgtcaa cgtcatgtcg accgctcatc acagccgcag tcctcgtcag     420
ccatctccct caccatcacc gacactgtct ccgtcgcttg gtcatctccc agcgccttct     480
ccgggagtgg aactttctga ctcagaagct cttgctccgg cttcagaacc cgccaaagct     540
cgcaattcgg ccagtttggt tggtcctggg atggtttctt tgggattagt tctcgttgtt     600
ttcataaggt ccatggtcta g                                               621

<210> SEQ ID NO 31
<211> LENGTH: 636
<212> TYPE: DNA
<213> ORGANISM: Brassica oleracea

<400> SEQUENCE: 31
atgggtttga tcaaaaggtt tgatgcttat tgatgactg tgatgttaat gagtttaggg       60
ttatttgcaa ttgggttttc aaatgggtac aagttctatg ttggtgggag agatggttgg     120
gtccttactc catccgagga ctattctcat tggtcttatc gaagccggtt tcaggtcaat     180
gacactcttt attttaagta ccctaagggg aaagattcag tgttggaggt gagtgaagaa     240
gaattcaaca catgcaacac tactcaccca ataacctccc tcacggacgg agactctctc     300
tatgttctta gccgctcagg tccgttcttt tttgtcagcg gcaactcaga aaattgtctc     360
aaaggtcaga agctacccgt gaaggtcatg tccgccgccc accacagcca gtcctcgc       420 cagccatctc catcgccctc accgtcaccg actctgtctc caagccatca ggctttgtca     480
tctccagcgc cttctccgag agtggttctt tctgaatctg aagctcttgc tccggctcca     540
ggaccagcga agctcacaa tcggccggtt tggtgagtc ctagggcggt ctctctagga       600
ttggttctcg tggttattat aagtttcgtg gtttag                               636

<210> SEQ ID NO 32
<211> LENGTH: 639
<212> TYPE: DNA
<213> ORGANISM: Brassica rapa

<400> SEQUENCE: 32
atgggtttgg tcaaaacctt tgatgcttac ttgatgattg tgatgttagc tggtttagtg      60
tttgcattag gattatcaaa tggttacaag ttctatgtag gtgggaaaga tggttgggtt     120
cttactcctt ccgaggatta ttctcattgg tctcaccgaa accggtttca agtcaacgac     180
actctttatt ttaagtaccc caaggaaaaa gattcagtgt tggaggtgag tgaagaagag     240
tacaacacat gcaacacgac gcaccccata acttccgtct cagacggagg ctctctcttt     300
gtgcttagca actcaggtcc gttcttttc gtcagcggta actcggaaaa ctgtctcaaa      360
ggccagaagc tagccgtcaa cgtcatgtcg accgctcatc acagccgcag tcctcgtcag     420
ccatctccct caccatcacc atcaccatca ccatccga cactgtctcc catcgcttgg       480
tcatctccag cgccttctcc gggagtggtt ctttctgact cagaagctct tgctccagct     540
ccagaacccg ccaaagctcg caattcggcc tgtttggttg gtcctgggat ggtttctttg     600
```

```
ggattagttc tctttgtttt cataaggtcc atggtctag                             639
```

<210> SEQ ID NO 33
<211> LENGTH: 633
<212> TYPE: DNA
<213> ORGANISM: Brassica rapa

<400> SEQUENCE: 33

```
atgggtttga tcaaaaggtt tgatgcctat ttgatgactg tgatgttaat gagtttgggg      60
tttgcaattg gttttcaaa tgggtacaag ttctatgtcg gtgggagaga tggttgggtc     120
cttactccat ccgaggacta ttctcattgg tcttatcgaa gccggtttca ggtcaatgac    180
actctttatt ttaagtaccc taaggggaaa gattcagtgt tggaggtgag tgaagaagaa    240
ttcaacacat gcaacactac tcacccaata acctccctca cggacggaga ctctctctat    300
gttcttagcc gctcaggtcc gttcttttt gtcagcggca actcagaaaa ttgtctcaaa     360
ggtcagaagc tacccgtgaa ggtcatgtcc gccgcccacc acagccacag tcctcgtcag    420
ccatctccat cgccctcacc gtcaccgact ctgtctccaa gccatcaggc tttgtcatct    480
ccagcgcctt ctccgagagt ggttctttct gaatctgaag ctcttgctcc ggctccagaa    540
ccagcgaaag ctcacaattc ggccggtttg gtgagtccta gggcagtctc tctaggattg    600
gttctcgtgg ttattataag tttcgtggtt tag                                 633
```

<210> SEQ ID NO 34
<211> LENGTH: 597
<212> TYPE: DNA
<213> ORGANISM: Brassica juncea

<400> SEQUENCE: 34

```
atgggtttgg tcaaaagctt tggtgcttac ttgatgactg tgatgttaag tggtttggtg      60
tttgcattag gattatcaaa tggttacaag ttctatgtag gtgggaagga tggttgggtt    120
cttactcctt ccgaggatta ttctcattgg tctcaccgaa accggtttca agtcaacgac    180
actctttatt ttaagtacac agagggaaaa gattcagtgt tggaggtgag tggagaagaa    240
tacaacaaat gcaacacgac tcaccccata acttccctct cagacggaga ttctctcttt    300
gtgcttagcc gctctggtcc gttcttttc gtcagtggca actcggaaaa ctgtgtcaaa     360
ggccagaagc tagccgtcaa ggtcatgtcc accgcccacc acagccacag tcctcgtcag    420
tcatctccct caccgtcacc ggctctgtct cctgtcgctt tgtcatctcc agcgccttct    480
ccgggagtgg ctctttccga ctcaggaccc gcgaaagcac gcaactcagc aggtttggtt    540
ggtcctgaga tggtttcttt aggattggtt ctcggggttg tcataagttc catggtc       597
```

<210> SEQ ID NO 35
<211> LENGTH: 630
<212> TYPE: DNA
<213> ORGANISM: Brassica juncea

<400> SEQUENCE: 35

```
atgggtttga tcaaaaggtt tgatgcctat ttgatgactg tgatgttaat gagtttgggg      60
tttgcaattg gttttcaaa tgggtacaag ttctatgtcg gtgggagaga tggttgggtc     120
cttactccat ccgaggacta ttctcattgg tcttatcgaa gccggtttca ggtcaatgac    180
actctttatt ttaagtaccc taaggggaaa gattcagtgt tggaggtgag tgaagaagaa    240
ttcaacacat gcaacactac tcacccaata acctccctca cggacggaga ctctctctat    300
```

```
gttcttagcc gctcaggtcc gttctttttt gtcagcggca actcagaaaa ttgtctcaaa    360
ggtcagaagc tacccgtgaa ggtcatgtcc gccgcccacc acagccacag tcctcgtcag    420
ccatctccat cgccctcacc gtcaccgact ctgtctccaa gccatcaggc tttgtcatct    480
ccagcgcctt ctccgagagt ggttcttttct gaatctgaag ctcttgctcc ggctccagaa    540
ccagcgaaag ctcacaattc ggccggtttg gtgagtccta gggcagtctc tctaggattg    600
gttctcgtgg ttattataag tttcgtggtt                                     630

<210> SEQ ID NO 36
<211> LENGTH: 636
<212> TYPE: DNA
<213> ORGANISM: Brassica juncea

<400> SEQUENCE: 36
atgggtttgg tcaaaacctt tgatgcttac ttgatgattg tgatgttagc tggtttagtg     60
tttgcattag gattatcaaa tggttacaag ttctatgtag gtgggaaaga tggttgggtt    120
cttactcctt ccgaggatta ttctcattgg tctcaccgaa accggtttca agtcaacgac    180
actctttatt taagtaccc caagggaaaa gattcagtgt ggaggtgag tgaagaagag     240 tacaacacat gcaacgacgac gcaccccata acttccgtct cagacggagg ctctctcttt    300
gtgcttagca actcaggtcc gttcttttc gtcagcggta actcggaaaa ctgtctcaaa     360
ggccagaagc tagccgtcaa cgtcatgtcg accgctcatc acagccgcag tcctcgtcag    420
ccatctccct caccatcacc atcaccatca ccatcaccga cactgtctcc catcgcttgg    480
tcatctccag cgccttctcc gggagtggtt ctttctgact cagaagctct tgctccagct    540
ccagaacccg ccaaagctcg caattcggcc tgtttggttg gtcctgggat ggtttctttg    600
ggattagttc tctttgtttt cataaggtcc atggtc                              636

<210> SEQ ID NO 37
<211> LENGTH: 624
<212> TYPE: DNA
<213> ORGANISM: Brassica juncea

<400> SEQUENCE: 37
atgggtttga tcaaaagttt cgatgcttac ctgatgattg tgatgttctt gagtttgggg     60
cttgcaatag ggttttcaaa tgggtacaag ttctctgttg gtgggaaaga tggttgggtc    120
cttgctcctt ccgaggatta ttctcattgg tctcatcgaa accggtttca ggtcaacgac    180
actctttatt taagtaccc caaggggaaa gattcagtgt ggaggtgag tcaagaagag     240 tacaacacat gcaacaccac tcacccaatt acttctctct cggacggaga ctctctcttt    300
gtgcttagcc gctcaggtcc cttctttttt gtcagcggca tctcagcaaa ttgtctcaaa    360
ggccagaagc tagccgtcaa ggtcatgtca gccgcccacc acagccacag tcctcgtcag    420
ccatctccat cgccctcacc gtcaccgact ctgtctccag tccatcaggc ttctccagcg    480
ccttctccga gagtggttct ttctgacaca gaagctcttg ctccggctcc aggaccagcg    540
aaagctcaca atgcggccgg tttggttagt cctagggcgg tctctctagg attggtgctc    600
gtggttatta taaattgcat ggtt                                           624

<210> SEQ ID NO 38
<211> LENGTH: 22
<212> TYPE: DNA
<213> ORGANISM: Artificial Sequence
<220> FEATURE:
<223> OTHER INFORMATION: consensus motif 1
```

```
<400> SEQUENCE: 38
kwaratgact racaaattrg aa                                           22

<210> SEQ ID NO 39
<211> LENGTH: 30
<212> TYPE: DNA
<213> ORGANISM: Artificial Sequence
<220> FEATURE:
<223> OTHER INFORMATION: consensus motif 3

<400> SEQUENCE: 39
ccgttaagtc cattgcatgt ygaaacgtgt                                   30

<210> SEQ ID NO 40
<211> LENGTH: 16
<212> TYPE: DNA
<213> ORGANISM: Artificial Sequence
<220> FEATURE:
<223> OTHER INFORMATION: consensus motif 4

<400> SEQUENCE: 40
rraarakras caamrc                                                  16

<210> SEQ ID NO 41
<211> LENGTH: 15
<212> TYPE: DNA
<213> ORGANISM: Artificial Sequence
<220> FEATURE:
<223> OTHER INFORMATION: consensus motif 5

<400> SEQUENCE: 41
aaacgcttcw watta                                                   15

<210> SEQ ID NO 42
<211> LENGTH: 10
<212> TYPE: DNA
<213> ORGANISM: Artificial Sequence
<220> FEATURE:
<223> OTHER INFORMATION: consensus motif 7

<400> SEQUENCE: 42 tmtcwagaka                                                         10

<210> SEQ ID NO 43
<211> LENGTH: 13
<212> TYPE: DNA
<213> ORGANISM: Artificial Sequence
<220> FEATURE:
<223> OTHER INFORMATION: consensus motif 8

<400> SEQUENCE: 43
atgcagsmaa amg                                                     13

<210> SEQ ID NO 44
<211> LENGTH: 35
<212> TYPE: DNA
<213> ORGANISM: Artificial Sequence
<220> FEATURE:
<223> OTHER INFORMATION: consensus motif 9

<400> SEQUENCE: 44
aacggctatk asttmtctrc ttycacyata aatac                             35

<210> SEQ ID NO 45
```

```
<211> LENGTH: 11
<212> TYPE: DNA
<213> ORGANISM: Artificial Sequence
<220> FEATURE:
<223> OTHER INFORMATION: consensus motif 10

<400> SEQUENCE: 45
kcacysaaga g                                                            11

<210> SEQ ID NO 46
<211> LENGTH: 15
<212> TYPE: DNA
<213> ORGANISM: Artificial Sequence
<220> FEATURE:
<223> OTHER INFORMATION: consensus motif 11

<400> SEQUENCE: 46
acasabttca araga                                                        15

<210> SEQ ID NO 47
<211> LENGTH: 16
<212> TYPE: DNA
<213> ORGANISM: Artificial Sequence
<220> FEATURE:
<223> OTHER INFORMATION: consensus motif 12

<400> SEQUENCE: 47
ttraggtyta gtyama                                                       16

<210> SEQ ID NO 48
<211> LENGTH: 350
<212> TYPE: DNA
<213> ORGANISM: Brassica napus

<400> SEQUENCE: 48
aaatctagta agtttattaa aaatgaattt cagtttttag ttaaatgact aacaaattgg        60
aacatctggt gtaaaatggc tgttggctgg gagtaaataa agtgtgtgaa aagaagatag       120
ccgttaagtc cattgcatgt cgaaacgtgt aaaaagaaa gaggagcaaa accaaaacgc        180
ttcaaattaa tttgcatatt ctctagagaa tccatgcagg aaaaagtttc acctaacggc      240
tatgacttct ctactttcac cataaataca catacaagca ccgaagagca acacagactt      300
caagagatca gtgagtaatt actttgaggt ttagttaaaa cttttgggga                 350

<210> SEQ ID NO 49
<211> LENGTH: 355
<212> TYPE: DNA
<213> ORGANISM: Brassica napus

<400> SEQUENCE: 49 ttatttttt aagaaaattg aatttcagct ttatattaaa tgactgacaa attagaagat        60
ctagttttaa atggttgttt gtgatttgag gagggagtaa atgaaatgtg tgaaaagaag      120
agagatggcc gttaagtcca ttgcatgttg aaacgtgtga agaaaacaaa agaggagcaa      180
aacttgaaac gcttcttatt aattttgcat attctctaga gagtcgaagt tgatgcagcc      240
aaaagctaac ggctatgact tctctacttt cactataaat acgcatacaa gcactgaaga      300
gcaacacaca tttcaagaga ctgatttatt tgaggtctag ttaaagtttg gaggg           355

<210> SEQ ID NO 50
<211> LENGTH: 355
<212> TYPE: DNA
<213> ORGANISM: Brassica napus
```

<400> SEQUENCE: 50

```
attatgtaag cttattaaca attgatttca ttttttttgt tttgttagat gactaacaaa    60
ttggaacatc tgttggaaaa tggctgtttg cggggagtaa ataaagtgtg tgaaaagaag   120
atagccgtta agtccattgc atgtcgaaac gtgtaaaaaa ggaagaggag caaagccaaa   180
acgcttcaaa ttaatttgca tattctcaag ataacccatg caggcaaaag cttcatctaa   240
cggctatgac ttatctgctt tcaccataaa tacacataca agcacccaag agcaacacag   300
agttcaagag atcagtgagt aattgtttta aggtttagtt acaagttttg gagag        355
```

<210> SEQ ID NO 51
<211> LENGTH: 345
<212> TYPE: DNA
<213> ORGANISM: Brassica napus

<400> SEQUENCE: 51

```
aagaaaattg aatttcagct ttatattaaa tgactgacaa attagaagat ctagttttaa    60
atggttgttt gtgatttgag gagggagtaa atgaaatgtg tgaaaagaag agagatggcc   120
gttaagtcca ttgcatgttg aaacgtgtga agaaaacaaa agaggagcaa aacttgaaac   180
gcttcttatt aattttgcat attctctaga gagtcgaagt tgatgcagcc aaaagctaac   240
ggctatgact ctctactttt cactataaat acgcatacaa gcactgaaga gcaacacaca   300
tttcaagaga ctgatttatt tgaggtctag ttaaagtttg gaggg                   345
```

<210> SEQ ID NO 52
<211> LENGTH: 350
<212> TYPE: DNA
<213> ORGANISM: Brassica oleracea

<400> SEQUENCE: 52

```
aatctagtaa gtttattaaa aatgaatttc agtttttagt taaatgacta acaaattgga    60
acatctggtg taaaatggct gttggctggg agtaaataaa gtgtgtgaaa agaagatagc   120
cgttaagtcc attgcatgtc gaacgtgta aaaagaaag aggagcaaaa ccaaaacgct   180
tcaaattaat ttgcatattc tctagagaat ccatgcagga aaaagtttca cctaacggct   240
atgacttctc tactttcacc ataaatacac atacaagcac cgaagagcaa cacagacttc   300
aagagatcag tgagtaatta ctttgaggtt tagttaaaac ttttggggag              350
```

<210> SEQ ID NO 53
<211> LENGTH: 355
<212> TYPE: DNA
<213> ORGANISM: Brassica oleracea

<400> SEQUENCE: 53

```
tacgcaagtt atttaaaaaa aaaaattaaa tttcagcttt atattaaatg actgacaaat    60
tagaagatct agtttcaaat ggttgtttgt gatttgagga gggagtaaat aaaaattgtg   120
aaaagaagag agatggccgt taagtccatt gcatgttgaa acgtgtgaag aaaacaaaag   180
aggagcaaaa cttgaaacgc ttcttattaa ttttgcatgt tctctagaga gtcgaagttg   240
atgcagccaa aagttaacgg ctatgacttc tctactttca ctataaatac gcactgaaga   300
gcaacacaca tttcaagaga ctgatttatt tgaggtctag tcaaagtttg gagag        355
```

<210> SEQ ID NO 54
<211> LENGTH: 350
<212> TYPE: DNA

<213> ORGANISM: Brassica rapa

<400> SEQUENCE: 54

| | | | | | |
|---|---|---|---|---|---|
| tatgtaagct | tattaacaat | tgatttcatt | tttttttgt | tagatgacta | acaaattgga | 60 |
| acatctgttg | gaaatggct | gtttgcgggg | agtaaataaa | gtgtgtgaaa | agaaaatagc | 120 |
| cgttaagtcc | attgcatgtc | gaaacgtgta | aaaaggaag | aggagcaaaa | ccaaaacgct | 180 |
| tcaaattaat | ttgcatattc | tctagataac | ccatgcaggc | aaaagcttca | tctaacggct | 240 |
| atgacttctc | tgctttcacc | ataaatacac | atacaagcac | ccaagagcaa | cacagagttc | 300 |
| aagagatcag | tgagtaattg | ttttaaggtt | tagttacaag | ttttggagag | | 350 |

<210> SEQ ID NO 55
<211> LENGTH: 395
<212> TYPE: DNA
<213> ORGANISM: Brassica rapa

<400> SEQUENCE: 55

| | | | | | |
|---|---|---|---|---|---|
| cgatccaaac | caaccaact | atggtttact | tcagctggaa | aaattctaga | accgaactaa | 60 |
| ccaaaccgaa | ccgaactcga | accgaaccga | taaataacc | gaagtgccca | ccctagttt | 120 |
| gtgatttgag | gagggagtaa | atgaattgtg | tgaaagaag | agagatggcc | gttaagtcca | 180 |
| ttgcatgttg | aaacgtgtga | agaaaacaaa | agaggagcaa | aacttgaaac | gcttcttatt | 240 |
| aattttgcat | attctctaga | gagtcgaagt | tgatgcagcc | aaaagctaac | ggctatgact | 300 |
| tctctacttt | cactataaat | acgcatacaa | gcactgaaga | gcaacacaca | tttcaagaga | 360 |
| ttgatttatt | tgaggtctag | ttaaagtttg | gaggg | | | 395 |

<210> SEQ ID NO 56
<211> LENGTH: 360
<212> TYPE: DNA
<213> ORGANISM: Brassica juncea

<400> SEQUENCE: 56

| | | | | | |
|---|---|---|---|---|---|
| aaacaagttt | agaaaaataa | atttcagtat | ttagttaaat | gactaataaa | tcggagcatc | 60 |
| aggtgaaaaa | aaaaggctgt | ttgtgctttg | ctagggagta | tataaagaa | agtgaaaga | 120 |
| agatagccgt | taagtccatt | gcatgtcgaa | acgtgtaaaa | aagaagagaa | gcaaaaccaa | 180 |
| aacgcttcaa | attagtttgc | acattctcta | gagaatccat | gcagccaaac | gcttcaccta | 240 |
| acggctatta | cttctctact | tccaccataa | atacacatac | atgcaagcac | ccaagaggca | 300 |
| agagcaaaca | cagagttcaa | gagagcgaat | acttgaggtt | tagttaaaag | atttggaaag | 360 |

<210> SEQ ID NO 57
<211> LENGTH: 360
<212> TYPE: DNA
<213> ORGANISM: Brassica juncea

<400> SEQUENCE: 57

| | | | | | |
|---|---|---|---|---|---|
| gcaagttatt | tttttaagaa | aattgaattt | cagctttata | ttaaatgact | gacaaattag | 60 |
| aagatctagt | tttaaatggt | tgtttgtgat | ttgaggaggg | agtaaatgaa | atgtgtgaaa | 120 |
| agaagagaga | tggccgttaa | gtccattgca | tgttgaaacg | tgtgaagaaa | acaaaagagg | 180 |
| agcaaaactt | gaaacgcttc | ttattaattt | tgcatattct | ctagagagtc | gaagttgatg | 240 |
| cagccaaaag | ctaacggcta | tgacttctct | actttcacta | taaatacgca | tacaagcact | 300 |
| gaagagcaac | acacatttca | agagactgat | ttatttgagg | tctagttaaa | gtttggaggg | 360 |

```
<210> SEQ ID NO 58
<211> LENGTH: 350
<212> TYPE: DNA
<213> ORGANISM: Brassica juncea

<400> SEQUENCE: 58
gtaagcttat taacaattga tttcattttt tttgttttgt tagatgacta acaaattgga      60
acatctgttg gaaatggct gtttgcgggg agtaaataaa gtgtgtgaaa agaagatagc     120
cgttaagtcc attgcatgtc gaaacgtgta aaaaaggaag aggagcaaag ccaaaacgct    180
tcaaattaat ttgcatattc tcaagataac ccatgcaggc aaaagcttca tctaacggct   240
atgacttctc tgctttcacc ataaatacac atacaagcac ccaagagcaa cacagagttc    300
aagagatcag tgagtaattg tttaaggtt tagttacaag ttttggagag               350

<210> SEQ ID NO 59
<211> LENGTH: 345
<212> TYPE: DNA
<213> ORGANISM: Brassica juncea

<400> SEQUENCE: 59
gtaattttaa acagacatgg atttcaggtt taaattaaat gactaacaaa ttagaagatc      60
tagttttaaa tggttttttt cttcttggag aggggggtgg taaacaaaaa gtgtgaaaag    120
aagatatccg ttaagtccat tgcatgtcga aacgtgtgaa aaaatgacca acactgaaac    180
gcttctaatt aattttgcat atattatcta gagattcgat gcagccaaaa gcttcaccca    240
acggctatga gttctctact ttcaccataa atacacatca aatcacccaa gagtaacaca    300
gttcaaaaga gtaatttact tgaggtctag ttaaatttta gagag                    345
```